US008299076B2

(12) United States Patent
Marlow et al.

(10) Patent No.: US 8,299,076 B2
(45) Date of Patent: Oct. 30, 2012

(54) CRYSTALLINE FORMS OF 2-(2-FLOURO-4-IODOPHENYLAMINO)-N-(2-HYDROXY-ETHOXY)-1,5-DIMETHYL-6-OXO-1,6-DIHYDROPYRIDINE-3-CARBOXAMIDE

(75) Inventors: Allison L. Marlow, Louisville, CO (US); Eli Wallace, Lyons, CO (US); Jeongbeob Seo, Broomfield, CO (US); Joseph P. Lyssikatos, Superior, CO (US); Hong Woon Yang, Superior, CO (US); Jim Blake, Longmont, CO (US); Richard Anthony Storey, Cheshire (GB); Rebecca Jane Booth, Cheshire (GB); John David Pittam, Cheshire (GB); John Leonard, Cheshire (GB); Mark Richard Fielding, Cheshire (GB)

(73) Assignees: Array Biopharma Inc., Boulder, CO (US); Astrazeneca AB, Sodertalje (SE)

( * ) Notice: Subject to any disclaimer, the term of this patent is extended or adjusted under 35 U.S.C. 154(b) by 866 days.

(21) Appl. No.: 11/914,433

(22) PCT Filed: May 17, 2006

(86) PCT No.: PCT/US2006/019108
§ 371 (c)(1),
(2), (4) Date: Nov. 14, 2007

(87) PCT Pub. No.: WO2007/044084
PCT Pub. Date: Apr. 19, 2007

(65) Prior Publication Data
US 2008/0280957 A1 Nov. 13, 2008

Related U.S. Application Data

(60) Provisional application No. 60/682,335, filed on May 18, 2005.

(51) Int. Cl.
*A01N 43/58* (2006.01)
*A01N 43/54* (2006.01)
*A01N 43/40* (2006.01)
*C07D 401/00* (2006.01)
*C07D 239/02* (2006.01)
*C07D 487/00* (2006.01)
*A61P 35/00* (2006.01)
*A61P 29/00* (2006.01)

(52) U.S. Cl. ........ 514/248; 514/269; 514/274; 514/338; 514/340; 514/341; 544/238; 544/316; 544/236; 546/279.1

(58) Field of Classification Search ................. 514/349, 514/248, 269, 274, 338, 340, 341; 544/297, 544/238, 316, 236; 546/297, 279.1
See application file for complete search history.

(56) References Cited

U.S. PATENT DOCUMENTS

| | | |
|---|---|---|
| 4,704,459 A | 11/1987 | Todo et al. |
| 4,851,535 A | 7/1989 | Todo et al. |
| 5,231,094 A | 7/1993 | Bru-Magniez et al. |
| 5,525,625 A | 6/1996 | Bridges et al. |
| 5,750,545 A | 5/1998 | Akahoshi et al. |
| 6,310,060 B1 | 10/2001 | Barrett et al. |
| 6,440,966 B1 | 8/2002 | Barrett et al. |
| 6,469,004 B1 | 10/2002 | Barrett et al. |
| 6,506,798 B1 | 1/2003 | Barrett et al. |
| 6,545,030 B1 | 4/2003 | Barrett et al. |
| 6,642,215 B2 | 11/2003 | Madsen et al. |
| 6,750,217 B2 | 6/2004 | Barrett et al. |
| 6,821,963 B2 | 11/2004 | Barrett et al. |
| 6,831,175 B2 | 12/2004 | Li et al. |
| 6,835,749 B2 | 12/2004 | Tecle |
| 6,960,614 B2 | 11/2005 | Barrett et al. |
| 7,001,905 B2 | 2/2006 | Biwersi et al. |
| 7,030,119 B1 | 4/2006 | Barrett et al. |
| 7,067,532 B2 | 6/2006 | Boyle et al. |
| 7,211,572 B2 | 5/2007 | Miyazaki et al. |
| 7,235,537 B2 | 6/2007 | Wallace et al. |
| 7,273,877 B2 | 9/2007 | Black et al. |
| 7,425,637 B2 | 9/2008 | Wallace et al. |
| 7,517,994 B2 * | 4/2009 | Marlow et al. ............... 546/291 |
| 7,598,383 B2 | 10/2009 | Marlow et al. |
| 7,732,616 B2 | 6/2010 | Marlow et al. |
| 7,893,065 B2 | 2/2011 | Marlow et al. |
| 2003/0004193 A1 | 1/2003 | Barrett et al. |

(Continued)

FOREIGN PATENT DOCUMENTS

| | | |
|---|---|---|
| GB | 1373314 | 11/1974 |
| GB | 1459522 | 12/1976 |
| JP | 49113827 A | 10/1974 |
| WO | 95/03286 A1 | 2/1995 |
| WO | 98/43960 | 10/1998 |
| WO | 99/01421 A1 | 1/1999 |
| WO | 99/01426 A1 | 1/1999 |
| WO | 00/40237 | 7/2000 |
| WO | 00/41505 | 7/2000 |
| WO | 00/41994 A1 | 7/2000 |

(Continued)

OTHER PUBLICATIONS

ClinicalTrials.gov, last updated Mar. 16, 2009, http://clinicaltrials.gov/ct2/show/NCT00174369, downloaded Apr. 29, 2009.*

(Continued)

*Primary Examiner* — James O Wilson
*Assistant Examiner* — Cecilia M Jaisle
(74) *Attorney, Agent, or Firm* — John R. Moore, Esq.; Sarah S. Mastous, Agent; Viksnins Harris & Padys PLLP

(57) ABSTRACT

Disclosed are crystalline forms of 2-(2-fluoro-4-iodophenylamino)-N-(2-hydroxyethoxy)-1,5-dimethyl-6-oxo-1,6-dihydropyridine-3-carboxamide useful in the treatment of hyperproliferative diseases, such as cancer and inflammation, in mammals, and inflammatory conditions. Also disclosed are methods of using such compounds in the treatment of hyperproliferative diseases in mammals and pharmaceutical compositions containing such compounds.

24 Claims, 15 Drawing Sheets

U.S. PATENT DOCUMENTS

| | | |
|---|---|---|
| 2003/0045521 A1 | 3/2003 | Tecle |
| 2003/0078428 A1 | 4/2003 | Barrett et al. |
| 2003/0092748 A1 | 5/2003 | Barrett et al. |
| 2003/0195183 A1 | 10/2003 | Zhilov |
| 2003/0199511 A1 | 10/2003 | Li et al. |
| 2003/0216460 A1 | 11/2003 | Wallace et al. |
| 2003/0232869 A1 | 12/2003 | Wallace et al. |
| 2004/0039208 A1 | 2/2004 | Chen et al. |
| 2004/0116710 A1 | 6/2004 | Wallace et al. |
| 2004/0141924 A1 | 7/2004 | Bridges et al. |
| 2005/0026964 A1 | 2/2005 | Black et al. |
| 2005/0054701 A1 | 3/2005 | Wallace et al. |
| 2005/0250782 A1 | 11/2005 | Marlow et al. |
| 2005/0256123 A1 | 11/2005 | Marlow et al. |
| 2006/0046999 A1 | 3/2006 | Alonso-Alija et al. |
| 2007/0112038 A1* | 5/2007 | Marlow et al. ............... 514/344 |
| 2008/0280918 A1 | 11/2008 | Buil Albero et al. |
| 2009/0131435 A1 | 5/2009 | Marlow et al. |
| 2009/0143389 A1 | 6/2009 | Blake et al. |
| 2009/0143579 A1 | 6/2009 | Blake et al. |
| 2009/0215834 A1 | 8/2009 | Marlow et al. |
| 2010/0063053 A1 | 3/2010 | Marlow et al. |
| 2011/0178136 A1 | 7/2011 | Marlow et al. |
| 2011/0183981 A1 | 7/2011 | Marlow et al. |
| 2011/0288092 A1 | 11/2011 | Marlow et al. |

FOREIGN PATENT DOCUMENTS

| | | |
|---|---|---|
| WO | 00/42002 A1 | 7/2000 |
| WO | 00/42003 A1 | 7/2000 |
| WO | 00/42022 A1 | 7/2000 |
| WO | 00/42029 A1 | 7/2000 |
| WO | 20000040235 A2 | 7/2000 |
| WO | 00/68201 | 11/2000 |
| WO | 01/05390 A2 | 1/2001 |
| WO | 01/05391 | 1/2001 |
| WO | 01/05392 | 1/2001 |
| WO | 01/05393 | 1/2001 |
| WO | 01/68619 A1 | 9/2001 |
| WO | 02/06213 A2 | 1/2002 |
| WO | 02/18319 A1 | 3/2002 |
| WO | 02/44166 A1 | 6/2002 |
| WO | 03/077855 A2 | 9/2003 |
| WO | 03/077914 A1 | 9/2003 |
| WO | 2003/076405 | 9/2003 |
| WO | 2005/000818 | 1/2005 |
| WO | 2005/123692 | 12/2005 |
| WO | 2007/044084 A2 | 4/2007 |

OTHER PUBLICATIONS

Konykhova et al., "Unusual Reaction of Enhydrazines with Oxalyl Chloride", Chemistry of Heterocyclic Compounds, 2001, 647-648, 37(5).

Schober et al., "Pyridazines with Heteroatom Substituents in Positions 3 and 5. 6. SN Reactions in Position of 6 of 2-aryl-5-hydroxypyridazin-3(2H)-ones", Journal of Heterocyclic Chemistry, 1990, 471-477, 27(3).

Gotthardt et al., "Synthesis and Physical Properties of First 3,3-bridged Bis- and Tris(1,3-thiazolium-4-olates) as well as one 5,5-Bridged Bis-(1,3-thiazolium-4-olate) and its Conversion into 3,3-(1,4-pheylene)BisA2(1ETA)-pyridononeU", Chemische Berichte, Verlag Chemie GMBH, 1987, 1017-1022, 120(b), Weinheim Germany.

Potts et al., "Mesoionic Compounds, XXXII Cycloaddition Reactions of the Anhydro-4-Hydroxythiazolium Hydroxide System with Olefinic Dipolarophiles", Journal of Organic Chemistry; 1974; pp. 3631-3640 39(25).

Potts et al., "Mesoionic Compounds, XXXI Preparation and Cycloaddition Reactions of the Anhydro-4-Hydroxythiazolium Hydroxide System with Acetylenic Dipolarophiles", Journal of Organic Chemistry, 1974 pp. 3627-3630 39(25).

Ried, et al."Reactions with Cyclobutenediones XXIX. Structure and reactions of Phenylcyclobutenedione-Enamine 1:1 Addition Compounds", Justus Liebigs Annalen Der Chemie, 1972, 1-12, 762.

Ried, et al., "Reactions of Cyclobutenediones. XX Synthesis and Reactivity of p-Substituted Phenylcyclobutenediones", Chemische Berichte, 1971, 2622-2628, 104(8).

Sebolt-Leopold, et al., "Blocade of the MAP Kinase Pathway Suppresses Growth of Colon Tumors in vivo", Nature Medicine, vol. 5, No. 7, Jul. 1999, 810-816.

Bachman et al., "Further Studies of Aminobenzacridines", Journal of Organic Chemistry; 1948; pp. 89-96; vol. 13.

Morau et al., "Synthesis and Anticonvulsant Properties of Triazolo- and Imidazopyridazinyl Carboxamides and Carboxylic Acids", Bioorganic & Medicinal Chemistry; 1998, pp. 983-991; vol. 6; Elsevier Science Ltd.

Viaud, M-C,et al., "Acylation of Oxazolo[4,5-b]pyridines and Pyrrolo[2-3-b]pyridin-2(2H)-ones", Tetrahedron, 1997, pp. 5159-5168 vol. 53, No. 14, Elsevier Science Ltd.

Patani et al., "Bioisosterism: A Rational Approach in Drug Design", Chem. Rev., 96, 1996, pp. 3147-3176.

Lima et al., "Bioisosterism: A Useful Strategy for Molecular Modification and Drug Design", Current Med. Chem., 12, 2005, pp. 23-49.

Search Report corresponding to European Patent Application No. 04811727.9-1211.

U.S. Appl. No. 10/992,612, Restriction Requirement dated Sep. 24, 2007.

U.S. Appl. No. 10/992,612, Non-Final Office Action Dated Jan. 23, 2008.

U.S. Appl. No. 10/992,612, Final Office Action Dated Aug. 7, 2008.

U.S. Appl. No. 10/992,612, Notice of Allowance Dated Nov. 20, 2008.

U.S. Appl. No. 11/132,164, Restriction Requirement Dated Aug. 23, 2007.

U.S. Appl. No. 11/132,164, Non-Final Office Action Dated Jan. 4, 2008.

U.S. Appl. No. 11/132,164, Notice Allowance Dated May 30, 2008.

U.S. Appl. No. 11/435,562, Non-Final Office Action Dated Sep. 5, 2008.

U.S. Appl. No. 11/435,562, Final Office Action Dated Feb. 20, 2009.

U.S. Appl. No. 11/435,562, Advisory Action Dated Apr. 30, 2009.

U.S. Appl. No. 11/435,562, Notice of Allowance Dated Jul. 27, 2009.

Sathornsumetee et al., "AAL881, a Novel Small Molecule Inhibitor of RAF and Vascular Endothelial Growth Factor Receptor Activities, Blocks the Growth of Malignant Glioma", *Cancer Res*, 66 (17), pp. 8722-8730, 2006.

Trujillo, "MEK inhibitors: a patent review 2008-2010", *Expert Opin. Ther. Patents*, 21(7), pp. 1045-1069, 2011.

Affidavit of Eli Wallace submitted in corresponding Chinese Application No. 200480040660.7, dated Mar. 21, 2011, pp. 1-4.

Office Action for corresponding Japanese Application No. 2006-541581, dated Oct. 26, 2010, 7 pages.

Vippagunta, Sudha R., et al., "Crystalline Solids", Advanced Drug Delivery Reviews, 48 (2001), pp. 3-26.

Yogo, Motoi et al., "Fused 1,3-Oxazine Derivatives. Synthesis of 2H-1,3-Oxazino[5,6-b]-quinoxaline-2,4(3H)diones (1-Oxaalloxazines), 2H-1,3-Oxazino-[6,5-b]quinoline-2,4(3H)-diones (5-Deaza-1—oxaalloxazines), and 2H-Pyrido[3,2-e]-1,3-oxazine-2,4(3H)-diones", Chem. Pharm. Bull., 32(5), pp. 1761-1769 (1984).

Kinoshita, Toshio et al., "Stable Sulfur Ylides. VIII. The Reactions of 1,3-Oxazin-4-one Derivatives", Chem. Pharm. Bull., 28(10), pp. 2892-2899 (1980).

Griesser, Ulrich J., "The Importance of Solvates", Polymorphism in the Pharmaceutical Industry, Ed. Rolf Hilfiker, vol. 2006, pp. 211-230 (2006).

Search Report corresponding to PCT International Application No. PCT/US2004/039060.

Search Report corresponding to European Patent Application No. 04811727.9-1211, 2006.

\* cited by examiner

CRYSTALLINE FORMS OF 2-(2-FLOURO-4-IODOPHENYLAMINO)-N-(2-HYDROXY-ETHOXY)-1,5-DIMETHYL-6-OXO-1,6-DIHYDROPYRIDINE-3-CARBOXAMIDE

BACKGROUND OF THE INVENTION

1. Field of the Invention

This invention relates to a series of novel heterocyclic compounds that are useful in the treatment of hyperproliferative diseases, such as cancer and inflammation, in mammals. This invention also relates to a method of using such compounds in the treatment of hyperproliferative diseases in mammals, especially humans, and to pharmaceutical compositions containing such compounds.

2. Description of the State of the Art

Cell signaling through growth factor receptors and protein kinases is an important regulator of cell growth, proliferation and differentiation. In normal cell growth, growth factors, through receptor activation (i.e. PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK and 2 on two serine residues (S218 and S222 for MEK1 and S222 and S226 for MEK2) (Ahn et al., *Methods in Enzymology,* 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology,* 2001, 332, 417-431). Phosphorylated ERK dimerizes and then translocates to the nucleus where it accumulates (Khokhlatchev et al., *Cell,* 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell,* 2000, 6, 1343-1354). Overall, treatment of cells with growth factors leads to the activation of ERK1 and 2 which results in proliferation and, in some cases, differentiation (Lewis et al., *Adv. Cancer Res.,* 1998, 74, 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science,* 1993, 260, 1834-1837). Recently, bRaf mutations have been identified in more than 60% of malignant melanoma (Davies, H. et al., *Nature,* 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., *Oncogene,* 1999, 18, 813-822). Hence, there is a strong correlation between cancers and an overactive MAP kinase pathway resulting from genetic mutations.

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine,* 1999, 5 (7), 810-816; Trachet et al., AACR Apr. 6-10, 2002, Poster #5426; Tecle, H., IBC 2$^{nd}$ International Conference of Protein Kinases, Sep. 9-10, 2002), block static allodynia in animals (WO 01/05390) and inhibit growth of acute myeloid leukemia cells (Milella et al., *J. Clin. Invest.,* 2001, 108 (6), 851-859).

Small molecule inhibitors of MEK have been disclosed, including in U.S. Patent Publication Nos. 2003/0232869, 2004/0116710, and 2003/0216460, and U.S. patent application Ser. Nos. 10/654,580 and 10/929,295, each of which is hereby incorporated by reference. At least fifteen additional patent applications have appeared in the last several years. See, for example: U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077914; and WO 03/077855.

SUMMARY OF THE INVENTION

This invention provides novel heterocyclic compounds, and pharmaceutically acceptable salts and prodrugs thereof, which are useful in the treatment of hyperproliferative diseases. It has been found that 6-oxo-1,6-dihydropyridazine and 6-oxo-1,6-dihydropyridine compounds having specific substituents as described herein are potent inhibitors of the MEK enzyme.

More specifically, one aspect of the present invention provides compounds including tautomers, metabolites, resolved enantiomers, diastereomers, solvates, and pharmaceutically acceptable salts thereof, said compound having the Formula I:

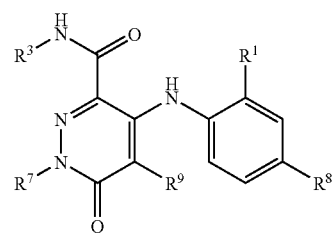

wherein:

$R^1$ is Cl or F;

$R^3$ is H, Me, Et, OH, MeO-, EtO-, HOCH$_2$CH$_2$O—, HOCH$_2$C(Me)$_2$O—, (S)-MeCH(OH)CH$_2$O—, (R)—HOCH$_2$CH(OH)CH$_2$O—, cyclopropyl-CH$_2$O—, HOCH$_2$CH$_2$—,

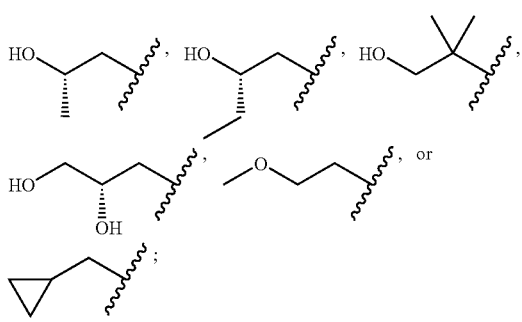

R⁷ is cyclopropyl-CH₂— or $C_1$-$C_4$ alkyl, wherein said alkyl is optionally substituted with one or more F;
R⁸ is Br, I or SMe; and
R⁹ is $CH_3$, $CH_2F$, $CHF_2$, $CF_3$, F or Cl.

Yet another aspect of this invention provides compounds, including tautomers, metabolites, resolved enantiomers, diastereomers, solvates, and pharmaceutically acceptable salts thereof, said compound having the Formula IV:

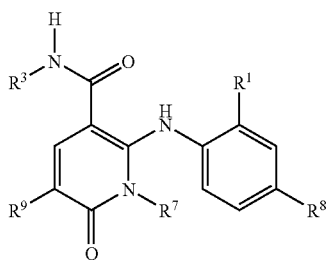

IV wherein:
R¹ is Cl or F;
R³ is H, Me, Et, OH, MeO-, EtO-, $HOCH_2CH_2O$—, $HOCH_2C(Me)_2O$—, (S)-$MeCH(OH)CH_2O$—, (R)-$HOCH_2CH(OH)CH_2O$—, cyclopropyl-$CH_2O$—, $HOCH_2CH_2$—,

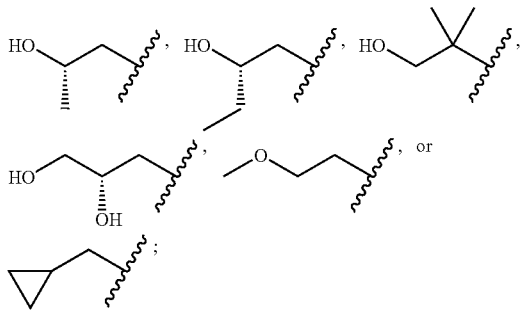

R⁷ is methyl or ethyl, wherein said methyl and ethyl are optionally substituted with one or more F;
R⁸ is Br, I or SMe; and
R⁹ is H, $C_1$-$C_4$ alkyl, Cl or CN, wherein said alkyl is optionally substituted with one or more groups independently selected from F or CN provided that:
a) when R¹ is F, R⁸ is Br, R⁹ is H, and R³ is $HOCH_2CH_2O$, then R⁷ cannot be Me or Et;
b) when R¹ is F, R⁸ is I, R⁹ is H, and R³ is MeO, then R⁷ cannot be Me;
c) when R¹ is F, R⁸ is Me, R⁹ is H, and R³ is $HOCH_2CH_2O$, then R⁷ cannot be Me and
d) when R¹ is F, R⁸ is Br, R⁹ is H, and R³ is cyclopropyl-$CH_2O$, then R⁷ cannot be Me.

In a further aspect, the present invention provides two crystalline forms of a compound of Formula XI

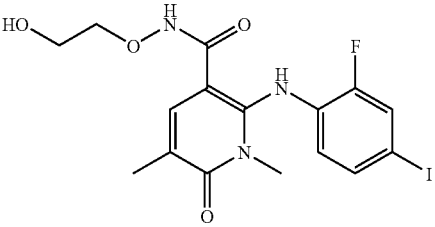

XI wherein the two crystalline forms are designated as Form 1, 2-(2-fluoro-4-iodophenylamino)-N-(2-hydroxyethoxy)-1,5-dimethyl-6-oxo-1,6-dihydropyridine-3-carboxamide and Form 2, 2-(2-fluoro-4-iodophenylamino)-N-(2-hydroxyethoxy)-1,5-dimethyl-6-oxo-1,6-dihydropyridine-3-carboxamide.

Also provided are methods of preparing Form 1 and Form 2 of the compound of Formula XI.

In a further aspect, the present invention provides compositions that inhibit MEK comprising one or more compounds of the present invention.

The invention also provides methods of making the compounds of the present invention.

In a further aspect the present invention provides a method of using the compounds of this invention as a medicament to treat diseases or medical conditions mediated by MEK. For example, this invention provides a compound of this invention as a medicament for treatment of a hyperproliferative disorder or an inflammatory condition in a mammal comprising administrating to said mammal one or more compounds of the present invention or a pharmaceutically acceptable salt or prodrug thereof in an amount effective to treat said hyperproliferative disorder. In another aspect this invention provides a compound of this invention in the manufacture of a medicament for the treatment of a hyperproliferative disorder or an inflammatory condition.

In a further aspect, the present invention provides a method of producing a producing a MEK inhibitory effect in a warm-blooded animal, such as man, in need of such treatment which comprises administering to said animal an effective amount of a compound of this invention.

In a further aspect the present invention provides treating or preventing an MEK-mediated condition, comprising administering to a human or animal in need thereof a pharmaceutical composition comprising a compound of the present invention or a pharmaceutically acceptable salt or in vivo cleavable prodrug thereof in an amount effective to treat or prevent said MEK-mediated condition.

The inventive compounds may further be used advantageously in combination with other known therapeutic agents.

The invention also relates to pharmaceutical compositions that inhibit MEK, comprising an effective amount of a compound selected from of the present invention or pharmaceutically acceptable prodrugs, pharmaceutically active metabolites, or pharmaceutically acceptable salts thereof.

An additional aspect of the invention is the use of a of the present invention in the preparation of a medicament for the treatment or prevention of a disease or medical condition mediated by MEK in a warm-blooded animal, preferably a mammal, more preferably a human, suffering from such disorder. More particularly, the invention includes the use of a compound of the invention in the preparation of a medicament for the treatment or prevention of a hyperproliferative disorder or an inflammatory condition in a mammal.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
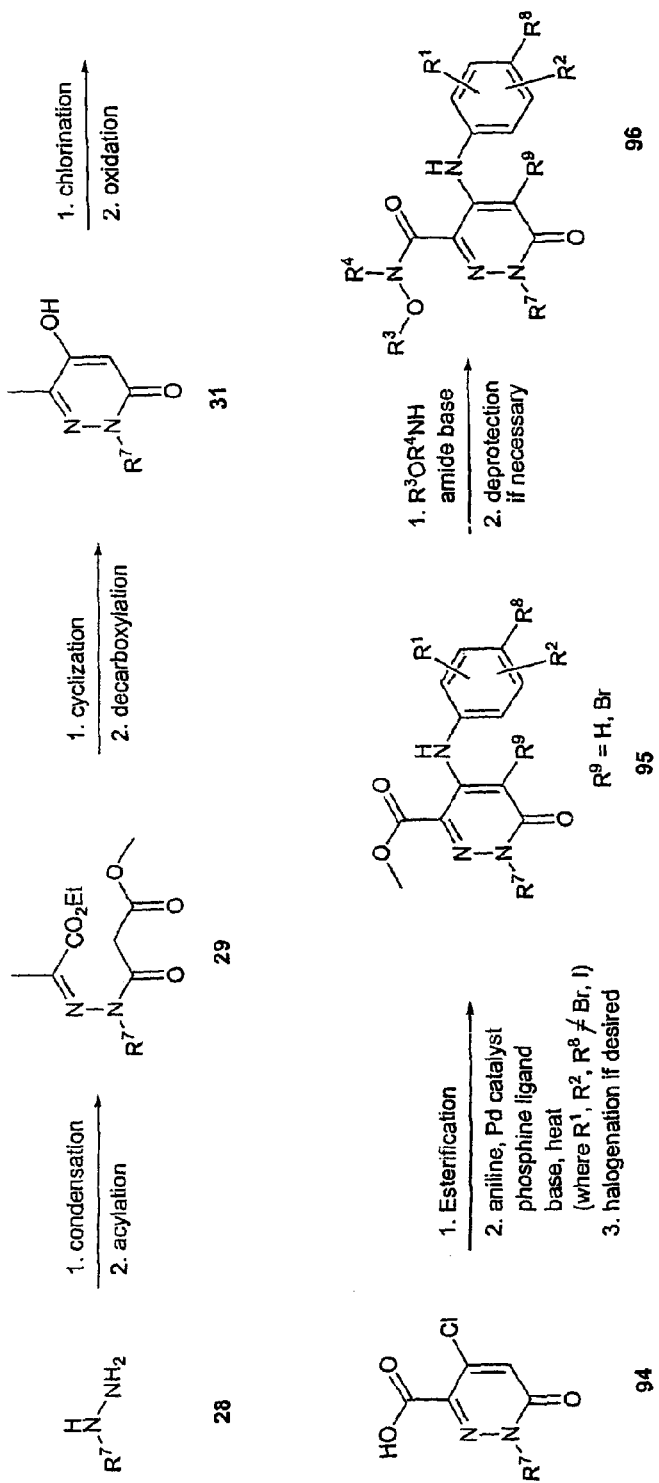
FIG. 1 shows a reaction scheme for the synthesis of compound 96.

The inventive compounds of the present invention and tautomers, metabolites, resolved enantiomers, diastereomers, solvates and pharmaceutically acceptable salts and prodrugs thereof are useful in the treatment of hyperproliferative diseases. In general, one aspect the present invention relates to compounds of the present invention that act as MEK inhibitors.

More specifically, one aspect of the present invention provides compounds including tautomers, metabolites, resolved enantiomers, diastereomers, solvates, and pharmaceutically acceptable salts thereof, said compound having the Formula I:

I wherein:

$R^1$ is Cl or F;

$R^3$ is H, Me, Et, OH, MeO-, EtO-, $HOCH_2CH_2O$—, $HOCH_2C(Me)_2O$—, (S)-$MeCH(OH)CH_2O$—, (R)—$HOCH_2CH(OH)CH_2O$—, cyclopropyl-$CH_2O$—, $HOCH_2CH_2$—, $R^7$ is cyclopropyl-$CH_2$— or $C_1$-$C_4$ alkyl, wherein said alkyl is optionally substituted with one or more F;

$R^8$ is Br, I or SMe; and $R^9$ is $CH_3$, $CH_2F$, $CHF_2$, $CF_3$, F or Cl.

In one embodiment the invention provides compounds, including tautomers, metabolites, resolved enantiomers, diastereomers, solvates, and pharmaceutically acceptable salts thereof, having the Formula IA:

IA wherein:

$R^1$ is Cl or F;

$R^3$ is H, Me, OH, MeO, EtO, $HOCH_2CH_2O$, $MeOCH_2CH_2O$, $HOCH_2CH_2CH_2$,

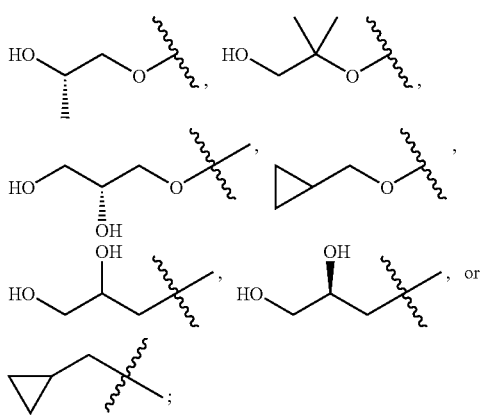

R[7] is cyclopropyl-CH$_2$— or C$_1$-C$_4$ alkyl, wherein said alkyl is optionally substituted with one or more F;
R[8] is Br, I or SMe; and
R[9] is CH$_3$, CH$_2$F, CHF$_2$, CF$_3$, F or Cl.

In one embodiment in the compounds of Formulae I or IA, R[7] is cyclopropyl-CH$_2$— or Me. In another embodiment, R[9] is CH$_3$, F or Cl.

In another embodiment there is a provided a compound of Formula II

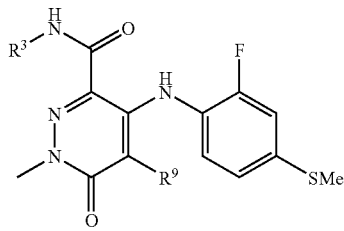

or a pharmaceutically acceptable salt thereof wherein:
R[3] is H, MeO, HOCH$_2$CH$_2$O, MeOCH$_2$CH$_2$O, HOCH$_2$CH$_2$CH$_2$,

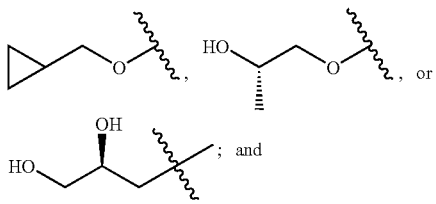

R[9] is H, CH$_3$, F or Cl.

Compounds of Formula II having a methyl substituent at the N1 position and specific R[3] and R[9] groups are potent MEK inhibitors.

Particular novel compounds of the invention include any one of the following:
4-(2-fluoro-4-(methylthio)phenylamino)-N-(2-hydroxyethoxy)-1-methyl-6-oxo-1,6-dihydropyridazine-3-carboxamide;
4-(2-fluoro-4-(methylthio)phenylamino)-N-(2-hydroxyethoxy)-1,5-dimethyl-6-oxo-1,6-dihydropyridazine-3-carboxamide;
N-(cyclopropylmethoxy)-4-(2-fluoro-4-(methylthio)phenylamino)-1,5-dimethyl-6-oxo-1,6-dihydropyridazine-3-carboxamide;
4-(2-fluoro-4-(methylthio)phenylamino)-N-(2-methoxyethoxy)-1,5-dimethyl-6-oxo-1,6-dihydropyridazine-3-carboxamide;
4-(2-fluoro-4-(methylthio)phenylamino)-N-methoxy-1,5-dimethyl-6-oxo-1,6-dihydropyridazine-3-carboxamide;
(S)-4-(2-fluoro-4-(methylthio)phenylamino)-N-(2-hydroxypropoxy)-1,5-dimethyl-6-oxo-1,6-dihydropyridazine-3-carboxamide;
4-(2-fluoro-4-(methylthio)phenylamino)-1,5-dimethyl-6-oxo-1,6-dihydropyridazine-3-carboxamide;
5-fluoro-4-(2-fluoro-4-(methylthio)phenylamino)-N-(2-hydroxyethoxy)-1-methyl-6-oxo-1,6-dihydropyridazine-3-carboxamide;
(S)-5-fluoro-4-(2-fluoro-4-(methylthio)phenylamino)-N-(2-hydroxypropoxy)-1-methyl-6-oxo-1,6-dihydropyridazine-3-carboxamide;
5-chloro-4-(2-fluoro-4-(methylthio)phenylamino)-N-(2-hydroxyethoxy)-1-methyl-6-oxo-1,6-dihydropyridazine-3-carboxamide;
(S)-5-chloro-4-(2-fluoro-4-(methylthio)phenylamino)-N-(2-hydroxypropoxy)-1-methyl-6-oxo-1,6-dihydropyridazine-3-carboxamide;
4-(2-fluoro-4-(methylthio)phenylamino)-N-(3-hydroxypropyl)-1,5-dimethyl-6-oxo-1,6-dihydropyridazine-3-carboxamide; and
(S)—N-(2,3-dihydroxypropyl)-4-(2-fluoro-4-(methylthio)phenylamino)-1,5-dimethyl-6-oxo-1,6-dihydropyridazine-3-carboxamide.

In another embodiment there is provided a compound of Formula III:

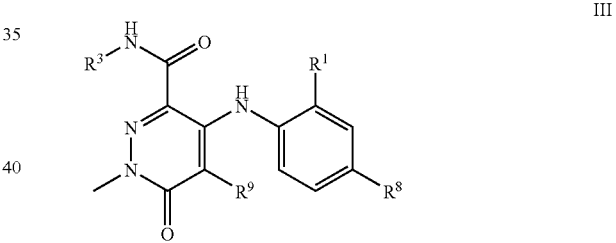

or a pharmaceutically acceptable salt thereof wherein:
R[1] is Cl or F;
R[3] is H, Me, MeO, HOCH$_2$CH$_2$O, HOCH$_2$CH$_2$CH$_2$, HOCH$_2$CH$_2$,

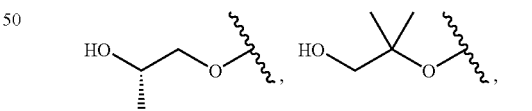
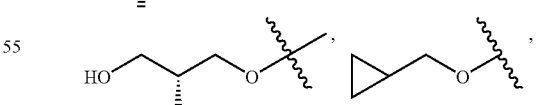
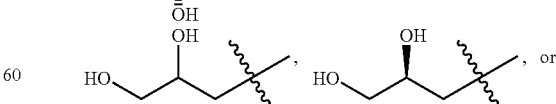
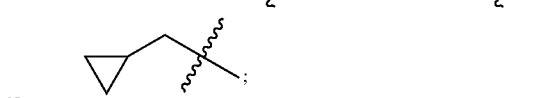

R[8] is Br or I; and
R[9] is CH$_3$, F, Cl or Br.

Compounds of Formula III where there is a methyl substituent at the N1 position and specific $R^1$, $R^3$, $R^8$ and $R^9$ groups are potent MEK inhibitors.

Particular novel compounds of the invention include any one of the following:

5-bromo-4-(4-bromo-2-fluorophenylamino)-N-(cyclopropylmethoxy)-1-methyl-6-oxo-1,6-dihydropyridazine-3-carboxamide;

4-(2-fluoro-4-iodophenylamino)-N-(2-hydroxyethoxy)-1,5-dimethyl-6-oxo-1,6-dihydropyridazine-3-carboxamide;

(R)—N-(2,3-Dihydroxypropoxy)-4-(2-fluoro-4-iodophenylamino)-1,5-dimethyl-6-oxo-1,6-dihydropyridazine-3-carboxamide;

4-(2-fluoro-4-iodophenylamino)-N-methoxy-1,5-dimethyl-6-oxo-1,6-dihydropyridazine-3-carboxamide;

N-(cyclopropylmethoxy)-4-(2-fluoro-4-iodophenylamino)-1,5-dimethyl-6-oxo-1,6-dihydropyridazine-3-carboxamide;

(S)-4-(2-fluoro-4-iodophenylamino)-N-(2-hydroxypropoxy)-1,5-dimethyl-6-oxo-1,6-dihydropyridazine-3-carboxamide;

4-(2-chloro-4-iodophenylamino)-N-(2-hydroxyethoxy)-1,5-dimethyl-6-oxo-1,6-dihydropyridazine-3-carboxamide;

(S)-4-(2-chloro-4-iodophenylamino)-N-(2-hydroxypropoxy)-1,5-dimethyl-6-oxo-1,6-dihydropyridazine-3-carboxamide;

4-(4-bromo-2-chlorophenylamino)-N-(2-hydroxyethoxy)-1,5-dimethyl-6-oxo-1,6-dihydropyridazine-3-carboxamide;

(S)-4-(4-bromo-2-chlorophenylamino)-N-(2-hydroxypropoxy)-1,5-dimethyl-6-oxo-1,6-dihydropyridazine-3-carboxamide;

4-(4-bromo-2-fluorophenylamino)-1,5-dimethyl-6-oxo-1,6-dihydropyridazine-3-carboxamide;

(R)-4-(4-bromo-2-fluorophenylamino)-N-(2,3-dihydroxypropoxy)-1,5-dimethyl-6-oxo-1,6-dihydropyridazine-3-carboxamide;

4-(4-bromo-2-fluorophenylamino)-N-(1-hydroxy-2-methylpropan-2-yloxy)-1,5-dimethyl-6-oxo-1,6-dihydropyridazine-3-carboxamide;

4-(2-fluoro-4-iodophenylamino)-1,5-dimethyl-6-oxo-1,6-dihydropyridazine-3-carboxamide;

4-(4-bromo-2-fluorophenylamino)-5-fluoro-N-(2-hydroxyethoxy)-1-methyl-6-oxo-1,6-dihydropyridazine-3-carboxamide;

4-(2-fluoro-4-iodophenylamino)-N,1,5-trimethyl-6-oxo-1,6-dihydropyridazine-3-carboxamide;

N-(cyclopropylmethyl)-4-(2-fluoro-4-iodophenylamino)-1,5-dimethyl-6-oxo-1,6-dihydropyridazine-3-carboxamide;

4-(2-fluoro-4-iodophenylamino)-N-(3-hydroxypropyl)-1,5-dimethyl-6-oxo-1,6-dihydropyridazine-3-carboxamide;

5-fluoro-4-(2-fluoro-4-iodophenylamino)-N-(2-hydroxyethoxy)-1-methyl-6-oxo-1,6-dihydropyridazine-3-carboxamide;

4-(2-fluoro-4-iodophenylamino)-N-(2-hydroxyethyl)-1,5-dimethyl-6-oxo-1,6-dihydropyridazine-3-carboxamide;

N-(2,3-dihydroxypropyl)-4-(2-fluoro-4-iodophenylamino)-1,5-dimethyl-6-oxo-1,6-dihydropyridazine-3-carboxamide;

5-chloro-4-(2-fluoro-4-iodophenylamino)-N-(2-hydroxyethoxy)-1-methyl-6-oxo-1,6-dihydropyridazine-3-carboxamide;

(S)-5-chloro-4-(2-fluoro-4-iodophenylamino)-N-(2-hydroxypropoxy) 1-methyl-6-oxo-1,6-dihydropyridazine-3-carboxamide;

5-chloro-4-(2-fluoro-4-iodophenylamino)-1-methyl-6-oxo-1,6-dihydropyridazine-3-carboxamide;

5-chloro-N-(2,3-dihydroxypropyl)-4-(2-fluoro-4-iodophenylamino)-1-methyl-6-oxo-1,6-dihydropyridazine-3-carboxamide;

(S)—N-(2,3-dihydroxypropyl)-4-(2-fluoro-4-iodophenylamino)-1,5-dimethyl-6-oxo-1,6-dihydropyridazine-3-carboxamide; and (S)-5-chloro-N-(2,3-dihydroxypropyl)-4-(2-fluoro-4-iodophenylamino)-1-methyl-6-oxo-1,6-dihydropyridazine-3-carboxamide.

Particular novel compounds of the invention also include the following compounds:

4-(4-bromo-2-fluorophenylamino)-N-(2-hydroxyethoxy)-1,5-dimethyl-6-oxo-1,6-dihydropyridazine-3-carboxamide; and (S)-4-(4-bromo-2-fluorophenylamino)-N-(2-hydroxypropoxy)-1,5-dimethyl-6-oxo-1,6-dihydropyridazine-3-carboxamide.

Yet another aspect of this invention provides compounds, including tautomers, metabolites, resolved enantiomers, diastereomers, solvates, and pharmaceutically acceptable salts thereof, said compound having the Formula IV:

IV wherein:

$R^1$ is Cl or F;

$R^3$ is H, Me, Et, OH, MeO-, EtO-, $HOCH_2CH_2O$—, $HOCH_2C(Me)_2O$—, $(S)-MeCH(OH)CH_2O$—, $(R)$—$HOCH_2CH(OH)CH_2O$—, cyclopropyl-$CH_2O$—, $HOCH_2CH_2$—, $R^7$ is methyl or ethyl, wherein said methyl and ethyl are optionally substituted with one or more F;

$R^8$ is Br, I or SMe; and $R^9$ is H, $C_1$-$C_4$ alkyl, Cl or CN, wherein said alkyl is optionally substituted with one or more groups independently selected from F or CN, provided that when:

a) $R^1$ is F, $R^8$ is Br, $R^9$ is H, and $R^7$ is either Me or Et, then $R^3$ cannot be $HOCH_2CH_2O$;

b) $R^1$ is F, $R^8$ is I, $R^9$ is H, and $R^3$ is MeO, then $R^7$ cannot be Me;

c) $R^1$ is F, $R^8$ is Me, $R^9$ is H, and $R^3$ is $HOCH_2CH_2O$, then $R^7$ cannot be Me: and d) $R^1$ is F, $R^8$ is Br, $R^9$ is H, and $R^3$ is cyclopropyl-$CH_2O$, then $R^7$ cannot be Me.

In one embodiment in the compounds of Formulae IV, $R^9$ is H, Me, Et, Cl or CN.

In one embodiment the compounds according to the invention have the Formula V:

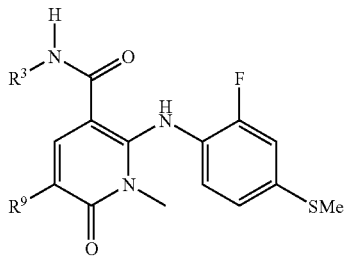

V or a pharmaceutically acceptable salt thereof wherein:
$R^3$ is $HOCH_2CH_2O$ or $(S)$-MeCH(OH)$CH_2O$; and
$R^9$ is H, $CH_3$, F or Cl, provided that when $R^1$ is F, $R^8$ is SMe, $R^9$ is Cl, and $R^7$ is Me, then $R^3$ cannot be $HOCH_2CH_2O$.

Compounds of Formula V where $R^3$ is $HOCH_2CH_2O$ or $(S)$-MeCH(OH)$CH_2O$ are potent MEK inhibitors.

Particular novel compounds of the invention include any one of the following:
2-(2-fluoro-4-(methylthio)phenylamino)-N-(2-hydroxyethoxy)-1-methyl-6-oxo-1,6-dihydropyridine-3-carboxamide;
(S)-2-(2-fluoro-4-(methylthio)phenylamino)-N-(2-hydroxypropoxy)-1-methyl-6-oxo-1,6-dihydropyridine-3-carboxamide;
2-(2-fluoro-4-(methylthio)phenylamino)-N-(2-hydroxyethoxy)-1,5-dimethyl-6-oxo-1,6-dihydropyridine-3-carboxamide;
(S)-2-(2-fluoro-4-(methylthio)phenylamino)-N-(2-hydroxypropoxy)-1,5-dimethyl-6-oxo-1,6-dihydropyridine-3-carboxamide;
5-fluoro-2-(2-fluoro-4-(methylthio)phenylamino)-N-(2-hydroxyethoxy)-1-methyl-6-oxo-1,6-dihydropyridine-3-carboxamide;
(S)-5-fluoro-2-(2-fluoro-4-(methylthio)phenylamino)-N-(2-hydroxypropoxy)-1-methyl-6-oxo-1,6-dihydropyridine-3-carboxamide; and
(S)-5-chloro-2-(2-fluoro-4-(methylthio)phenylamino)-N-(2-hydroxypropoxy)-1-methyl-6-oxo-1,6-dihydropyridine-3-carboxamide.

In one embodiment the compounds according to the invention have the Formula VI:

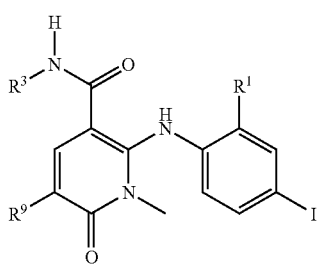

VI or a pharmaceutically acceptable salt thereof, wherein:
$R^1$ is Cl or F;
$R^3$ is H, $HOCH_2CH_2O$ or $(S)$-MeCH(OH)$CH_2O$; and
$R^9$ is H, Me, F or Cl.

Compounds of Formula VI wherein $R^1$ is Cl, $R^3$ is $HOCH_2CH_2O$ or $(S)$-MeCH(OH)$CH_2O$, and $R^9$ is H are potent MEK inhibitors.

Compounds of Formula VI wherein $R^1$ is F, $R^3$ is H and $R^9$ is Me are potent MEK inhibitors.

Compounds of Formula VI where $R^3$ is $HOCH_2CH_2O$, or $(S)$-MeCH(OH)$CH_2O$ are potent MEK inhibitors.

Compound of Formula VI wherein $R^1$ is F, $R^3$ is $HOCH_2CH_2O$, and $R^9$ is Me is a potent MEK inhibitor and also has good solubility. As used herein, the term "good solubility" refers to a compound that has a solubility of greater than 50 μg/mL, for example a solubility of about 50 to 270 μg/mL as determined by the method of Example C.

Particular novel compounds of Formula VI according to the invention include any one of the following:
2-(2-chloro-4-iodophenylamino)-N-(2-hydroxyethoxy)-1-methyl-6-oxo-1,6-dihydropyridine-3-carboxamide;
(S)-2-(2-chloro-4-iodophenylamino)-N-(2-hydroxypropoxy)-1-methyl-6-oxo-1,6-dihydropyridine-3-carboxamide;
2-(2-fluoro-4-iodophenylamino)-1,5-dimethyl-6-oxo-1,6-dihydropyridine-3-carboxamide;
2-(2-fluoro-4-iodophenylamino)-N-(2-hydroxyethoxy)-1-methyl-6-oxo-1,6-dihydropyridine-3-carboxamide;
(S)-2-(2-fluoro-4-iodophenylamino)-N-(2-hydroxypropoxy)-1-methyl-6-oxo-1,6-dihydropyridine-3-carboxamide;
(S)-2-(2-fluoro-4-iodophenylamino)-N-(2-hydroxypropoxy)-1,5-dimethyl-6-oxo-1,6-dihydropyridine-3-carboxamide;
2-(2-chloro-4-iodophenylamino)-N-(2-hydroxyethoxy)-1,5-dimethyl-6-oxo-1,6-dihydropyridine-3-carboxamide;
5-chloro-2-(2-fluoro-4-iodophenylamino)-N-(2-hydroxyethoxy)-1-methyl-6-oxo-1,6-dihydropyridine-3-carboxamide;
(S)-2-(2-chloro-4-iodophenylamino)-N-(2-hydroxypropoxy)-1,5-dimethyl-6-oxo-1,6-dihydropyridine-3-carboxamide;
(S)-5-chloro-2-(2-fluoro-4-iodophenylamino)-N-(2-hydroxypropoxy)-1-methyl-6-oxo-1,6-dihydropyridine-3-carboxamide;
5-fluoro-2-(2-fluoro-4-iodophenylamino)-N-(2-hydroxyethoxy)-1-methyl-6-oxo-1,6-dihydropyridine-3-carboxamide; and
(S)-5-fluoro-2-(2-fluoro-4-iodophenylamino)-N-(2-hydroxypropoxy)-1-methyl-6-oxo-1,6-dihydropyridine-3-carboxamide.

In another embodiment there is provided a compound of Formula VI where $R^1$ is F, $R^3$ is $HOCH_2CH_2O$, and $R^9$ is methyl, or a pharmaceutically acceptable salt thereof.

It was found that a compound of Formula XI

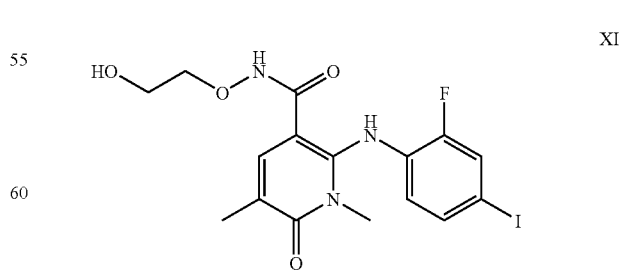

XI can exist in two crystalline forms, hereinafter designated as Form 1, 2-(2-fluoro-4-iodophenylamino)-N-(2-hydroxyethoxy)-1,5-dimethyl-6-oxo-1,6-dihydropyridine-3-carboxamide and Form 2, 2-(2-fluoro-4-iodophenylamino)-N-(2-hydroxyethoxy)-1,5-dimethyl-6-oxo-1,6-dihydropyridine-3-carboxamide and that Form 2 can be converted into Form 1.

Samples of the particular crystalline forms of the compound of Formula XI were analyzed using a combination of X-Ray Powder Diffraction analysis and Differential Scanning Calorimetry as described in Examples 16E and 16F.

Where it is stated that the present invention relates to a crystalline form of the compound of Formula XI, the degree of crystallinity as determined by X-ray powder diffraction data is conveniently greater than about 60%, more conveniently greater than about 80%, preferably greater than about 90% and more preferably greater than about 95%.

According to a further aspect of the invention there is provided a crystalline form of a compound of Formula XI substantially in the form of Form 2, 2-(2-fluoro-4-iodophenylamino)-N-(2-hydroxyethoxy)-1,5-dimethyl-6-oxo-1,6-dihydropyridine-3-carboxamide.

According to a further aspect of the invention there is provided a crystalline form of a compound of Formula XI substantially in the form of Form 1, 2-(2-fluoro-4-iodophenylamino)-N-(2-hydroxyethoxy)-1,5-dimethyl-6-oxo-1,6-dihydropyridine-3-carboxamide.

The compound of Formula XI in the form of Form 2, 2-(2-fluoro-4-iodophenylamino)-N-(2-hydroxyethoxy)-1,5-dimethyl-6-oxo-1,6-dihydropyridine-3-carboxamide has the X-ray diffraction pattern having characterizing peaks on the 2 theta (θ) scale at about 9.5 and 12.6. According to a further aspect of the invention there is provided the compound of Formula XI in the form of Form 2, 2-(2-fluoro-4-iodophenylamino)-N-(2-hydroxyethoxy)-1,5-dimethyl-6-oxo-1,6-dihydropyridine-3-carboxamide has the X-ray diffraction pattern having characterizing peaks on the 2 theta (θ) scale at about 9.5, 12.6, 14.7 and 19.6.

Figure 10:
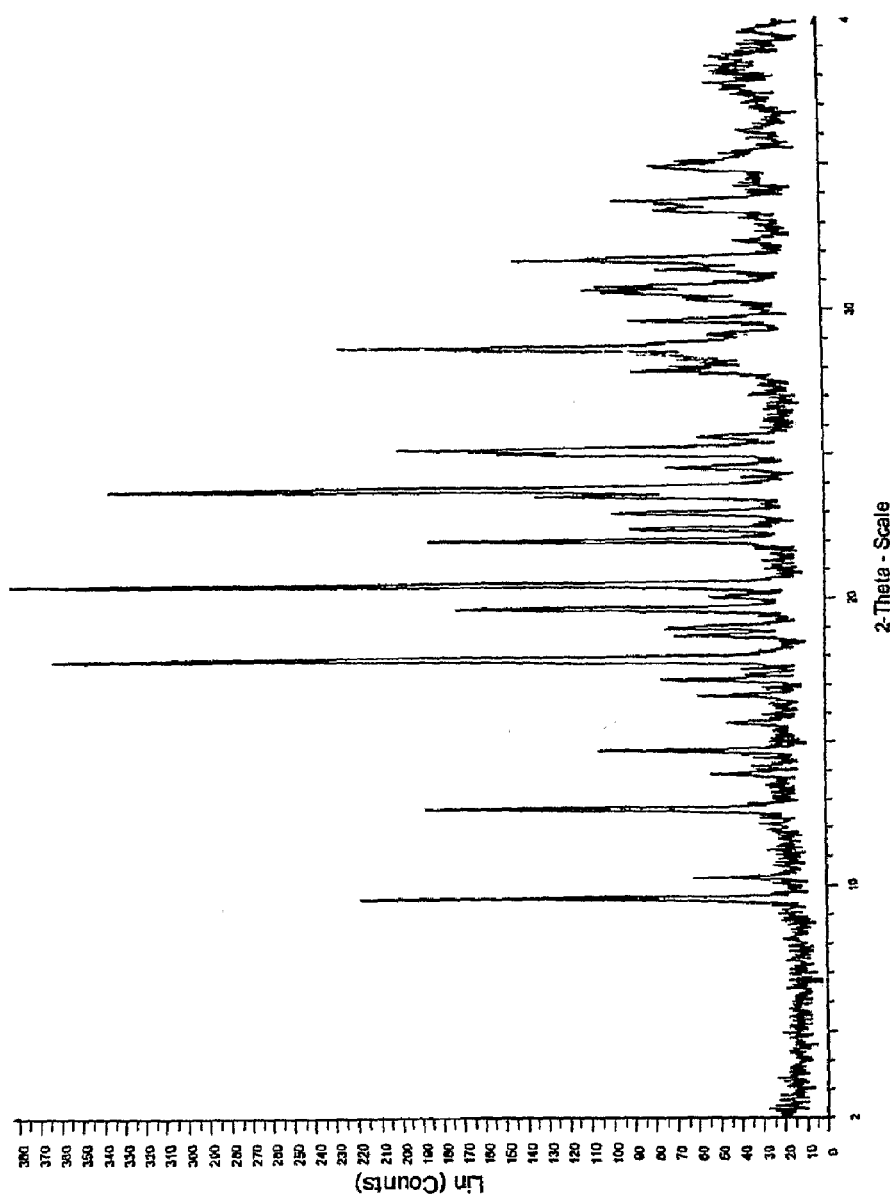
FIG. 10 shows the X-ray powder diffraction pattern for Form 2, 2-(2-fluoro-4-iodophenylamino)-N-(2-hydroxyethoxy)-1,5-dimethyl-6-oxo-1,6-dihydropyridine-3-carboxamide prepared according to Example 16A, Step 3.

The Form 2, 2-(2-fluoro-4-iodophenylamino)-N-(2-hydroxyethoxy)-1,5-dimethyl-6-oxo-1,6-dihydropyridine-3-carboxamide has the X-ray diffraction pattern substantially as shown in FIG. 10 hereinafter having characterizing peaks [on the 2 theta (θ) scale] at about the positions shown in Table A.

TABLE A

| Two theta | Relative Intensity |
|---|---|
| 9.54 | VS |
| 10.24 | S |
| 12.62 | VS |
| 13.86 | S |
| 14.67 | VS |
| 15.65 | S |
| 16.62 | S |
| 17.15 | S |
| 17.36 | S |
| 17.54 | S |
| 17.86 | VS |
| 18.72 | S |
| 19.00 | S |
| 19.63 | VS |
| 20.04 | S |
| 20.47 | VS |
| 22.02 | VS |
| 22.40 | S |
| 22.97 | VS |
| 23.54 | VS |
| 23.78 | VS |
| 24.54 | S |
| 25.13 | VS |
| 25.60 | S |
| 27.95 | S |
| 28.72 | VS |
| 29.19 | S |
| 29.67 | S |
| 30.40 | S |

TABLE A-continued

| Two theta | Relative Intensity |
|---|---|
| 30.65 | VS |
| 31.44 | S |
| 31.75 | VS |
| 32.39 | S |
| 33.48 | S |
| 33.77 | VS |
| 34.94 | S |
| 36.20 | S |
| 38.70 | S |
| 39.62 | M |

The compound of Formula XI in the form of Form 1, 2-(2-fluoro-4-iodophenylamino)-N-(2-hydroxyethoxy)-1,5-dimethyl-6-oxo-1,6-dihydropyridine-3-carboxamide has the X-ray diffraction pattern having characterizing peaks on the 2 theta (θ) scale at about 9.2 and 13.0. According to a further aspect of the invention there is provided the compound of Formula XI in the form of Form 1, 2-(2-fluoro-4-iodophenylamino)-N-(2-hydroxyethoxy)-1,5-dimethyl-6-oxo-1,6-dihydropyridine-3-carboxamide has the X-ray diffraction pattern having characterizing peaks on the 2 theta (θ) scale at about 9.2, 13.0, 18.3, 21.0 and 21.7.

Figure 11:
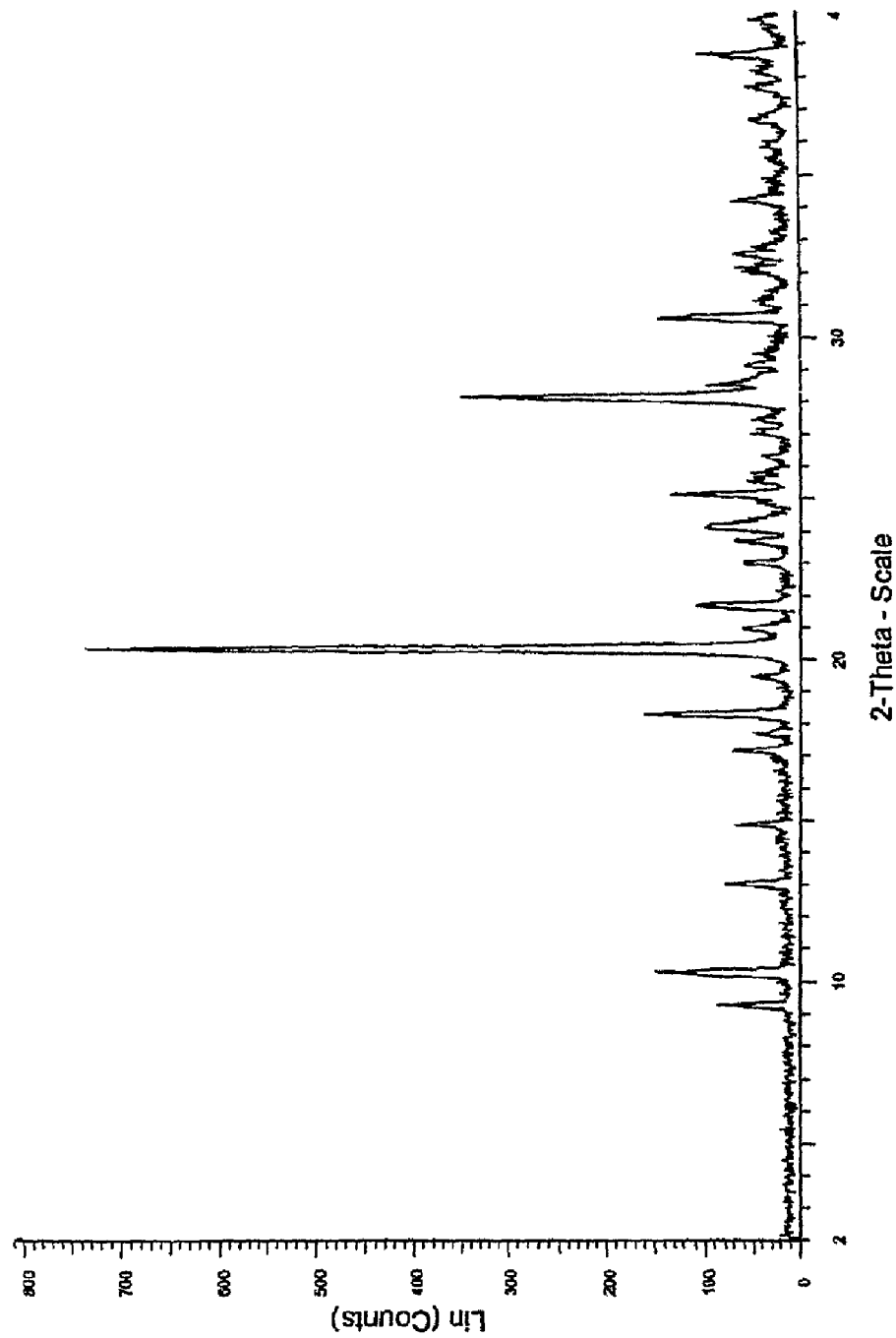
FIG. 11 shows the X-ray powder diffraction pattern for Form 1, 2-(2-fluoro-4-iodophenylamino)-N-(2-hydroxyethoxy)-1,5-dimethyl-6-oxo-1,6-dihydropyridine-3-carboxamide prepared according to Example 16A, Step 4.
Figure 12:
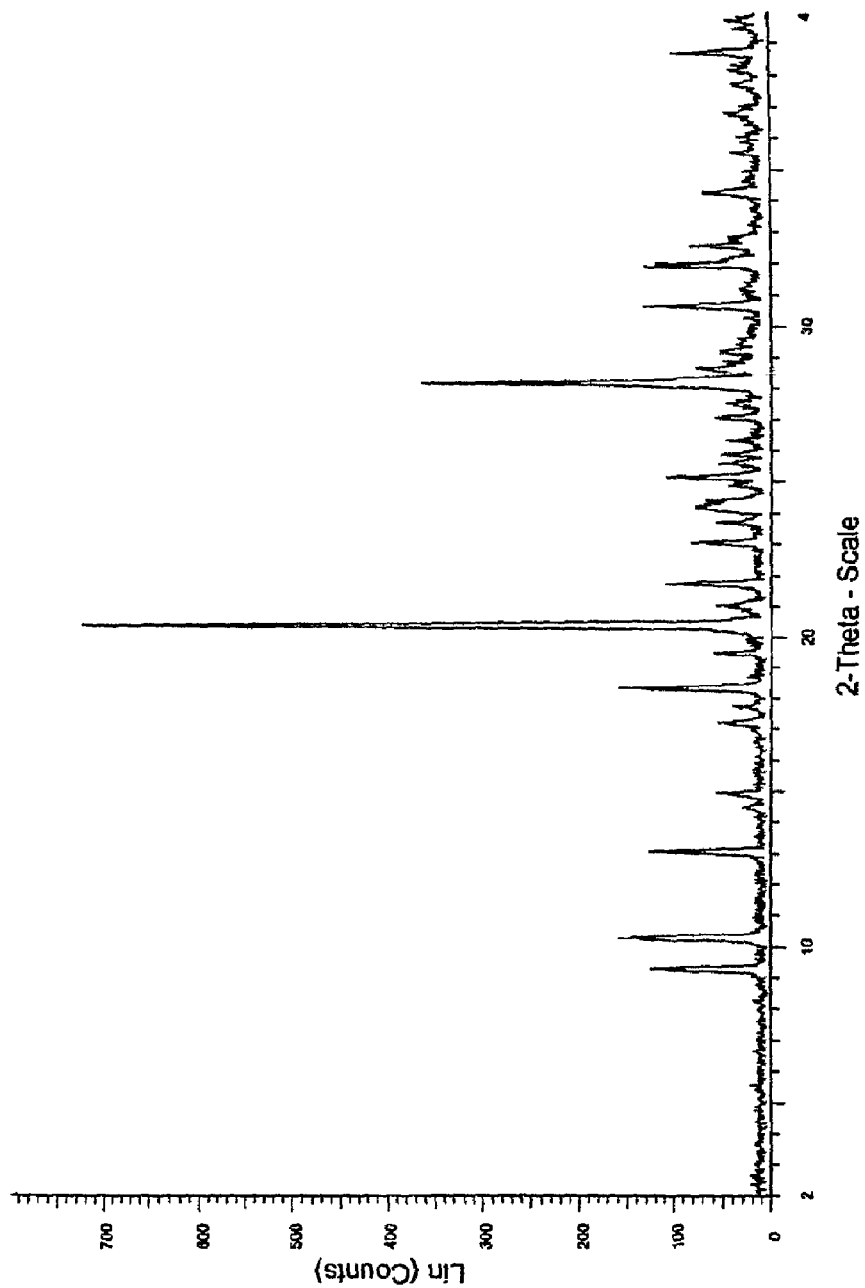
FIG. 12 shows the X-ray powder diffraction pattern for Form 1, 2-(2-fluoro-4-iodophenylamino)-N-(2-hydroxyethoxy)-1,5-dimethyl-6-oxo-1,6-dihydropyridine-3-carboxamide prepared according to Example 16B.

The Form 1, 2-(2-fluoro-4-iodophenylamino)-N-(2-hydroxyethoxy)-1,5-dimethyl-6-oxo-1,6-dihydropyridine-3-carboxamide has the X-ray diffraction pattern substantially as shown in FIG. 11 or 12 hereinafter having characterizing peaks [on the 2 theta (θ) scale] at about the positions shown in Table B.

TABLE B

| Two theta | Relative Intensity |
|---|---|
| 2.29 | M |
| 2.44 | M |
| 9.24 | S |
| 10.25 | S |
| 13.01 | S |
| 14.85 | M |
| 17.17 | M |
| 17.70 | M |
| 18.30 | S |
| 19.47 | M |
| 20.35 | VS |
| 20.98 | M |
| 21.69 | S |
| 22.14 | M |
| 23.02 | M |
| 23.70 | M |
| 24.15 | S |
| 25.15 | S |
| 25.58 | M |
| 25.86 | M |
| 26.32 | M |
| 27.08 | M |
| 27.49 | M |
| 28.17 | S |
| 28.61 | S |
| 29.20 | M |
| 30.65 | S |
| 32.15 | M |
| 32.61 | M |
| 34.26 | M |
| 34.90 | M |
| 35.51 | M |
| 35.94 | M |
| 36.74 | M |
| 37.71 | M |
| 38.20 | M |
| 38.71 | S |
| 39.78 | M |

As mentioned above, the intensities of the peaks in the XRPD diffractogram may exhibit some variability, depending upon the measurement conditions used. Accordingly, in Tables A and B and as quoted hereinafter, relative intensities are not stated numerically. Rather, the following definitions for intensity are used:

| % Relative Intensity | Definition |
| --- | --- |
| 25-100 | VS (very strong) |
| 10-25 | S (strong) |
| 3-10 | M (medium) |
| 1-3 | W (weak) | wherein the relative intensities are derived from X-ray diffraction patterns measured with variable slits.

Figure 13:
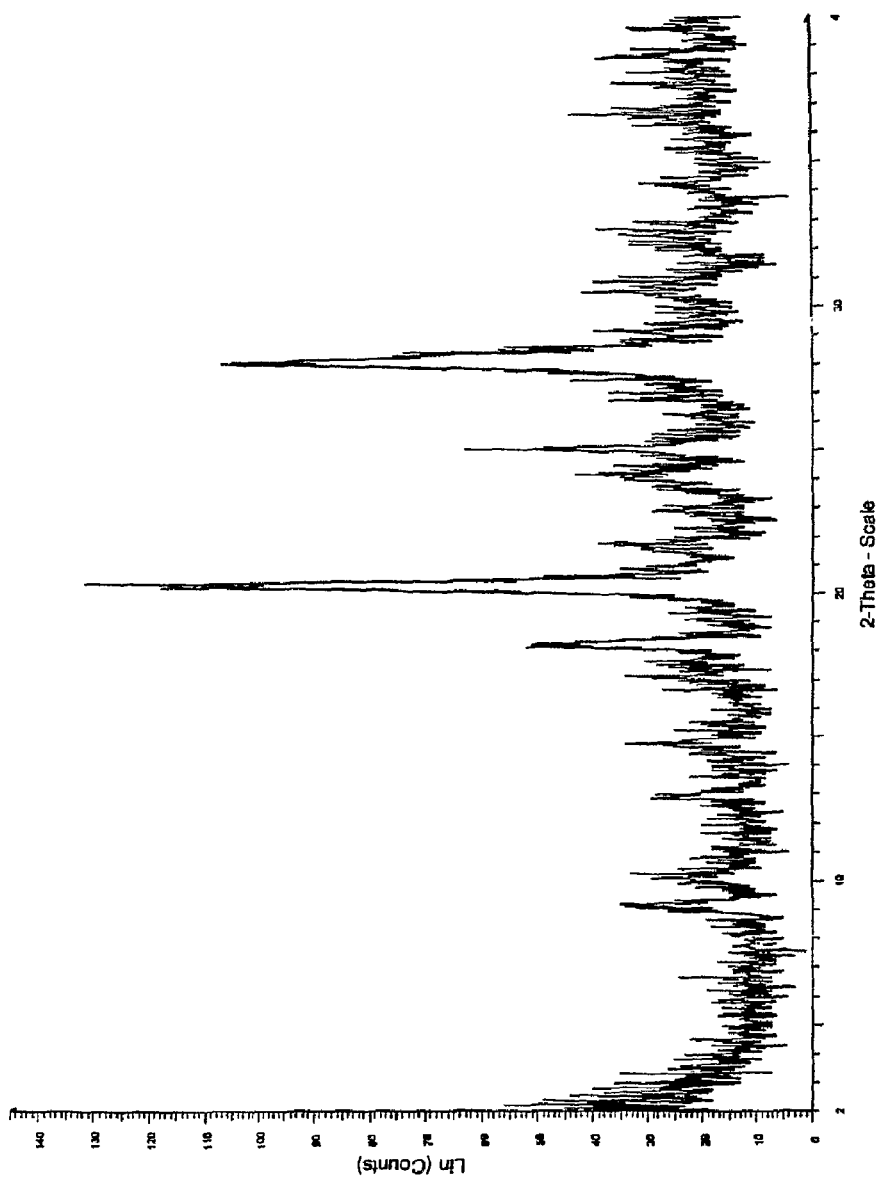
FIG. 13 shows the X-ray powder diffraction pattern for Form 1, 2-(2-fluoro-4-iodophenylamino)-N-(2-hydroxyethoxy)-1,5-dimethyl-6-oxo-1,6-dihydropyridine-3-carboxamide prepared according to Example 16D.

FIG. 13 shows the X-ray powder diffraction pattern for Form 1, 2-(2-fluoro-4-iodophenylamino)-N-(2-hydroxyethoxy)-1,5-dimethyl-6-oxo-1,6-dihydropyridine-3-carboxamide prepared according to Example 16D.

As will be clear, some of the more minor peaks present in the X-ray diffraction pattern in FIGS. 10 to 13 have been omitted from Tables A and B.

The compound of Formula XI in the form of Form 2, 2-(2-fluoro-4-iodophenylamino)-N-(2-hydroxyethoxy)-1,5-dimethyl-6-oxo-1,6-dihydropyridine-3-carboxamide has an X-ray diffraction pattern substantially as shown in FIG. 10.

The compound of Formula XI in the form of Form 1, 2-(2-fluoro-4-iodophenylamino)-N-(2-hydroxyethoxy)-1,5-dimethyl-6-oxo-1,6-dihydropyridine-3-carboxamide has an X-ray diffraction pattern substantially as shown in FIG. 11 or 12.

In the preceding paragraphs defining the X-ray powder diffraction peaks for the crystalline forms of 2-(2-fluoro-4-iodophenylamino)-N-(2-hydroxyethoxy)-1,5-dimethyl-6-oxo-1,6-dihydropyridine-3-carboxamide, the term "at about" is used in the expression " . . . on the 2 theta (θ) scale at about . . . " to indicate that the precise position of peaks (i.e. the recited 2-theta angle values) should not be construed as being absolute values because, as will be appreciated by those skilled in the art, the precise position of the peaks may vary slightly between one machine and another, from one sample to another, or as a result of slight variations in measurement conditions utilized. It is also stated in the preceding paragraphs that the crystalline forms of 2-(2-fluoro-4-iodophenylamino)-N-(2-hydroxyethoxy)-1,5-dimethyl-6-oxo-1,6-dihydropyridine-3-carboxamide provide X-ray powder diffraction patterns "substantially" the same as the X-ray powder diffraction patterns shown in FIGS. 10 to 13, and have substantially the most prominent peaks (2-theta angle values) shown in Tables A and B, respectively. It shall be appreciated that the use of the term "substantially" in this context is also intended to indicate that the 2-theta angle values of the X-ray powder diffraction patterns may vary slightly from one machine to another, from one sample to another, or as a result of slight variations in measurement conditions utilized, so the peak positions shown in the Figures or quoted in Tables A and B are again not to be construed as absolute values.

Processes for the preparation of a compound of Formula XI in either Form 1 or 2 are disclosed herein.

In one aspect the process for preparing a compound of Formula XI substantially in the form of Form 1, 2-(2-fluoro-4-iodophenylamino)-N-(2-hydroxyethoxy)-1,5-dimethyl-6-oxo-1,6-dihydropyridine-3-carboxamide which comprises:

a) contacting 2-(2-fluoro-4-iodophenylamino)-1,5-dimethyl-6-oxo-1,6-dihydropyridine-3-carboxylic acid (2-vinyloxyethoxy)-amide with an acidic mixture for a sufficient time to convert the compound into 2-(2-fluoro-4-iodophenylamino)-N-(2-hydroxyethoxy)-1,5-dimethyl-6-oxo-1,6-dihydropyridine-3-carboxamide;

b) allowing the material from step a) to crystallize from an organic solvent containing a seed of Form 1, 2-(2-fluoro-4-iodophenylamino)-N-(2-hydroxyethoxy)-1,5-dimethyl-6-oxo-1,6-dihydropyridine-3-carboxamide; and c) isolating the Form 1, 2-(2-fluoro-4-iodophenylamino)-N-(2-hydroxyethoxy)-1,5-dimethyl-6-oxo-1,6-dihydropyridine-3-carboxamide.

In one aspect the acidic mixture in step a) can be an inorganic or organic acid. In another aspect step a) can be carried out in a two phase aqueous acid-ethyl acetate solvent system. In one aspect, the organic solvent in step b) is ethyl acetate.

In another aspect the process for preparing a compound of Formula XI substantially in the form of Form 1, 2-(2-fluoro-4-iodophenylamino)-N-(2-hydroxyethoxy)-1,5-dimethyl-6-oxo-1,6-dihydropyridine-3-carboxamide which comprises:

a) agitating Form 2, 2-(2-fluoro-4-iodophenylamino)-N-(2-hydroxyethoxy)-1,5-dimethyl-6-oxo-1,6-dihydropyridine-3-carboxamide with a small quantity of Form 1, 2-(2-fluoro-4-iodophenylamino)-N-(2-hydroxyethoxy)-1,5-dimethyl-6-oxo-1,6-dihydropyridine-3-carboxamide in an organic solvent; and b) isolating the Form 1, 2-(2-fluoro-4-iodophenylamino)-N-(2-hydroxyethoxy)-1,5-dimethyl-6-oxo-1,6-dihydropyridine-3-carboxamide.

In one aspect the amount of Form 1 material used in step a) is about 5% w/w.

In another aspect step a) is carried out in ethyl acetate at a temperature slightly above ambient, such as from about 50 to 60° C.

In another aspect the invention provides a process for preparing a compound of Formula XI substantially in the form of Form 2, 2-(2-fluoro-4-iodophenylamino)-N-(2-hydroxyethoxy)-1,5-dimethyl-6-oxo-1,6-dihydropyridine-3-carboxamide according to claim 1 which comprises:

a) contacting 2-(2-fluoro-4-iodophenylamino)-1,5-dimethyl-6-oxo-1,6-dihydropyridine-3-carboxylic acid (2-vinyloxyethoxy)-amide with an acidic mixture for a sufficient time to convert the compound into 2-(2-fluoro-4-iodophenylamino)-N-(2-hydroxyethoxy)-1,5-dimethyl-6-oxo-1,6-dihydropyridine-3-carboxamide;

b) allowing the material from step a) to crystallize from an organic solvent and c) isolating the Form 2, 2-(2-fluoro-4-iodophenylamino)-N-(2-hydroxyethoxy)-1,5-dimethyl-6-oxo-1,6-dihydropyridine-3-carboxamide.

In one aspect the organic solvent in step b) contains a seed of Form 2, 2-(2-fluoro-4-iodophenylamino)-N-(2-hydroxyethoxy)-1,5-dimethyl-6-oxo-1,6-dihydropyridine-3-carboxamide. The acidic mixture in step a) can be an inorganic or organic acid and step a) may be carried out in an organic solvent such as THF. In one aspect the organic solvent in step b) may be selected from ethyl acetate and methyl isobutyl ketone, both optionally in the presence of isohexane.

Certain compounds of this invention can exist as two or more tautomeric forms. A "tautomer" is one of two or more structural isomers that exist in equilibrium and are readily converted from one isomeric form to another, such as structures formed by the movement of a hydrogen from one site to another within the same molecule. Other tautomeric forms of the compounds may interchange, for example, via enolization/de-enolization and the like. Accordingly, the present invention includes the preparation of all tautomeric forms of compounds of this invention.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and resolved enantiomers of the compounds of this invention. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

This invention also encompasses pharmaceutical compositions containing a compound of the present invention and methods of treating proliferative disorders, or abnormal cell growth, by administering compounds of the present invention. Compounds of the present invention having free amino, amido, hydroxy or carboxylic groups can be converted into pharmaceutically acceptable prodrugs.

A "prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One preferred prodrug of this invention is a compound of the present invention covalently joined to a valine residue.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group to a phosphate ester, hemisuccinates dimethylaminoacetate, or phosphoryloxymethyloxycarbonyl, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as $(C_1$-$C_6)$alkanoyloxymethyl, 1-$((C_1$-$C_6)$alkanoyloxy)ethyl, 1-methyl-1-$((C_1$-$C_6)$alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino$(C_1$-$C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$alkyl$)_2$ or glycosyl (the radical resulting from the removal of a hydroxyl group of the hemiacetal form of a carbohydrate).

Free amines can also be derivatized as amides, sulfonamides or phosphonamides. For example, a prodrug can be formed by the replacement of a hydrogen atom in the amine group with a group such as R-carbonyl, RO-carbonyl, NRR'-carbonyl where R and R' are each independently $(C_1$-$C_{10})$alkyl, $(C_3$-$C_7)$cycloalkyl, benzyl, or R-carbonyl is a natural α-aminoacyl or natural .alpha.-aminoacyl-natural α-aminoacyl, —C(OH)C(O)OY wherein $Y_1$ is H, $(C_1$-$C_6)$alkyl or benzyl, —C$(OY_0)Y_1$ wherein $Y_0$ is $(C_1$-$C_4)$ alkyl and $Y_1$ is $(C_1$-$C_6)$alkyl, carboxy$(C_1$-$C_6)$alkyl, amino$(C_1$-$C_4)$alkyl or mono-N— or di-N,N—$(C_1$-$C_6)$alkylaminoalkyl, —C$(Y_2)Y_3$ wherein $Y_2$ is H or methyl and $Y_3$ is mono-N— or di-N,N—$(C_1$-$C_6)$alkylamino, morpholino, piperidin-1-yl or pyrrolidin-1-yl.

All of these prodrug moieties may incorporate groups including but not limited to ether, amine and carboxylic acid functionalities.

Prodrugs of a compound of the present invention may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 *"Design and Application of Prodrugs,"* by H. Bundgaard p. 113-191 (1991); c) H. Bundgaard, *Advanced Drug Delivery Reviews*, 8, 1-38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

In addition, the invention also includes solvates, metabolites, and pharmaceutically acceptable salts of compounds of the present invention.

The term "solvate" refers to an aggregate of a molecule with one or more solvent molecules.

A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of compounds of the present invention, including compounds produced by a process comprising contacting a compound of this invention with a mammal for a period of time sufficient to yield a metabolic product thereof.

Metabolites are typically identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

A "pharmaceutically acceptable salt" as used herein, unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

Processes for the manufacture of the compounds of the present invention are provided as further features of the invention. The inventive compounds may be prepared using the reaction routes and synthesis schemes as described below, employing the techniques available in the art using starting materials that are readily available or can be synthesized using methods known in the art.

Illustrations of the preparation of compounds of the present invention are shown in FIGS. 1-7.

The preparation of compound 96 is depicted in FIG. 1. Substituted hydrazine 28 can be converted to hydrazono propanoate 29 by a two-step procedure. In the first step, hydrazine 28 is condensed with ethyl pyruvate under standard dehydrating conditions such as in the presence of $MgSO_4$ in a suitable organic solvent such as chloroform or methylene chloride at temperatures ranging from 0° C. to ambient. In the second step, acylation is achieved by treatment with base at low temperature in a suitable organic solvent such as THF, DMF, dioxane or MeCN, followed by the addition of methyl malonyl chloride. In one embodiment, the hydrazone is treated with LiH in THF at 0° C. followed by the addition of methyl malonyl chloride and warming to room temperature. Hydroxy pyridazinone 31 is prepared from hydrazono propanoate 29 by cyclization under strongly basic conditions followed by decarboxylation. The cyclization can be accomplished by treatment of hydrazono propanoate 29 with a strong base such as DBU, LDA or NaH in a suitable organic solvent such as THF or MeCN at room temperature. In one embodiment, cyclization is achieved with DBU in MeCN at room temperature. Decarboxylation to form hydroxypyridazinone 31 can be achieved by heating the methyl ester pyrazinone moiety in a suitable organic solvent such as dioxane or decalin or dioxane/decalin mixture to high temperatures in the presence of concentrated HCl. Carboxylic acid 94 can be prepared from hydroxy pyridazinone 31 in a two-step process, i.e., chlorination followed by oxidation. The chlorination step can be achieved by treatment with $POCl_3$, thionyl chloride, oxalyl chloride or $PCl_5$. In one embodiment, this transformation is achieved with $POCl_3$ neat at elevated temperature (~85° C.). Following the chlorination step, carboxylic acid 94 can be prepared by oxidation under standard conditions including but not limited to $KMnO_4$ in water, $SeO2$ in organic solvent such as dioxane, xylene, or pyridine, NaOCl/$RuCl_3$, $CrO_3$ in aqueous $H_2SO_4$, $K_2Cr_2O_7$, and $Na_2Cr_2O_7$ in water. In one embodiment this transformation is achieved with $K_2Cr_2O_7$—$H_2SO_4$. Carboxylic acid 94 can be converted to pyridazinone ester 95 in a two-step procedure which includes esterification of pyridazinone acid 94 followed by a palladium-mediated cross-coupling reaction. The esterification can be performed under standard conditions including, but not limited to, concentrated HCl in MeOH, TMSCl in MeOH or $TMSCHN_2$ in suitable organic solvents such as ether/MeOH, THF/MeOH or PhMe/MeOH. The palladium-mediated cross-coupling reaction can be achieved by standard methods including, but not limited to, treating the chloropyridazinone ester with an aniline, a palladium catalyst such as $Pd(OAc)_2$, $PdCl_2(dppf)$, $Pd(Ph_3P)_4$, or $Pd_2\,dba_3$, a phosphine ligand and a base in a suitable organic solvent such as THF, DMF, PhMe, DME or MeCN at elevated temperature. In one embodiment, the cross-coupling reaction comprises treating the ester 94 with $Pd(OAc)_2$, rac-2,2-bis(diphenylphosphino)-1,1'-binaphthyl and $Cs_2CO_3$ in toluene at 70 to 100° C. In embodiments of compound 95 where $R^9$=Br is desired, the bromine substituent can be incorporated after the cross-coupling reaction. Bromination of pyridazinone can be accomplished with NBS in a suitable organic solvent such as DMF, MeCN or mixed solvent systems at room temperature. In one embodiment the bromination is carried out in DMF. Hydroxamate 96 can be prepared by treating pyridazinone ester 95 with the appropriate hydroxylamine and amide base such as LDA, LiHMDS or NaHMDS in a suitable organic solvent such as THF at low temperature. In one embodiment, a LiHMDS solution is added to a solution of pyridazinone ester 95 and hydroxylamine in THF at 0° C. The reaction mixture is then warmed to room temperature to yield the desired hydroxamate 96. In some instances, the hydroxylamine used in the coupling reaction contains a standard protecting group. In those cases, the protecting group can be removed by standard conditions known in the art.

Figure 2:
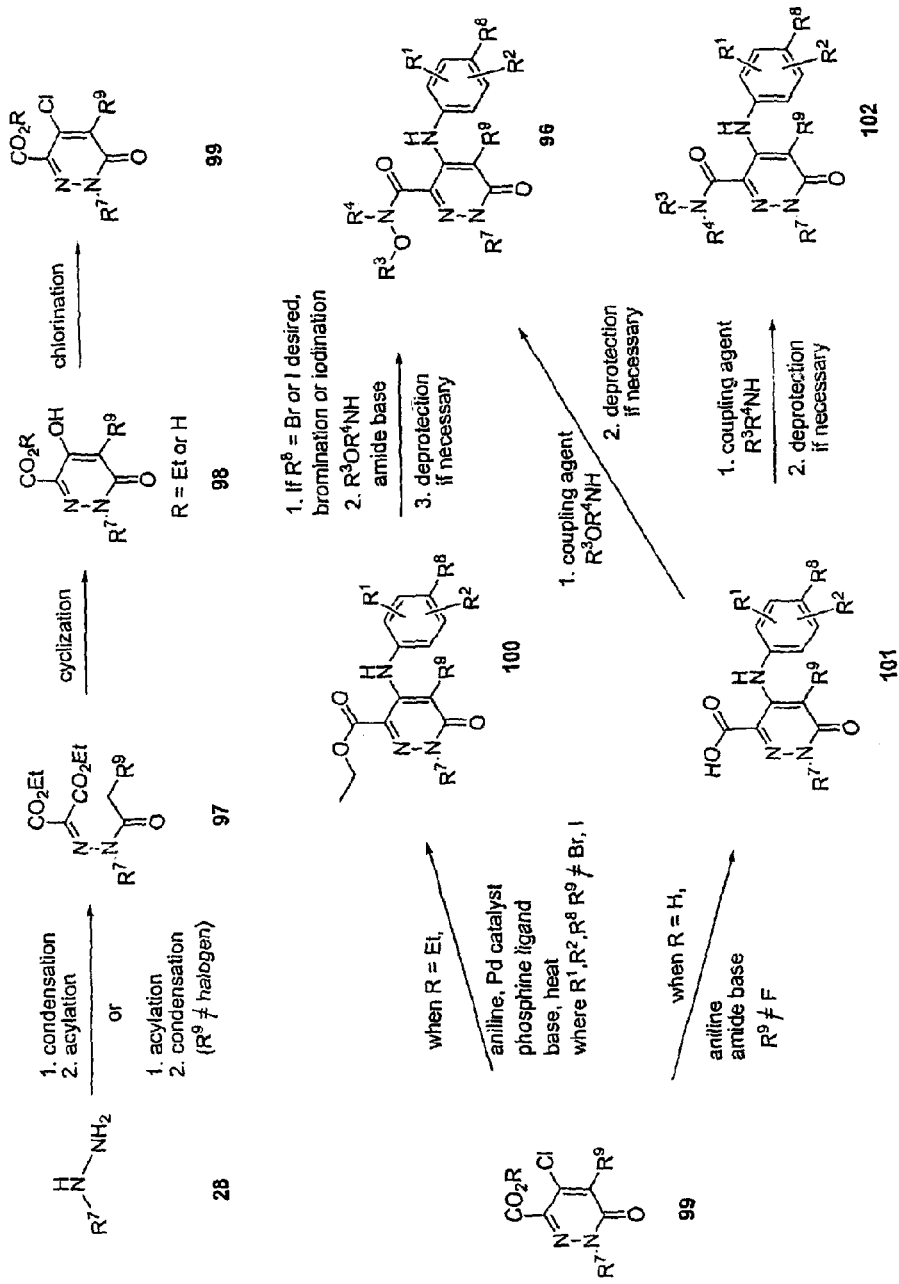
FIG. 2 shows a reaction scheme for the synthesis of compounds 96, 100, 101 and 102.

FIG. 2 outlines the synthesis of compounds 96, 100, 101 and 102. Substituted hydrazine 28 can be converted to hydrazono malonate 97 according to one of two procedures. In one embodiment, condensation of substituted hydrazine 28 followed by acylation is particularly useful for analogs where $R^9$ is alkyl or halogen. In this embodiment, hydrazine 28 can be condensed with diethyl 2-oxomalonate under standard dehydrating conditions using a Dean-Stark trap in a suitable organic solvent such as benzene or toluene at temperatures ranging from 80 to 120° C. Acylation with a reagent that delivers an acyl group to provide the hydrazono malonate 97 is achieved by treatment with base at the appropriate temperature in a suitable organic solvent such as THF, DMF, dioxane or MeCN followed by the addition of the acylating reagent. Examples of acylating reagents are well known to persons skilled in the art and include, but are not limited to, acid chlorides, acid anhydrides, and activated esters. In one embodiment, the hydrazone is treated with LiH in THF at 0° C. followed by the addition of an acid chloride and stirred at 25 to 60° C. to provide compound 97. An alternative method for synthesizing compound 97 wherein $R^9$ is not halogen involves acylating the hydrazine 28 with a reagent that delivers an acyl group, followed by condensation with diethyl 2-oxomalonate to provide the hydrazono malonate 97. According to this method, the substituted hydrazine 28 can be converted to the hydrazide by standard acylation methods. In one embodiment this transformation is achieved with the appropriate acid chloride in methylene chloride at 0° C. to ambient temperature. The hydrazide obtained is condensed with diethyl ketomalonate under standard dehydrating conditions using a Dean-Stark trap in a suitable organic solvent such as benzene or toluene at temperature from 80 to 130° C. Pyridazinone 99 is prepared from hydrazono malonate 97 by cyclization under basic conditions to provide the intermediated acid or ester 98, followed by chlorination to provide the pyridazinone 99. The cyclization can be accomplished by treatment of hydrazono malonate 7 with an amide base such as LiHMDS, NaHMDS, KHMDS or LDA in a suitable organic solvent such as THF or ether at low temperature. In one embodiment, cyclization is achieved with LiHMDS in THF at low temperature (−78 to −40° C.), followed by treatment with concentrated HCl to yield the ester derivative of 98 (R=Et). In another embodiment, the acid derivative of 98 (R=H) is obtained by in-situ saponification of the pyridazinone ester 98. Upon completion of cyclization, the reaction mixture is quenched with water at low temperatures (−78 to 40° C.), then warmed to ambient temperature with stirring followed by acidification. Pyridazinone 99 is then prepared from pyridazinone acid or ester 98 by treatment with $POCl_3$, thionyl chloride, oxalyl chloride or $PCl_5$. In one embodiment this transformation is achieved with $POCl_3$ neat at elevated temperature (~85° C.). When $R^9$ is not F, pyridazinone acid 99 (when R=H) can then be converted to pyridazinone 101. Incorporation of the aniline moiety is accomplished by an $S_NAr$ reaction in a suitable organic solvent such as THF using an amide base such as LDA, LiHMDS, NaHMDS or KHMDS at appropriate temperatures (−78° C. to room temperature). In one embodiment, the aniline is added to LDA or LiHMDS in THF at low temperature (−20 to −80° C.). The pyridazinone acid 99 (R=H) is then added and the reaction mixture is warmed to room temperature to generate carboxylic acid 101. Hydroxamates 96 and amides 102 can then be prepared from acid 101 using a standard coupling reagent such as, but not limited to, 1-(3-dimethylaminopropyl)-3-ethylcarbodiimide hydrochloride (EDCI), 1-hydroxybenzotriazole-6-sulfonamidomethyl hydrochloride (HOBt), or benzotriazol-1-yl-oxytripyrrolidinophosphonium hexafluorophosphate (PyBOP), and the appropriate amine or hydroxylamine in a suitable organic solvent such as DMF, THF or methylene chloride. In some instances, the amine or hydroxylamine contains a standard protecting group. In those cases, the protecting group can be removed by standard conditions known in the art.

Alternatively, ester pyridazinone 99 (R=Et) can be converted to hydroxamate 96 through pyridazinone ester 100 by the standard methods described in FIG. 1. When $R^8$=Br or I is desired, the desired halogen can be incorporated using NBS or NIS in a suitable organic solvent or mixed solvent system such as DMF, THF-MeOH, or AcOH-THF in the presence of an appropriate acid catalyst.

Figure 3:
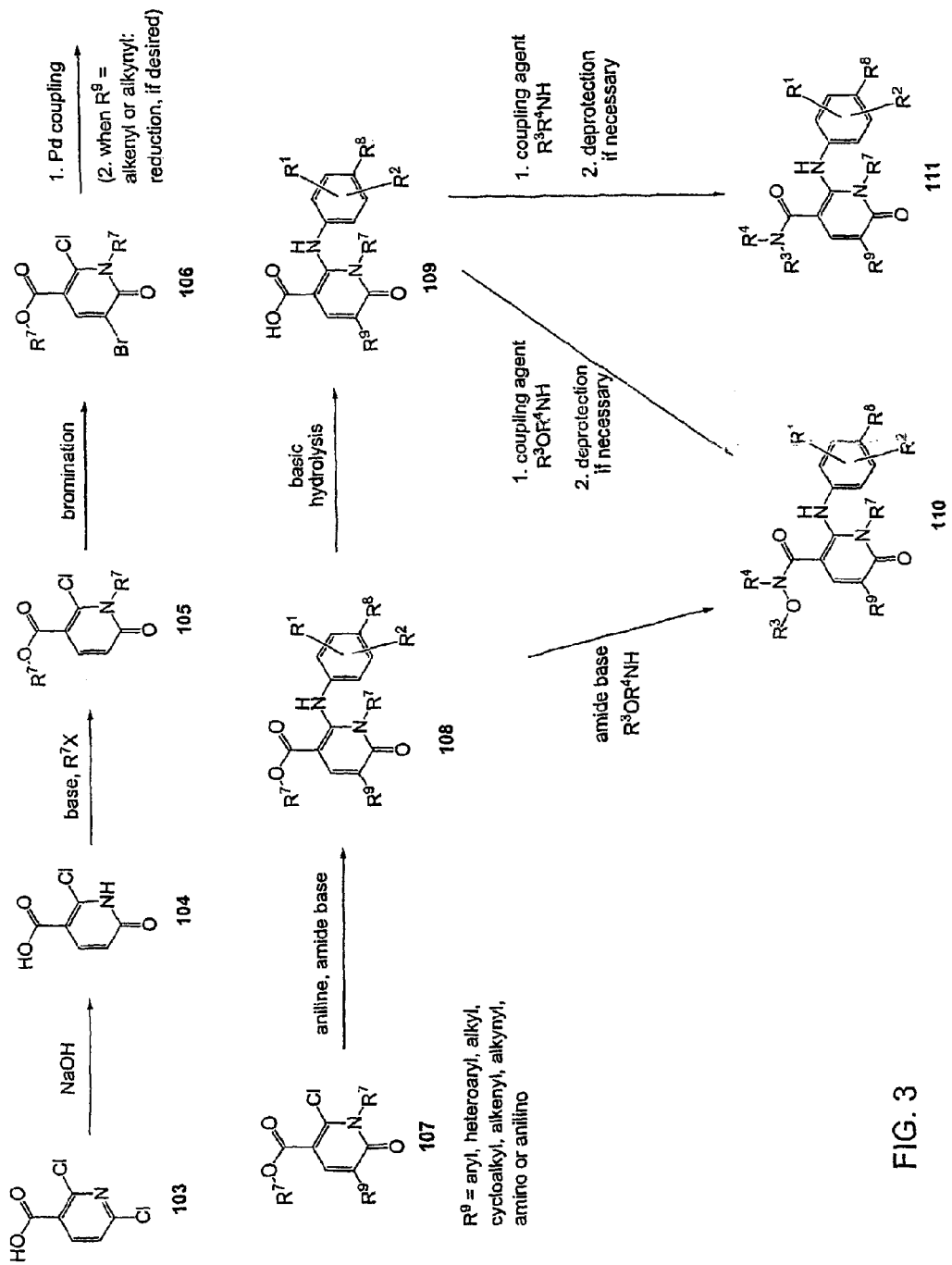
FIG. 3 shows a reaction scheme for the synthesis of compounds 109, 110 and 111.

In FIG. 3, the synthesis of compounds 109, 110 and 111 wherein 2,6-dichloronicotinic acid is used as the starting material. The nicotinic acid 103 is converted to the monochloro acid 104 by refluxing in 2 N aqueous NaOH following the procedure described in U.S. Pat. No. 3,682,932. Alkylation of 104 to provide 105 can be achieved by standard basic alkylation conditions incorporating alkyl halides, with two equivalents of the appropriate alkyl halide and base to give a mixture of the N-alkyl pyridone ester 105 and the regioisomeric O-alkyl pyridine ester, which are easily separated by column chromatography. These conditions include, but are not limited to, $K_2CO_3$ in acetone or DMF at room or elevated temperature or NaH in THF at ambient or elevated temperature and then addition of the alkyl halide. In certain embodiments this alkylation is achieved with LiH in DMF at 0° C., followed by addition of alkyl bromide or alkyl iodide and warning to room temperature. Bromination of pyridone ester 105 can be accomplished with either $Br_2$ and acetic acid or NBS in a suitable organic solvent such as DMF. In certain embodiments NBS is added to a solution of pyridone ester 105 in DMF to yield 106. Conversion of bromide 106 to compound 107 can be achieved using Pd mediated cross coupling conditions. When $R^9$=alkenyl or alkynyl, these can be further reduced using the appropriate reducing agent to provide alkyl substituents at $R^9$. In general, this chemistry can be accomplished using a wide variety of Pd catalysts and ligands, with or without added base, in a suitable organic solvent such as DMF, PhMe, DME, THF, $CH_3CN$ at elevated temperature. The coupling partner will depend on the nature of $R^9$. For example, if $R^9$=CN is desired, the coupling partner is $Zn(CN)_2$. This reaction can be carried out with $Pd_2$ $dba_3$ and dppf in NMP at 120° C. These palladium-mediated cross couplings are well documented in the literature and are well known to one skilled in the art. Incorporation of the properly substituted aniline moiety to provide 108 is accomplished by $S_NAR$ reaction. This can be done in a suitable organic solvent such as THF using an amide base such as LDA, LiHMDS, NaHMDS, or KHMDS at appropriate temperatures (−78° C. to room temperature). In certain embodiments the aniline is added to LDA or LiHMDS in THF at low temperature (−20 to −80° C.). The pyridone 105 is then added and the mixture is stirred at low temperature to generate ester 108. Carboxylic acid 109 can then be prepared using standard saponification conditions such as LiOH or NaOH in standard mixed aqueous/organic solvent systems. Hydroxamate 110 and amide 111 can be prepared using standard coupling procedures, including but not limited to EDCI, HOBt, or PyBOP and the appropriate amine or hydroxylamine in suitable organic solvents such as DMF, THF, or methylene chloride. In certain embodiments, the coupling is accomplished with HOBt and EDCI in DMF. In some instances, the amine or hydroxylamine used in the coupling reaction contains a standard protecting group. In those cases, the protecting group can be removed by standard conditions known in the art.

Figure 4:
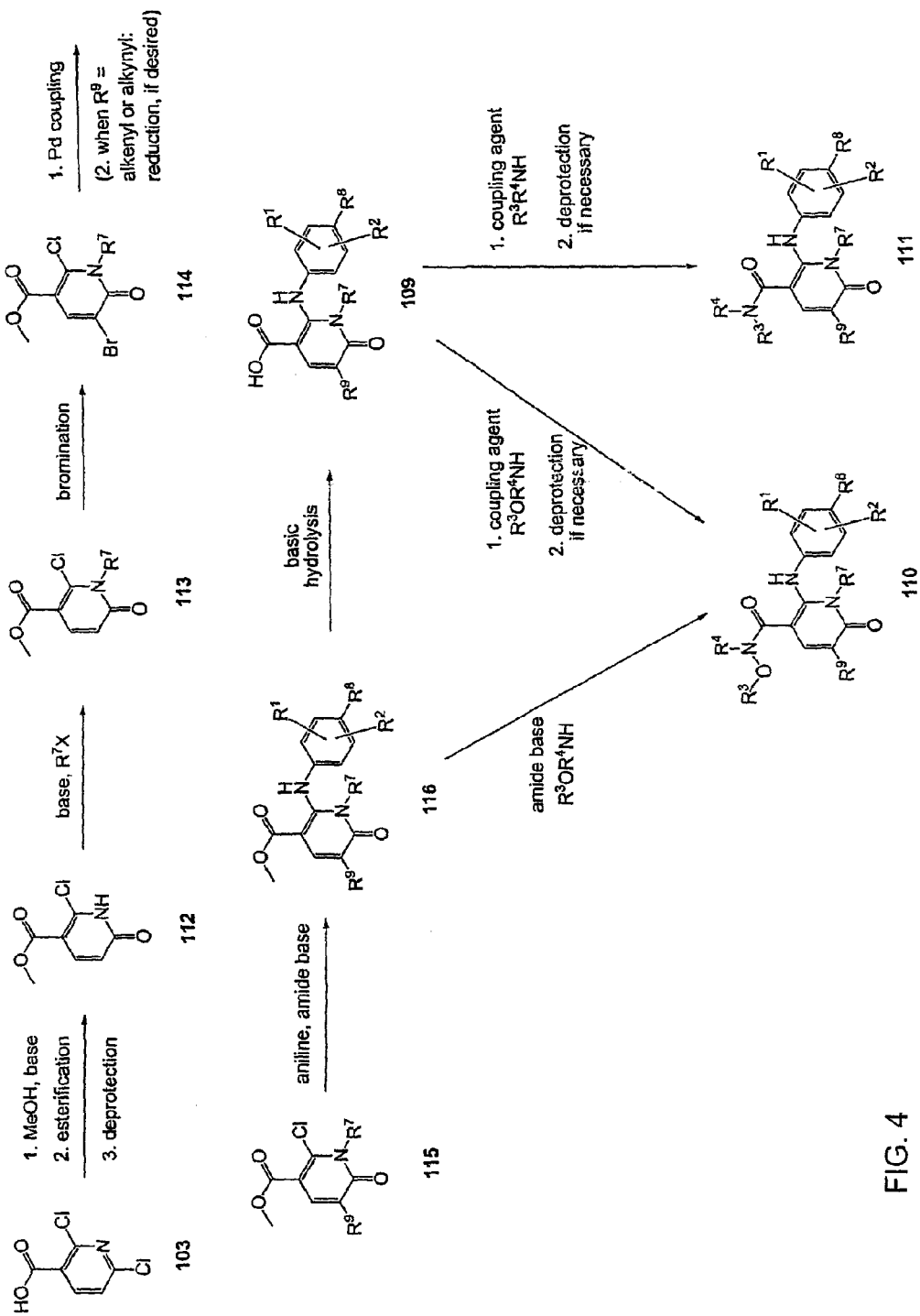
FIG. 4 shows an alternate reaction scheme for the synthesis of compounds 109, 110 and 111.

FIG. 4 shows an alternate reaction scheme for the synthesis of compounds 109, 110 and 111. This route is particularly useful for analogs where $R^7$ is not equal to Me or Et. Nicotinic acid 103 can be converted to the N-alkyl pyridone methyl ester 114 following a seven step procedure, where 2,6-dichloro-nicotinic acid 103 is first converted to the methoxy pyridine acid, which is esterified to give the methyl ester and then deprotected to yield the mono chloro ester 112. In certain embodiments the conversion to the methoxy pyridine acid is carried out by adding potassium t-butoxide to a solution of the acid 103 in MeOH and this mixture is then heated to reflux for several days. Esterification to give the methyl ester can be carried out under standard conditions, including but not limited to Fisher esterification (MeOH, $H_2SO_4$), TMSCl in MeOH or $TMSCHN_2$ in suitable organic solvents such as PhMe/MeOH. Demethylation of the methoxy pyridine can then be accomplished by standard conditions including but not limited to HCl at elevated temperature, pTsOH in acetic acid at elevated temperature and aqueous HBr in MeOH at elevated temperature. Preferable demethylation to give pyridone 112 is achieved by treatment of the methoxy pyridine with aqueous HBr in acetic acid at elevated temperature (80 to 120° C.). Alkylation of 112 can be achieved by standard basic alkylation conditions incorporating alkyl halides, with one equivalent of the appropriate alkyl halide and base to give a mixture of the N-alkyl pyridone ester 113 and the regioisomeric O-alkyl pyridine ester, which are easily separated by column chromatography. These conditions include but are not limited to $K_2CO_3$ in acetone or DMF at room or elevated temperature or NaH in THF at ambient or elevated temperature and then addition of the alkyl halide. In certain embodiments this alkylation is achieved with LiH in DMF at 0° C., followed by addition of alkyl bromide or alkyl iodide and warming to room temperature. Bromination of pyridone ester 113 can be accomplished with either $Br_2$ and acetic acid or NBS in a suitable organic solvent such as DMF. In certain embodiments NBS is added to a solution of pyridone ester 113 in DMF to yield 114. Conversion of bromide 114 to compound 115 can be achieved using palladium-mediated cross-coupling conditions. When $R^9$=alkenyl or alkynyl, these can be further reduced using the appropriate reducing agent to provide alkyl substituents at $R^9$. In general, this chemistry can be accomplished using a wide variety of Pd catalysts and ligands, with or without added base, in a suitable organic solvent such as DMF, PhMe, DME, THF, $CH_3CN$ at elevated temperature. The coupling partner will depend on the nature of $R^9$. These Pd mediated cross-couplings are well documented in the literature and are well known to one skilled in the art. Incorporation of the properly substituted aniline moiety to provide 116 is accomplished by $S_NAR$ reaction. This can be done in a suitable organic solvent such as THF using an amide base such as LDA, LiHMDS, NaHMDS, or KHMDS at appropriate temperatures (−78° C. to room temperature). In certain embodiments the aniline is added to LDA or LiHMDS in THF at low temperature (−20 to −80° C.). The pyridone 115 is then added and the mixture is stirred at low temperature to generate ester 116. Conversion of 116 to carboxylic acid 109, as well as hydroxamate 110 and amide 111 can be accomplished as described for FIG. 3. Alternatively, hydroxamate 110 can be prepared directly from methyl ester 116 in a suitable organic solvent such as THF using the appropriate hydroxylamine and amide base such as LDA, LiHMDS, NaHMDS, or KHMDS at appropriate temperatures (−78° C. to room temperature). In certain embodiments, a solution of LiHMDS is added to a solution of the ester 116 and the hydroxylamine in THF at 0° C. The reaction mixture is then warmed to room temperature to yield the desired hydroxamate 110. In some instances, the hydroxylamine used in the coupling reaction contains a standard protecting group. In those cases, the protecting group can be removed by standard conditions known in the art.

Figure 5:
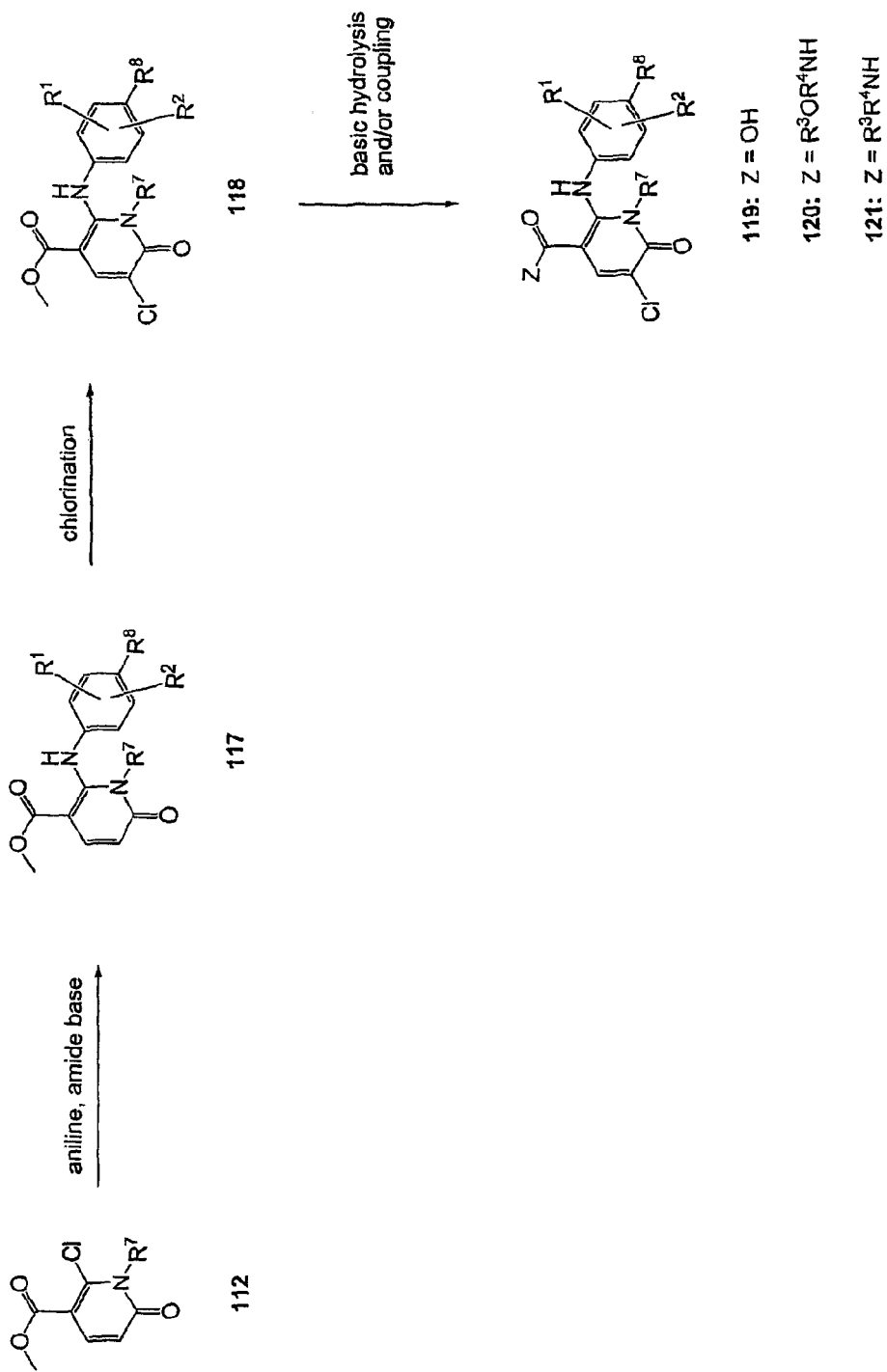
FIG. 5 shows a reaction scheme for the synthesis of compounds 119, 120 and 121.

FIG. 5 shows a reaction scheme for the synthesis of compounds 119, 120 and 121, wherein N-alkyl pyridone methyl ester 112 is used as the starting material. Formation of 117 can be accomplished by incorporation of the properly substituted aniline moiety by $S_NAR$ reaction. This can be done in a suitable organic solvent such as THF using an amide base such as LDA, LiHMDS, NaHMDS, or KHMDS at appropriate temperatures (−78° C. to room temperature). In certain embodiments the aniline is added to LDA or LiHMDS in THF at low temperature (−20 to −80° C.). The pyridone 112 is then added and the mixture is stirred at low temperature to generate ester 117. This can be done in a suitable organic solvent such as THF using an amide base such as LDA, LiHMDS, NaHMDS, or KHMDS at appropriate temperatures (−78° C. to room temperature). Chlorination of pyridone 117 to give pyridone 118 can be accomplished using standard conditions such as NCS in a suitable organic solvent, such as DMF. Conversion of 118 to carboxylic acid 119, as well as hydroxamate 120 and amide 121 can be accomplished as described for FIGS. 3 and 4.

Figure 6:
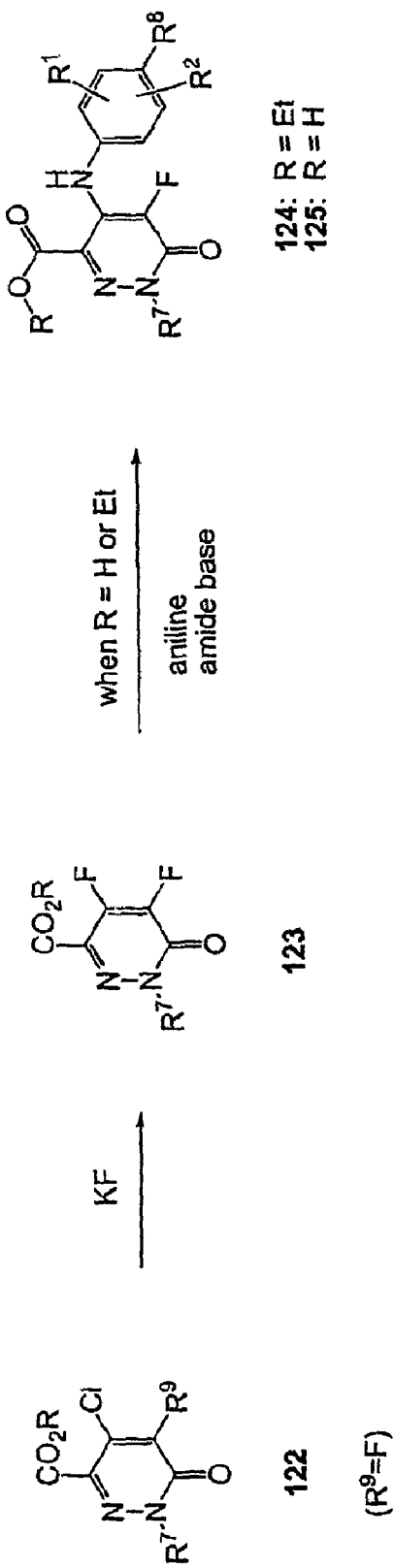
FIG. 6 shows a reaction scheme for the synthesis of compounds 124 and 125.

FIG. 6 shows a reaction scheme for the synthesis of compounds 124 and 125. 4-Fluoropyridazinone 123 can be prepared from 4-chloropyridazinone 122 by treatment with KF or HF with or without base such as $Et_3N$ or $Me_3N$ in suitable organic solvents such as $CH_3CN$, THF, DMF, NMP or DMSO. In one embodiment, this transformation is achieved with KF in DMSO at elevated temperature (e.g., 160° C.). Pyridazinone ester 123 (when R=Et) can be converted to pyridazinone 124, wherein incorporation of the aniline moiety is accomplished by SnAr reaction. This can be done in a suitable organic solvent such as DMF, EtOH, iPrOH, $CH_3CN$ or THF using a base such as $Cs_2CO_3$, $NaHCO_3$, $K_2CO_3$ or $Na_2CO_3$ at temperature from 80 to 160° C. In one embodiment, the aniline and $Cs_2CO_3$ are added to a solution of pyridazinone 123 in DMF and the reaction mixture is heated to 80° C. Alternatively, pyridazinone acid 123 (R=H) can be converted to pyridazinone 125 by standard methods such as those described in FIG. 2. Pyridazinone 124 or 125 can be converted to hydroxamates or amides as described in FIG. 1 or 2.

Figure 7:
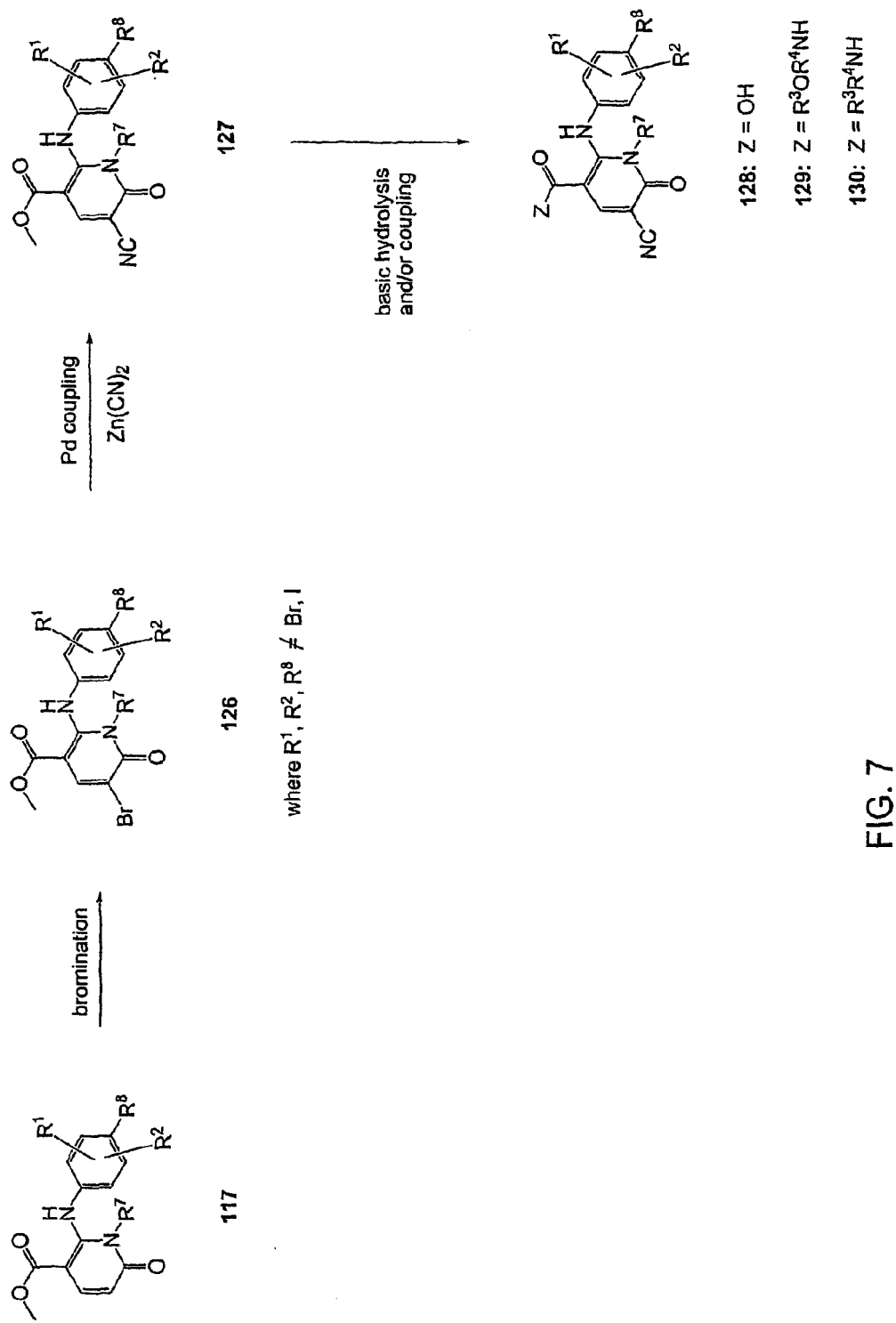
FIG. 7 shows a reaction scheme for the synthesis of compounds 128, 129 and 130.

FIG. 7 shows a reaction scheme for the synthesis of compounds 128, 129 and 130, wherein pyridone methyl ester 117 is used as the starting material. Bromination of pyridone ester 117 can be accomplished with either $Br_2$ and acetic acid or NBS in a suitable organic solvent such as DMF. Preferably NBS is added to a solution of pyridone ester 117 in DMF to yield 126. Conversion of bromide 126 to compound 127 where $R^9$ is cyano can be achieved using Pd mediated cross coupling conditions. In general, this chemistry can be accomplished using a wide variety of Pd catalysts and ligands, with or without added base, in a suitable organic solvent such as DMF, PhMe, DME, THF, $CH_3CN$ or NMP at elevated temperature. Preferably, this reaction is carried out with $Zn(CN)_2$ and $Pd_2$ $dba_3$ and dppf in DMF at 120° C. Conversion of 127 to carboxylic acid 128, as well as hydroxamate 129 and amide 130 can be accomplished as described for FIGS. 3 and 4.

Figure 8:
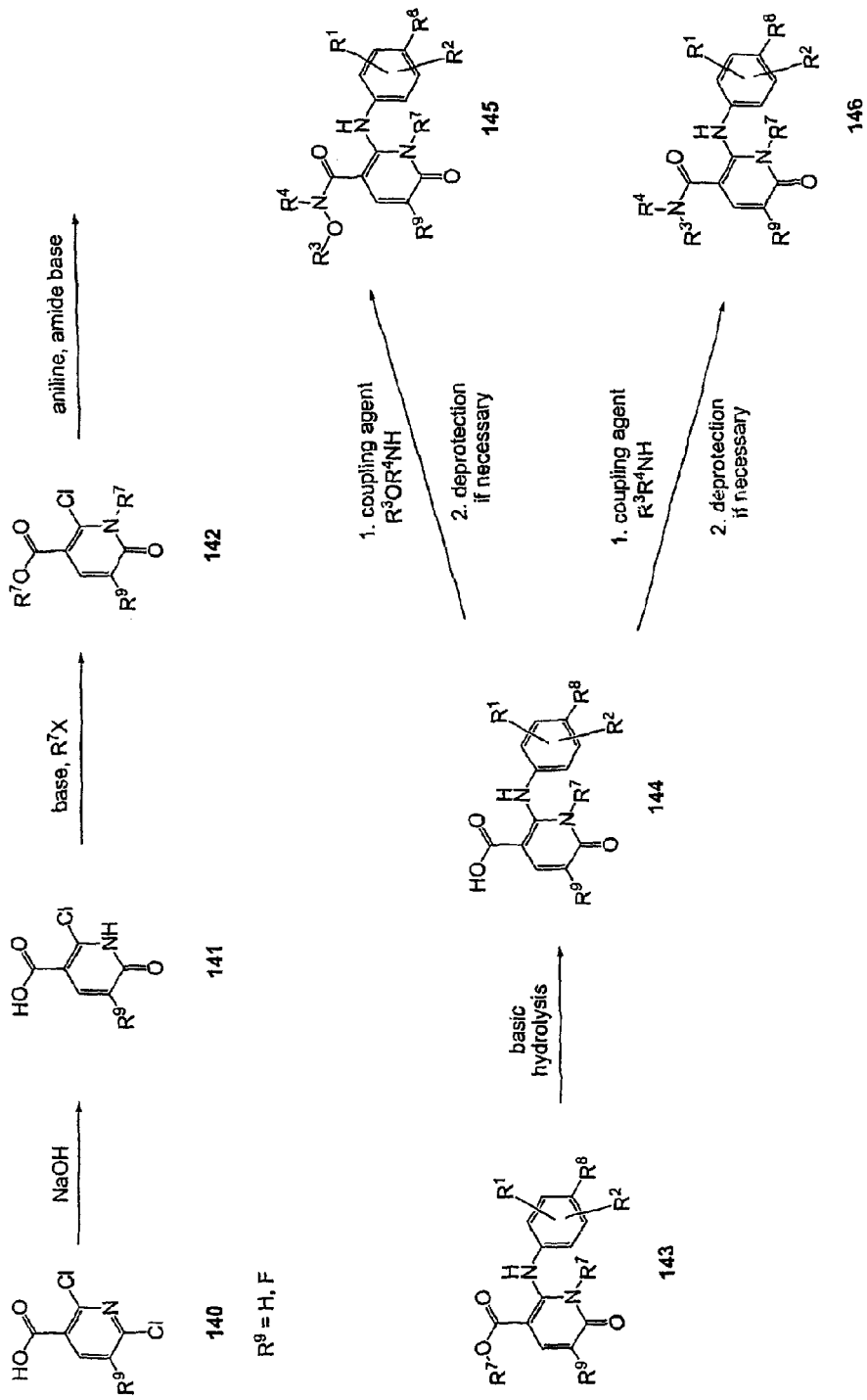
FIG. 8 shows a reaction scheme for the synthesis of compounds 145 and 146.

In FIG. 8, synthesis of compounds of Formula V where R⁹=H or F is depicted, in which 2,6-dichloro-nicotinic acid or 2,6-dichloro-5-fluoro-nicotinic acid is used as the starting material. This route is particularly useful for analogs where R⁷ is Me. The nicotinic acid 140 is converted to the mono chloro acid 141 by refluxing in 2 N aqueous NaOH following the procedure described in U.S. Pat. No. 3,682,932 (1972). Alkylation of 141 can be achieved by standard basic alkylation conditions incorporating alkyl halides, with two equivalents of the appropriate alkyl halide and base to give a mixture of the N-alkyl pyridone ester and the regioisomeric O-alkyl pyridine ester, which are easily separated by column chromatography. These conditions include but are not limited to $K_2CO_3$ in acetone or DMF at room or elevated temperature or NaH in THF at ambient or elevated temperature and then addition of the alkyl halide. Preferably this alkylation is achieved with LiH in DMF at 0° C., followed by addition of alkyl bromide or alkyl iodide and warming to room temperature. Incorporation of the properly substituted aniline moiety to provide 143 is accomplished by $S_NAR$ reaction. This can be done in a suitable organic solvent such as THF using an amide base such as LDA, LiHMDS, NaHMDS, or KHMDS at appropriate temperatures (−78° C. to room temperature. Preferably the aniline is added to LDA or LiHMDS in THF at low temperature (−20 to −80° C.). The pyridone is then added and the mixture is stirred at low temperature to generate ester 143. Carboxylic acid 144 can then be prepared using standard saponification conditions such as LiOH or NaOH in standard mixed aqueous/organic solvent systems. Hydroxamate 145 and amide 146 can be prepared using standard coupling procedures, including but not limited to EDCI, HOBt, or PyBOP and the appropriate amine or hydroxylamine in suitable organic solvents such as DMF, THF, or methylene chloride. Preferably, the coupling is accomplished with HOBt and EDCI in DMF. In some instances, the amine or hydroxylamine used in the coupling reaction contains a standard protecting group. In those cases, the protecting group can be removed by standard conditions known in the art.

Figure 9:
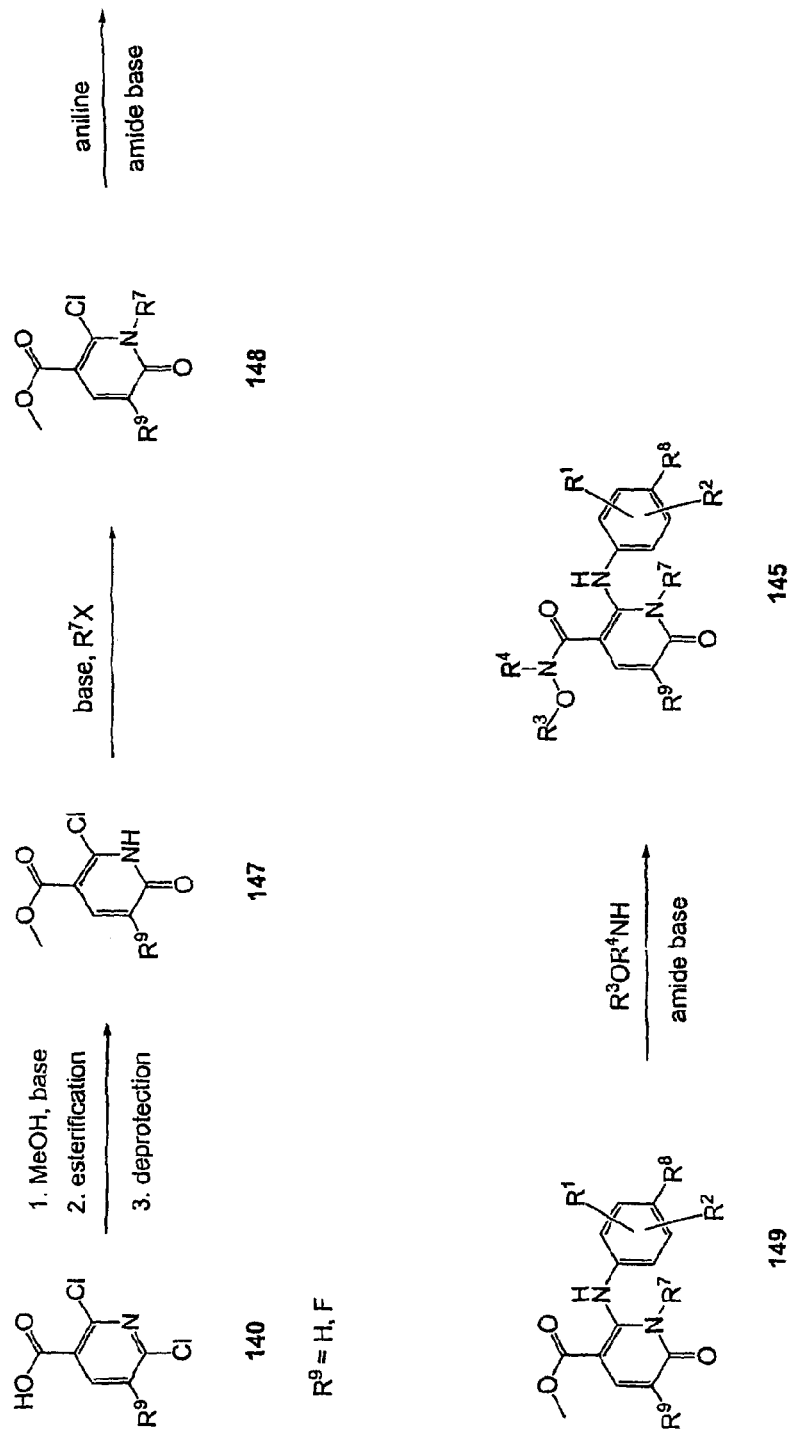
FIG. 9 shows an alternative reaction scheme for the synthesis of compound 145.

In FIG. 9, an alternative synthesis of compounds of Formula V where R⁹H or F is depicted, in which 2,6-dichloro-nicotinic acid or 2,6-dichloro-5-fluoronicotinic acid is used as the starting material. Nicotinic acid 140 can be converted to the N-alkyl pyridone methyl ester 149 following a five step procedure, where 2,6-dichloronicotinic acid 140 is first converted to the methoxy pyridine acid, which is esterified to give the methyl ester and then deprotected to yield the mono chloro ester 147. The conversion to the methoxy pyridine acid is preferably carried out by adding potassium t-butoxide to a solution of the acid 140 in MeOH, and this mixture is then heated to reflux for several days. Esterification to give the methyl ester can be carried out under standard conditions, including but not limited to Fisher esterification (MeOH, $H_2SO_4$), TMSCl in MeOH or $TMSCHN_2$ in suitable organic solvents such as PhMe/MeOH. Demethylation of the methoxy pyridine can then be accomplished by standard conditions including but not limited to HCl at elevated temperature, pTsOH in acetic acid at elevated temperature and aqueous HBr in MeOH at elevated temperature. Preferable demethylation to give pyridone 147 is achieved by treatment of the methoxy pyridine with aqueous HBr in acetic acid at elevated temperature (80 to 120° C.). Alkylation of 147 to provide 148 can be achieved by standard basic alkylation conditions incorporating alkyl halides, with one equivalent of the appropriate alkyl halide and base to give a mixture of the N-alkyl pyridone ester and the regioisomeric O-alkyl pyridine ester, which are easily separated by column chromatography. These conditions include but are not limited to $K_2CO_3$ in acetone or DMF at room or elevated temperature or NaH in THF at ambient or elevated temperature and then addition of the alkyl halide. Preferably this alkylation is achieved with LiH in DMF at 0° C., followed by addition of alkyl bromide or alkyl iodide and warming to room temperature. Incorporation of the properly substituted aniline moiety is accomplished by $S_NAR$ reaction. This can be done in a suitable organic solvent such as THF using an amide base such as LDA, LiHMDS, NaHMDS, or KHMDS at appropriate temperatures (−78° C. to room temperature). Preferably the aniline is added to LDA or LiHMDS in THF at low temperature (−20 to −80° C.). The pyridone is then added and the mixture is stirred at low temperature to generate ester 149. Hydroxamate 145 can be prepared directly from methyl ester 149 in a suitable organic solvent such as THF using the appropriate hydroxylamine and amide base such as LDA, LiHMDS, NaHMDS, or KHMDS at appropriate temperatures (−78° C. to room temperature). Preferably, a solution of LiHMDS is added to a solution of the methyl ester 149 and the hydroxylamine in THF at 0° C. The reaction mixture is then warmed to room temperature to yield the desired hydroxamate 145. In some instances, the hydroxylamine used in the coupling reaction contains a standard protecting group. In those cases, the protecting group can be removed by standard conditions known in the art.

In a further aspect, this invention provides a method of preparing a compound of Formula IA, said method comprising:

reacting a compound of Formula 100 or 101

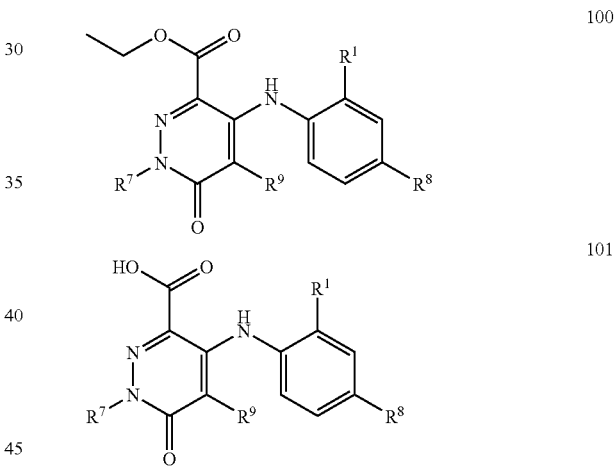

with $R^3NH_2$ either in the presence of (i) a coupling reagent when $R^3$ is as defined in Formula IA or (ii) an amide base when $R^3$ is as defined in Formula IA with the exception that $R^3$ is not H or Me, to provide said compound of Formula IA.

In a further aspect, this invention provides a method of preparing a compound of Formula IV, said method comprising:

reacting a compound of Formula 108 or 109

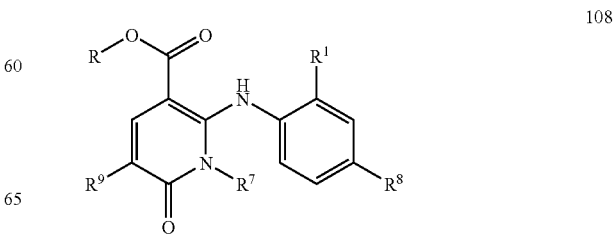

-continued

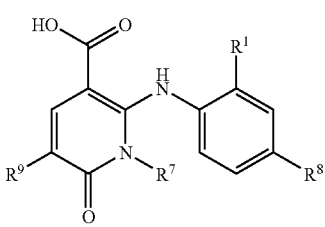
109 with R³NH₂ wherein R³ is as defined in Formula IV, either in the presence of (i) a coupling reagent or (ii) an amide base when R³ is as defined in Formula IV with the exception that R³ is not H or Me.

In a further aspect, this invention provides a method of preparing a compound of Formula VI, said method comprising:

(a) brominating a compound having the formula 105

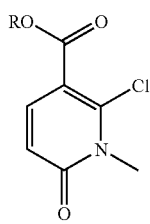
105 wherein R is alkyl, to provide compound 106

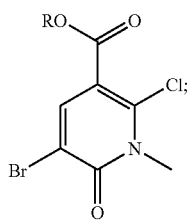
106

(b) reacting compound 106 with Zn(Me)₂ in the presence of a palladium catalyst and a ligand, and optionally in the presence of a base, to provide compound 107

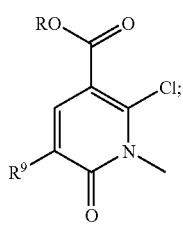
107

(c) reacting compound 107 with an aniline having the formula

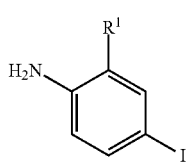

in the presence of a palladium catalyst, a phosphine ligand, and an amide base, to provide compound 108

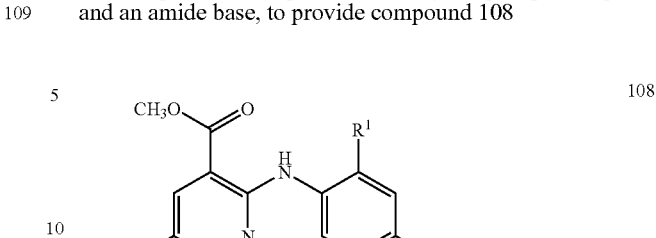
108

(d) optionally hydrolyzing compound 108 under basic conditions to provide compound 109

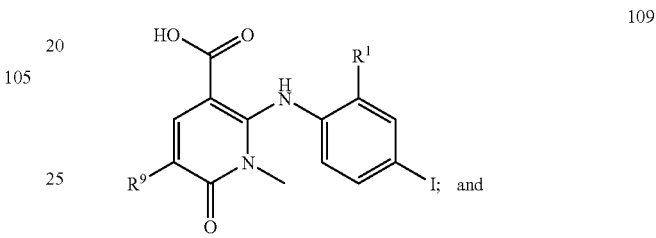
109 and (e) reacting either compound 108 or compound 109 with R³NH₂ either in the presence of (i) a coupling reagent when R³ is as defined in Formula VI or (ii) an amide base when R³ is as defined in Formula VI with the exception that R³ is not H, to provide said compound of Formula VI.

In one embodiment, compound 105 is prepared by the method comprising:

(a) reacting compound 103

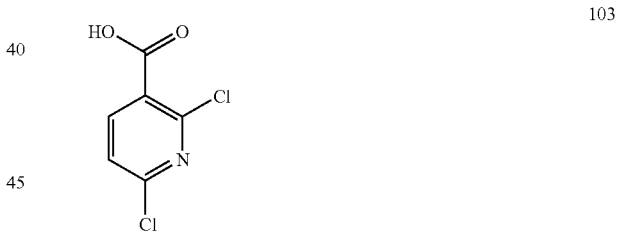
103 with aqueous sodium hydroxide to provide compound 104

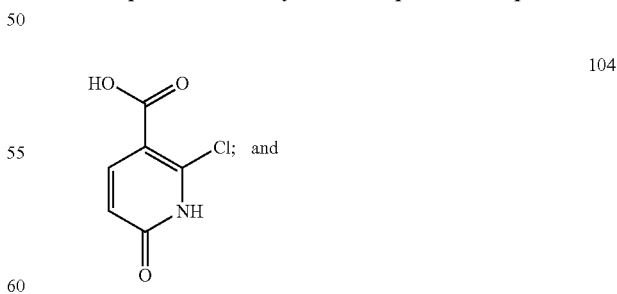
104 and (b) reacting compound 104 with RX, wherein R is Me and X is a halide, in the presence of a base to provide compound 105.

In a further aspect, this invention provides a method of preparing a compound of Formula II, said method comprising:

(a) reacting a hydrazine having the formula Me-NH—NH$_2$ with:
(i) diethyl 2-oxomalonate, followed by treatment with an acylating reagent that delivers an acyl group having the formula C(=O)CH$_2$R$^9$ wherein R$^9$ is as defined in Formula II, or
(ii) an acylating reagent that delivers an acyl group having the formula C(=O)CH$_2$R$^9$ wherein R$^9$ is as defined in Formula II, followed by treatment with diethyl ketomalonate, to provide compound 97

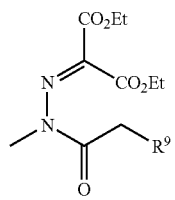

97

(b) treating compound 97 with an amide base at a temperature below −40° C., followed by treatment with concentrated HCl, to provide a compound of formula 98

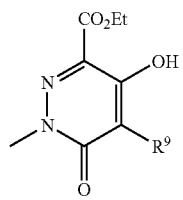

98

(c) chlorinating compound 98 to provide compound 99

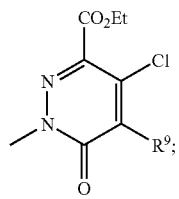

99

(d) reacting compound 99 with an aniline having the formula

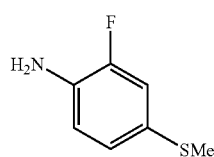

in the presence of a palladium catalyst, a ligand, and an amide base, to provide compound 100

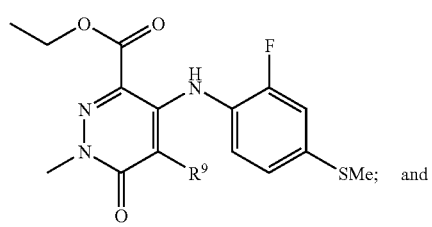

100

(e) reacting a compound of Formula 100 with R$^3$NH$_2$ either in the presence of (i) a coupling reagent when R$^3$ is as defined in Formula II or (ii) an amide base when R$^3$ is as defined in Formula II with the exception that R$^3$ is not H, to provide said compound of Formula II.

In a further aspect, this invention provides a method of preparing a compound of Formula II wherein R$^9$ is H, Me, or Cl, said method comprising:
(a) reacting a hydrazine having the formula Me-NH—NH$_2$ with:
(i) diethyl 2-oxomalonate, followed by treatment with an acylating reagent that delivers an acyl group having the formula C(=O)CH$_2$R$^9$ wherein R$^9$ is H, Me, or Cl; or
(ii) an acylating reagent that delivers an acyl group having the formula C(=O)CH$_2$R$^9$ wherein R$^9$ is H, Me, or Cl, followed by treatment with diethyl ketomalonate, to provide compound 97

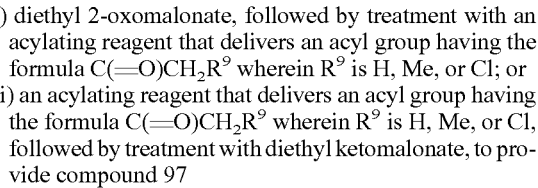

97

(b) treating compound 97 with an amide base at a temperature below −40° C. to give a compound of formula 98

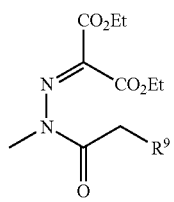

98

(c) chlorinating compound 98 to provide compound 99

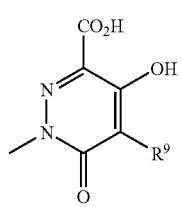

99

(d) reacting compound 99 with an aniline having the formula

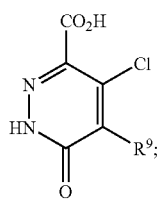

in the presence of an amide base, to provide compound 101

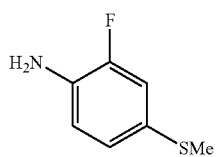

101

(e) reacting compound 101 with R$^3$NH$_2$ either in the presence of (i) a coupling reagent when R$^3$ is as defined in For-

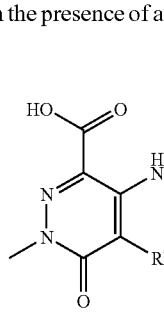

mula II or (ii) an amide base when R³ is as defined in Formula II with the exception that R³ is not H, to provide said compound of Formula II.

In a further aspect, this invention provides a method of preparing a compound of Formula V wherein R⁹ is Me, said method comprising:

(a) brominating a compound having the formula 105

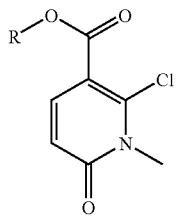

wherein R is alkyl, to provide compound 106

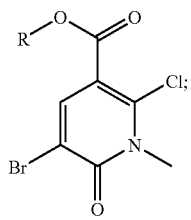

(b) reacting compound 106 with Zn(Me)₂ in the presence of a palladium catalyst and a ligand, and optionally in the presence of a base, to provide compound 107

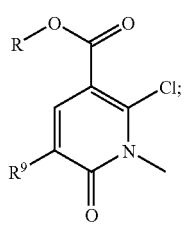

(c) reacting compound 107 with an aniline having the formula

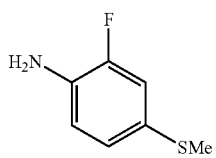

in the presence of an amide base, to provide compound 108

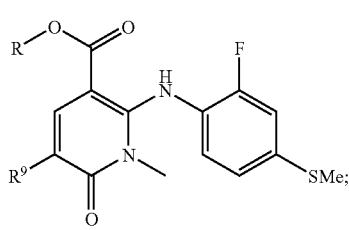

(d) optionally hydrolyzing compound 108 under basic conditions to provide compound 109

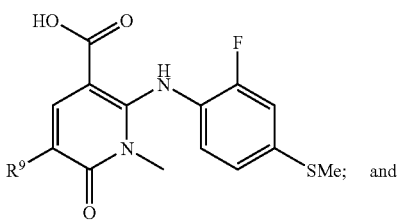

(e) reacting either compound 108 or compound 109 with R³NH₂, wherein R³ is as defined in Formula V, in the presence of a coupling reagent or an amide base, to provide said compound of Formula V.

In a further aspect, this invention provides a method of preparing a compound of Formula V wherein R⁹ is Cl, said method comprising:

(a) reacting a compound of Formula 112

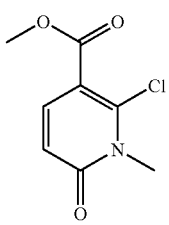

with an aniline having the formula

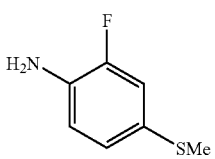

in the presence of an amide base to provide compound 117

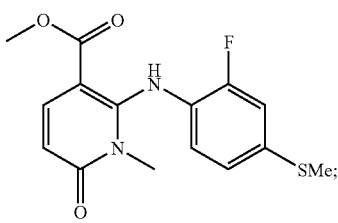

(b) chlorinating compound 117 to provide compound 118

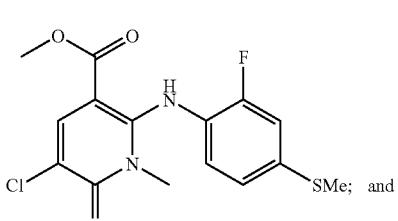

(c) optionally hydrolyzing compound 118 to provide compound 118A

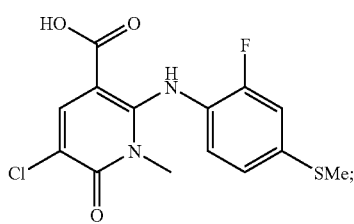

(d) reacting either compound 118 or 118A with (S)-MeCH(OH)CH$_2$ONH$_2$ or HOCH$_2$CH$_2$ONH$_2$ in the presence of a coupling reagent or an amide base, to provide said compound of Formula V.

In a further aspect, this invention provides a method of preparing a compound of Formula V wherein R$^9$ is H or F, said method comprising:

(a) treating a compound of formula 140

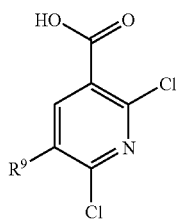

wherein R$^9$ is H or F, with aqueous NaOH to provide compound 141

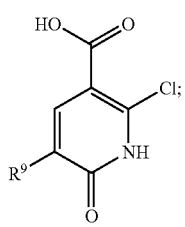

(b) reacting compound 141 with CH$_3$X, wherein X is a halide, in the presence of a base to provide compound 142

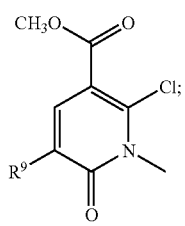

(c) reacting compound 142 with an aniline having the formula

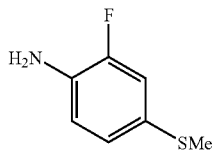

in the presence of an amide base to provide compound 143

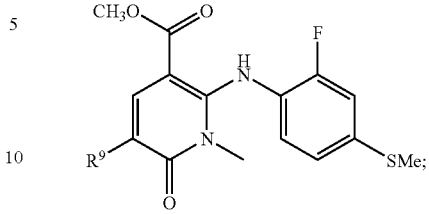

(d) optionally hydrolyzing compound 143 to provide compound 144

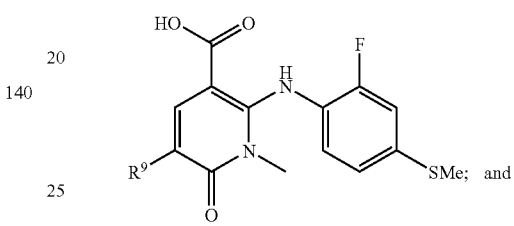

(e) reacting either compound 143 or 144 with R$^3$NH$_2$, wherein R$^3$ is as defined in Formula V, in the presence of a coupling reagent or an amide base, to provide said compound of Formula V.

In one embodiment of the above methods, the coupling agent is 1-(3-dimethylaminopropyl)-3-ethylcarbodiimide hydrochloride, 1-hydroxybenzotriazole-6-sulfonamidomethyl hydrochloride, or benzotriazol-1-yl-oxytripyrrolidinophosphonium hexafluorophosphate.

In a further aspect the present invention provides a method of using the compounds of this invention as a medicament to treat diseases or medical conditions mediated by MEK. For example, this invention provides a compound of this invention as a medicament for treatment of a hyperproliferative disorder or an inflammatory condition in a mammal comprising administrating to said mammal one or more compounds of the present invention or a pharmaceutically acceptable salt or prodrug thereof in an amount effective to treat said hyperproliferative disorder. In another aspect this invention provides a compound of this invention in the manufacture of a medicament for the treatment of a hyperproliferative disorder or an inflammatory condition.

In a further aspect, the present invention provides a method of producing a producing a MEK inhibitory effect in a warm-blooded animal, such as man, in need of such treatment which comprises administering to said animal an effective amount of a compound of this invention.

In a further aspect the present invention provides treating or preventing an MEK-mediated condition, comprising administering to a human or animal in need thereof a pharmaceutical composition comprising a compound of the present invention or a pharmaceutically acceptable salt or in vivo cleavable prodrug thereof in an amount effective to treat or prevent said MEK-mediated condition.

The invention also relates to pharmaceutical compositions that inhibit MEK, comprising an effective amount of a compound selected from the present invention or pharmaceutically acceptable prodrugs, pharmaceutically active metabolites, or pharmaceutically acceptable salts thereof.

The invention also relates to a pharmaceutical composition for the treatment of a hyperproliferative disorder in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) or the treatment of pain in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease or other inflammatory condition such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of a compound of the present invention, or a pharmaceutically acceptable salt, prodrug or hydrate thereof. In one embodiment, said method relates to the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease in a mammal that comprises administering to said mammal a therapeutically effective amount of a compound of the present invention, or a pharmaceutically acceptable salt, prodrug or hydrate thereof.

The invention also relates to a method of preventing blastocyte implantation in a mammal that comprises administering to said mammal a therapeutically effective amount of a compound of the present invention, or a pharmaceutically acceptable salt, prodrug or hydrate thereof.

The invention also relates to a method of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a pharmaceutical composition for treating a disease or condition related to inflammatory disease, autoimmune disease, destructive bone disorders, proliferative disorders, infectious disease, viral disease, fibrotic disease or neurodegenerative disease in a mammal which comprises a therapeutically effective amount of a compound of the present invention, or a pharmaceutically acceptable salt, prodrug or hydrate thereof, and a pharmaceutically acceptable carrier. Examples of the above diseases and/or conditions include but is not limited to rheumatoid arthritis, atherosclerosis, inflammatory bowel disease, skin diseases such as psoriasis, eczema, and scleroderma, diabetes and diabetic complications, diabetic retinopathy, retinopathy of prematurity, age-related macular degeneration, hemangioma, chronic obstructive pulmonary disease, idiopathic pulmonary fibrosis, allergic responses including asthma allergic rhinitis and atopic dermatitis, renal disease and renal failure, polycystic kidney disease, acute coronary syndrome, congestive heart failure, osteoarthritis, neurofibromatosis, organ transplant rejection, cachexia and pain.

Further provided is a compound of the present invention for use as a medicament in the treatment of the diseases and conditions described above in a warm-blooded animal, preferably a mammal, more preferably a human, suffering from such disorder. Also provided is the use of a compound of the present invention in the preparation of a medicament for the treatment of the diseases and conditions described above in a warm-blooded animal, preferably a mammal, more preferably a human, suffering from such disorder.

Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In a further aspect, the present invention provides pharmaceutical compositions that inhibit MEK comprising one or more compounds of the present invention.

This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein.

The inventive compounds may further be used advantageously in combination with other known therapeutic agents. For example, the invention also relates to a method of and to a pharmaceutical composition of inhibiting abnormal cell growth in a mammal which comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

The terms "abnormal cell growth" and "hyperproliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/theroine kinase activation occurs.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of MEK, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the present invention or a pharmaceutically acceptable salt or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the present invention, or a pharmaceutically acceptable salt or prodrug thereof, as defined hereinbefore in association with a pharmaceutically acceptable diluent or carrier.

To prepare the pharmaceutical compositions according to one embodiment of this invention, a therapeutically or prophylactically effective amount of a compound of the present invention or a pharmaceutically acceptable salt, solvate, metabolite or prodrug thereof (alone or together with an additional therapeutic agent) is intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of the present invention, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 1 mg/kg/day to about 35 mg/kg/day, in single or divided doses. For a 70 kg human, this would amount to about 0.07 to 2.45 g/day, preferably about 0.05 to about 1.0 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of the present invention will naturally vary according to the nature and severity of the conditions, the age and sex of the animal or patient and the route of administration, according to well known principles of medicine.

The compounds of this invention may be used alone in combination with other drugs and therapies used in the treatment of disease states which would benefit from the inhibition of MEK. Such treatment may involve, in addition to the compounds of the invention, conventional surgery or radiotherapy or chemotherapy. Such chemotherapy may include one or more of the following categories of anti-tumor agents:

(i) antiproliferative/anti-neoplastic drugs and combinations thereof, as used in medical oncology, such as alkylating agents (for example, cisplatin, oxaliplatin, carboplatin, cyclophosphamide, nitrogen mustard, melphalan, chlorambucil, busulphan, temozolamide and nitrosoureas); anti-metabolites (for example, gemcitabine, antifolates such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere and polokinase inhibitors); and topoisomerase inhibitors (for example epipodophyllotoxins like eptoposide and teniposide, amsacrine, topotecan and campothecin);

(ii) cytostatic agents such as antiestrogens (for example, tamoxifen, toremifene, raloxifene, droloxifene and iodoxyfene), estrogen receptor down regulators (for example, fulvestratrant) antiandrogens (for example, bicalutamide, flutamide, nilutamide, cyproxerone acetate and Casodex™ (4'-cyano-3-(4-fluorophenylsulphonyl)-2-hydroxy-2-methyl-3'-(trifluoromethyl)propionanilide)), LHRH antagonists or LHRH agonists (for example, goserelin, leuporelin and buserelin), progestogens (for example, megestrol acetate), aromatase inhibitors (for example, asanastrozole, letrozole, vorazole and exemestane) and inhibitors of 5α-reductase such as finasteride;

(iii) anti-invasion agents (for example, c-Src kinase family inhibitors and metalloproteinase inhibitors like marimastat and inhibitors of urokinase plasminogne activator receptor function or antibodies to Heparanase);

(iv) inhibitors of growth factor function like growth factor antibodies, growth factor receptor antibodies (for example, the anti-erbB2 antibody trastumuzab [Herceptin™], the anti-EGFR antibody panitumumab and the anti-erbB1 antibody cetuximab [Erbitux C225]), and any growth factor or growth factor receptor antibodies disclosed by Stem et al. Critical Reviews in Oncology/Haematology, 2005, vol. 54, pp 11-29): such inhibitors include tyrosine kinase inhibitors (for example, inhibitors of the epidermal growth factor family tyrosine kinases such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signaling inhibitors such as farnesyl transferase inhibitors, for example sorafenib (BAY 43-9006)), inhibitors of cell signaling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor (for example, the anti-vascular endothelial cell growth factor antibody bevacizumab [Avastin™], and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in PCT Publication Nos. WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon; and (x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies.

Such conjoint treatment may be achieved by way of the simultaneous, sequential or separate dosing of the individual components of treatment. Such combination products employ the compounds of this invention within the dose range described hereinbefore and the other pharmaceutically active agent within its approved dose range.

According to this aspect of the invention there is provided a pharmaceutical product comprising a compound of the present invention as defined herein and an additional anti-tumor agent as defined hereinbefore for the conjoint treatment of cancer.

Although the compounds of the present invention are primarily of value as therapeutic agents for use in warm-blooded animals (including man), they are also useful whenever it is required to inhibit the effects of MEK. Thus, they are useful as pharmacological standards for use in the development of new biological tests and in the search for new pharmacological agents.

Representative compounds of the present invention, which are encompassed by the present invention include, but are not limited to the compounds of the examples and their pharmaceutically acceptable acid or base addition salts or prodrugs thereof. The examples presented below are intended to illustrate particular embodiments of the invention, and are not intended to limit the scope of the specification or the claims in any way.

The disclosures in this application of all articles and references, including patents, are incorporated herein by reference.

In another embodiment of the invention, an article of manufacture, or "kit", containing materials useful for the treatment of the disorders described above is provided. In one embodiment, the kit comprises a container comprising a compound of the present invention or a formulation thereof. The kit may also comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container holds a compound of the present invention or a formulation thereof, which is effective for treating the condition, and may have a sterile access port (for example, the container may be an intravenous solution bag or a vial having a stopper pierceable by a hypodermic injection needle). The label or package insert may indicate that the composition is used for treating the condition of choice, such as cancer. In one embodiment, the label or package inserts indicates that the compound of the present invention or a formulation thereof can be used to treat a disease or medical condition mediated by MEK. In addition, the label or package insert may indicate that the patient to be treated is one having a disease or medical condition mediated by MEK such as a hyperproliferative disorder or an inflammatory condition. The label or package insert may also indicate that the composition can be used to treat other disorders. Alternatively, or additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

According to another embodiment, a kit may comprise (a) a first container with a compound of the present invention or a formulation thereof contained therein; and optionally (b) a second container with a second pharmaceutical formulation contained therein, wherein the second pharmaceutical formulation comprises a second compound with anti-hyperproliferative or anti-inflammatory activity. Alternatively, or additionally, the article of manufacture may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of a compound of the present invention or a formulation thereof and, if present, the second pharmaceutical formulation. For example, if the kit comprises a compound of the present invention or a formulation thereof ("first formulation") and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of the present invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

In certain other embodiments wherein the kit comprises a compound of the present invention or a formulation thereof and a second therapeutic agent, the kit may comprise a container for containing the separate components such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

BIOLOGICAL ASSAYS

The following assays can be used to measure the effects of the compounds of the present invention as MEK inhibitors.

Example A

MEK Enzyme Assay

Test 1a

The activity of the compounds of the present invention may be determined by the following procedure. N-terminal 6 His-tagged, constitutively active MEK-1 (2-393) is expressed in *E. coli* and protein is purified by conventional methods (Ahn et al., Science 1994, 265, 966-970). The activity of MEK1 is assessed by measuring the incorporation of $\gamma$-$^{33}$P-phosphate from $\gamma$-$^{33}$P-ATP onto N-terminal His tagged ERK2, which is expressed in *E. coli* and is purified by conventional methods, in the presence of MEK-1. The assay is carried out in 96-well polypropylene plate. The incubation mixture (100 µL) comprises of 25 mM Hepes, pH 7.4, 10 mM MgCl$_2$, 5 mM $\beta$-glycerolphosphate, 100 µM Na-orthovanadate, 5 mM DTT, 5 nM MEK1, and 1 µM ERK2. Inhibitors are suspended in DMSO, and all reactions, including controls are performed at a final concentration of 1% DMSO. Reactions are initiated by the addition of 10 µM ATP (with 0.5 µCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvester. Plates are allowed to air-dry prior to adding 30 µL/well of Packard Microscint 20, and plates are counted using a Packard TopCount.

Example B

Cellular ERK 1/2 Phosphorylation Assay

Test 1b

The MEK 1/2 inhibition properties of the compounds of the invention may be determined by the following in vitro cellular assay. Inhibition of basal ERK1/2 phosphorylation was determined by incubating cells with compound for 1 hour and quantifying the fluorescent pERK signal on fixed cells and normalizing to total ERK signal.

Materials and Methods: Malme-3M cells were obtained from ATCC and grown in RPMI-1640 supplemented with 10% fetal bovine serum. Cells were plated in 96-well plates at 15,000 cells/well and allowed to attach for 1-2 hours. Diluted compounds were then added at a final concentration of 1% DMSO. After 1 hour, cells were washed with PBS and fixed in 3.7% formaldehyde in PBS for 15 minutes. This was followed by washing in PBS/0.2% Triton X-100 and permeabilizing in 100% MeOH for 15 minutes. Cells were blocked in Odyssey blocking buffer (LI-COR Biosciences) for at least 1 hour. Antibodies to phosphorylated ERK 1/2 (Cell Signaling #9106, monoclonal) and total ERK 12 (Santa Cruz Biotechnology #sc-94, polyclonal) were added to the cells and incubated for at least 1 hour. After washing with PBS/0.2% TritonX-100, the cells were incubated with fluorescently-labeled secondary antibodies (goat anti-rabbit IgG-IRDye800, Rockland and goat anti-mouse IgG-Alexa Fluor 680, Molecular Probes) for an additional hour. Cells were then washed and analyzed for fluorescence at both wavelengths using the Odyssey Infrared Imaging System (LI-COR Biosciences). Phosphorylated ERK signal was normalized to total ERK signal.

Example C

Aqueous Solubility Assay

The thermodynamic aqueous solubility of compounds was measured using a modified shake-flask method. Crystallinity of each compound was confirmed using a polarizing light microscope (Olympus BX51). For each compound tested, approximately 0.5 mg of dry compound was weighed into a vial to be used to make the standard solutions. Approximately 0.5 mg was also weighed into several vials for the aqueous unknowns, one vial for each pH to be tested.

For each aqueous unknown, 0.5 mL of aqueous buffer (10 mM potassium phosphate) at the desired pH was added to 0.5 mg of dry compound. (For pH 1.2, 0.1 N HCl was used.) The upper concentration limit for this assay was thus 1 mg/mL. Each aqueous unknown was then swirled at 350 rpm at room temperature for 24 hours to allow adequate time for equilibration. After swirling, the final pH of each sample was checked and confirmed. Aliquots were subsequently removed and filtered into HPLC vials for analysis.

A stock solution was prepared for each compound by dissolving 0.5 mg of compound into a total volume of 1 mL methanol for a stock concentration of 500 µg/mL. The stock solution was then serially diluted to create a calibration curve from 5 to 250 g/mL.

Samples and standards were immediately analyzed by LC/UV. For each of the aqueous samples, two different volumes were injected in triplicate. For each of the standards, two different volumes were injected in singlicate. Samples yielding peaks outside of the calibration range were serially diluted and reanalyzed.

The HPLC/PDA system was comprised of an Alliance 2795 Separations System (Waters) or an Acquity HPLC Separations System (Waters) combined with a 2996 Photodiode Array Detector (Waters). On the Alliance System, chromatographic separation of the analyte was achieved using a YMC ODS-Aq C18 column (3.0×50 mm, 3 µm particle size, 120 Å, Waters) in conjunction with gradient conditions using mobile phases A (aqueous, 0.01% heptafluorobutyric acid (HFBA), 1% isopropyl alcohol) and B (0.01% HFBA and 1% isopropyl alcohol in acetonitrile). The total run time, including re-equilibration time, for a single injection was 5 minutes. Analyte responses were measured by monitoring the absorbance at 220 nm and 254 nm. The limit of detection for most compounds on this system was about 1 µg/mL.

On the Acquity System, chromatographic separation of the analyte was achieved using an Acquity HPLC BEH, C18 column (2.1×50 mm, 1.7 µm particle size, Waters) in conjunction with gradient conditions using mobile phases A (aqueous, 0.1% formic acid (FA), 1% isopropyl alcohol) and B (0.1% FA and 1% isopropyl alcohol in acetonitrile). The total run time, including re-equilibration time, for a single injection was 3 minutes. Analyte responses were measured by monitoring the absorbance at 220 nm and 254 nm. The limit of detection for most compounds on this system was about 1 μg/mL. On the back end of the Acquity System is a ZQ-2000 single quadrupole mass spectrometer (Waters). Positive ESI was used for mass identification of the parent compound.

Data were acquired and processed using the Waters Empower software. Calibration was achieved by plotting the peak area ratios of analyte as a function of the nominal concentrations of the standard samples. A calibration model was generated by linear regression of the calibration curve. The model was used to calculate the concentrations in all aqueous samples.

Although the pharmacological properties of the compounds of Formulae I to VI vary with structural change as expected, in general the activity and/or solubility possessed by the compounds may be demonstrated at the following concentrations or doses:

Compounds of Formula II:
Test 1a (enzyme assay): $IC_{50} \leq 250$ nM, for example $\leq 100$ nM, as a further example $\leq 30$ nM.
Test 1b: (cell assay): $IC_{50} \leq 180$, for example $\leq 80$ nM, as a further example $\leq 10$ nM.

Compounds of Formula III:
Test 1a (enzyme assay): $IC_{50} \leq 250$ nM, for example $\leq 50$ nM, as a further example $\leq 20$ nM; and
Test 1b: (cell assay): $IC_{50} \leq 600$ nM, for example $\leq 30$ nM, as a further example $\leq 10$ nM.

Compounds of Formula V:
Test 1a (enzyme assay): $IC_{50} \leq 40$ nM, for example $\leq 20$ nM; and
Test 1b: (cell assay): $IC_{50} \leq 10$ nM.

Compounds of Formula VI:
Test 1a (enzyme assay): $IC_{50} \leq 35$ nM, as a further example $\leq 15$ nM, and as a further example $\leq 10$ nM.
Test 1b: (cell assay): $IC_{50} \leq 5$ nM, as a further example $\leq 1$ nM.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as $CDCl_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

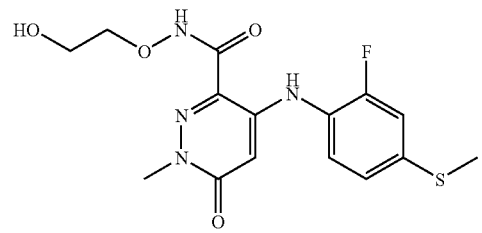

4-(2-Fluoro-4-(methylthio)phenylamino)-N-(2-hydroxyethoxy)-1-methyl-6-oxo-1,6-dihydropyridazine-3-carboxamide Step A: Preparation of ethyl 2-(2-methylhydrazono)propanoate: To a suspension of ethyl pyruvate (37.8 mL, 338 mmol) and $MgSO_4$ (40.8 g, 339 mmol) in $CHCl_3$ (500 mL) was added a solution of methylhydrazine (18.0 mL, 332 mmol) in $CHCl_3$ (100 mL) at 0° C. The reaction mixture was warmed to room temperature. After stirring for 24 hours at room temperature, the reaction mixture was filtered. The filtrate was concentrated under reduced pressure to give 44 g (94%) of the desired product that was used directly without further purification.

Step B: Preparation of methyl 3-(2-(1-ethoxy-1-oxopropan-2-ylidene)-1-methylhydrazinyl)-3-oxopropanoate: To a solution of ethyl 2-(2-methylhydrazono)propanoate (25.0 mL, 186 mmol) in THF (500 mL) at 0° C. was added LiH (2.02 g, 241 mmol). The resulting mixture was stirred for 10 minutes at 0° C., warmed to room temperature, and stirred for 6 hours. Methyl malonyl chloride (26.7 mL, 242 mmol) in THF (20 mL) was added at 0° C. The reaction was warmed to room temperature and stirred for 16 hours. The reaction was carefully quenched with 1N aqueous HCl at 0° C., concentrated under reduced pressure, and diluted with EtOAc. The organic layer was dried over $MgSO_4$, filtered, and concentrated under reduced pressure to give 46 g (99%) of the desired product that was used directly without further purification.

Step C: Preparation of methyl 5-hydroxy-2,6-dimethyl-3-oxo-2,3-dihydropyridazine-4-carboxylate: To a solution of ethyl 2-(2-methyl-2-(methyl 3-oxopropanoyl)hydrazono) propanoate (1.02 g, 4.09 mmol) in MeCN (10 mL) at 0° C. was added DBU (2.0 mL, 13 mmol). The reaction mixture was warmed to room temperature and stirred for 3 hours. The reaction mixture was concentrated under reduced pressure and diluted with EtOAc. The organic layer was washed with 10% aqueous HCl, dried over MgSO$_4$, filtered, and concentrated under reduced pressure to give 0.39 g (48%) of the crude product that was used directly without further purification.

Step D: Preparation of 5-hydroxy-2,6-dimethylpyridazin-3(2H)-one: A mixture of methyl 5-hydroxy-2,6-dimethyl-3-oxo-2,3-dihydropyridazine-4-carboxylate (3.00 g, 15.1 mmol) and 6 N aqueous HCl (25 mL, 150 mmol) in dioxane (25 mL) was refluxed for 48 hours. The reaction mixture was cooled to room temperature and concentrated under reduced pressure to give the crude material that was diluted with EtOAc. The organic layer was washed with water and brine, dried over MgSO$_4$, filtered, and concentrated under reduced pressure to give 0.74 g (35%) of the desired product. The aqueous layer was concentrated under reduced pressure. The resulting solid was diluted with water and EtOAc-THF. The organic layer was separated. The aqueous layer was extracted with EtOAc (2×). The combined organic layers were dried over MgSO$_4$, filtered, and concentrated under reduced pressure to give 0.80 g (37%) of the additional desired product. A total of 1.54 g (72%) of the desired product was obtained, which was used directly without further purification.

Step E: Preparation of 5-chloro-2,6-dimethylpyridazin-3(2H)-one: A mixture of 5-hydroxy-2,6-dimethylpyridazin-3(2H)-one (736 mg, 5.25 mmol) and POCl$_3$ (4.5 mL) was stirred at 85° C. for 2 hours. The reaction mixture was concentrated under reduced pressure to give the crude material that was quenched with saturated aqueous Na$_2$CO$_3$. The resulting mixture was stirred for 2 hours and extracted with EtOAc (3×). The combined organic layers were dried over MgSO$_4$, filtered, and concentrated under reduced pressure to give 587 mg (70%) of the desired product that was used directly without further purification.

Step F: Preparation of 4-chloro-1-methyl-6-oxo-1,6-dihydropyridazine-3-carboxylic acid: To a solution of 5-chloro-2,6-dimethylpyridazin-3(2H)-one (780 mg, 4.67 mmol) in fuming H$_2$SO$_4$ (25 mL) at 0° C. was slowly added K$_2$Cr$_2$O$_7$ (3.33 g, 11.2 mmol) with stirring. After the addition of K$_2$Cr$_2$O$_7$, the ice-bath was removed and the reaction mixture was allowed to warm to room temperature. When the reaction began to progress too rapidly, the ice-bath was replaced and the rest of K$_2$Cr$_2$O$_7$ was added. The reaction mixture was stirred at 60° C. for 16 hours. The reaction mixture was cooled to room temperature, poured into ice, and extracted with EtOAc (3×). The combined organic layers were dried over MgSO$_4$, filtered, and concentrated under reduced pressure to give 649 mg (74%) of the desired product that was used directly without further purification.

Step G: Preparation of methyl 4-chloro-1-methyl-6-oxo-1,6-dihydropyridazine-3-carboxylate: A solution of 4-chloro-1-methyl-6-oxo-1,6-dihydropyridazine-3-carboxylic acid (390 mg, 2.07 mmol) and conc. HCl (0.10 mL) in MeOH (6 mL) was refluxed for 8 hours. The reaction mixture was cooled to room temperature and concentrated under reduced pressure to give the crude material that was redissolved into EtOAc. The organic layer was washed with water, dried over MgSO$_4$, filtered, and concentrated under reduced pressure to give the crude material that was purified by silica gel flash column chromatography (100% hexanes to 10 to 20 to 30 to 50% EtOAc in hexanes) to afford 72 mg (17%) of the desired product.

Step H: Preparation of methyl 4-(2-fluoro-4-(methylthio)phenylamino)-1-methyl-6-oxo-1,6-dihydropyridazine-3-carboxylate: A mixture solution of methyl 4-chloro-1-methyl-6-oxo-1,6-dihydropyridazine-3-carboxylate (72 mg, 0.35 mmol), 2-fluoro-4-methylthioaniline (69 mg, 0.44 mmol), Pd(OAc)$_2$ (10 mg, 0.044 mmol), BINAP (40 mg, 0.064 mmol), and Cs$_2$CO$_3$ (197 mg, 0.60 mmol) in toluene (1.5 mL) was sealed in a vial under N$_2$ atmosphere. It was stirred for 10 minutes at room temperature and then heated at 80° C. for 16 hours with stirring. The reaction mixture was cooled to room temperature and diluted with EtOAc. The precipitate was filtered off and washed with EtOAc. The filtrate was washed with water. The organic layer was separated and the aqueous layer was extracted with EtOAc. The combined organic layers were dried over MgSO$_4$, filtered, concentrated to give the crude material that was purified by silica gel flash column chromatography (100% CH$_2$Cl$_2$ to 1% MeOH in CH$_2$Cl$_2$) followed by additional silica gel flash column chromatography (10 to 15 to 20% EtOAc in CH$_2$Cl$_2$) to afford 48 mg (42%) of the desired product.

Step I: Preparation of 4-(2-fluoro-4-(methylthio)phenylamino)-1-methyl-6-oxo-N-(2-(vinyloxy)ethoxy)-1,6-dihydropyridazine-3-carboxamide: To a solution of methyl 4-(2-fluoro-4-(methylthio)phenylamino)-1-methyl-6-oxo-1,6-dihydropyridazine-3-carboxylate (25 mg, 0.077 mmol) and O-(2-vinyloxy-ethyl)-hydroxylamine (24 mg, 0.23 mmol) in THF (2 mL) at 0° C. was added LiHMDS (0.54 mL, 0.54 mmol, 1 M in THF). The reaction mixture was warmed to room temperature and stirred for 1 hour. The reaction mixture was quenched with saturated aqueous NaHCO$_3$ and diluted with EtOAc. The organic layer was washed with brine, dried over MgSO$_4$, filtered, and concentrated under reduced pressure to give the crude material that was purified by silica gel flash column chromatography (100% CH$_2$Cl$_2$ to 1.5% MeOH in CH$_2$Cl$_2$) to afford 30 mg (99%) of the desired product.

Step J: Preparation of 4-(2-fluoro-4-(methylthio)phenylamino)-N-(2-hydroxyethoxy)-1-methyl-6-oxo-1,6-dihydropyridazine-3-carboxamide: To a solution of 4-(2-fluoro-4-(methylthio)phenylamino)-1-methyl-6-oxo-N-(2-(vinyloxy)ethoxy)-1,6-dihydropyridazine-3-carboxamide (30 mg, 0.077 mmol) in EtOH/THF (2 mL/2 mL) was added 1 N aqueous HCl (0.15 mL, 0.15 mmol, 1 N aqueous solution) at room temperature. The reaction mixture was stirred for 1 hour at room temperature. The reaction mixture was neutralized to pH 7, diluted with EtOAc (3×), washed with water, dried over MgSO$_4$, filtered, and concentrated under reduced pressure to give the crude material that was purified by silica gel flash column chromatography (100% EtOAc to 100% CH$_2$Cl$_2$ to 2.5 to 3 to 5% MeOH in CH$_2$Cl$_2$) to afford 6 mg (22%) of the desired product. MS APCI (−) m/z 367 (M−1) detected; −$^1$H NMR (400 MHz, CD$_3$OD) δ 7.35 (t, 1H), 7.18 (dd, 1H), 7.14 (dd, 1H), 5.92 (s, 1H), 4.06 (t, 2H), 3.79 (t, 2H), 3.74 (s, 3H), 2.51 (s, 3H).

Example 2

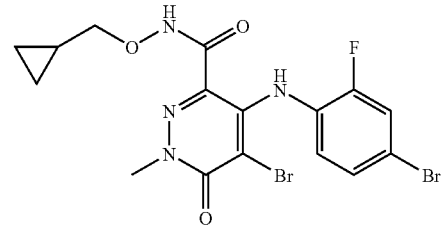

5-Bromo-4-(4-bromo-2-fluorophenylamino)-N-(cyclopropylmethoxy)-1-methyl-6-oxo-1,6-dihydropyridazine-3-carboxamide Step A: Preparation of methyl 4-(2-fluorophenylamino)-1-methyl-6-oxo-1,6-dihydropyridazine-3-carboxylate: The title compound was prepared in 61% yield by the procedure as previously described in Example 1 (step H) using methyl 4-chloro-1-methyl-6-oxo-1,6-dihydropyridazine-3-carboxylate (109 mg, 0.54 mmol, prepared as previously described in Example 1 (steps A-G) and 2-fluoroaniline (0.053 mL, 0.54 mmol).

Step B: Preparation of methyl 5-bromo-4-(4-bromo-2-fluorophenylamino)-1-methyl-6-oxo-1,6-dihydropyridazine-3-carboxylate: A mixture of methyl 4-(2-fluorophenylamino)-1-methyl-6-oxo-1,6-dihydropyridazine-3-carboxylate (88 mg, 0.32 mmol) and NBS (59 mg, 0.33 mmol) in DMF (1.5 mL) was stirred for 2 hours at room temperature. The reaction mixture was diluted with EtOAc and washed with water (2×). The organic layer was dried over $MgSO_4$, filtered, and concentrated under reduced pressure to give the crude material that was purified by silica gel flash column chromatography (100% $CH_2Cl_2$ to 0.5% MeOH in $CH_2Cl_2$) followed by additional silica gel flash column chromatography (30% EtOAc in $CH_2Cl_2$) to give 80 mg of a mixture of methyl 5-bromo-4-(2-fluorophenylamino)-1-methyl-6-oxo-1,6-dihydropyridazine-3-carboxylate and methyl 5-bromo-4-(4-bromo-2-fluorophenylamino)-1-methyl-6-oxo-1,6-dihydropyridazine-3-carboxylate. This mixture was re-submitted for bromination. To this mixture was added DMF (1.5 mL) followed by NBS (29 mg, 0.22 mmol) at room temperature. The reaction mixture was stirred for 2.5 hours at room temperature. Additional 15 mg of NBS was added and the reaction mixture was stirred for additional 20 hours at room temperature. The reaction mixture was diluted with EtOAc and washed with water (2×). The organic layer was dried over $MgSO_4$, filtered, and concentrated under reduced pressure to give the crude material that was purified by silica gel flash column chromatography (30% EtOAc in $CH_2Cl_2$) to afford 62 mg (64%) of the desired product.

Step C: Preparation of 5-bromo-4-(4-bromo-2-fluorophenylamino)-N-(cyclopropylmethoxy)-1-methyl-6-oxo-1,6-dihydropyridazine-3-carboxamide: The title compound was prepared in 40% yield by the procedure described in Example 1 (step 1) using methyl 5-bromo-4-(4-bromo-2-fluorophenylamino)-1-methyl-6-oxo-1,6-dihydropyridazine-3-carboxylate (31 mg, 0.071 mmol) and O-cyclopropylmethyl-hydroxylamine (20 mg, 0.23 mmol). MS APCI (−) m/z 487, 489, 491 (M−1, Br pattern) detected; $^1$H NMR (400 MHz, $CD_3OD$) δ 7.38 (dd, 1H), 7.31 (dd, 1H), 7.05 (t, 1H), 3.82 (s, 3H), 3.65 (d, 2H), 1.13 (m, 1H), 0.58 (q, 2H), 0.31 (q, 2H).

Example 3

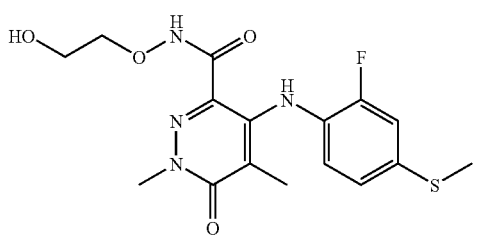

4-(2-Fluoro-4-(methylthio)phenylamino)-N-(2-hydroxyethoxy)-1,5-dimethyl-6-oxo-1,6-dihydropyridazine-3-carboxamide Step A: Preparation of N-methylpropionohydrazide: To a solution of methylhydrazine (27.6 mL, 508 mmol) and catalytic amount of DMAP in $CH_2Cl_2$ (130 mL) at 0° C. was added a solution of acetyl chloride (15.0 mL, 169 mmol) in $CH_2Cl_2$ (30 mL). The reaction mixture was warmed to room temperature and stirred for 16 hours. The white solids were filtered off and the filtrate was concentrated under reduced pressure to give the crude material that was purified by vacuum distillation to afford 8.25 g (48%) of the desired product (63-66° C. at 0.14 mm Hg).

Step B: Preparation of diethyl 2-(2-methyl-2-propionylhydrazono)malonate: A solution of N-methylpropionohydrazide (18.78 g, 183.9 mmol) and diethyl ketomalonate (56.1 mL, 368 mmol) in toluene (136 mL) was refluxed with a Dean-Stark trap for 4 hours. The reaction mixture was concentrated under reduced pressure to give the crude material that was purified by silica gel flash column chromatography (100% hexanes to 5 to 10% EtOAc in hexanes) to afford 23 g (49%) of the desired product.

Step C: Preparation of ethyl 4-hydroxy-1,5-dimethyl-6-oxo-1,6-dihydropyridazine-3-carboxylate: To a solution of LiHMDS (0.78 mL, 0.78 mmol, 1 M solution in THF) in THF (1 mL) at −78° C. was added a solution of diethyl 2-(2-methyl-2-propionylhydrazono)malonate (50 mg, 0.19 mmol) in THF (1 mL). The resulting mixture was slowly warmed to −40° C. and stirred for 1.5 hours at −40° C. The reaction mixture was quenched with 10% aqueous HCl and diluted with water. The resulting mixture was extracted with EtOAc (2×). The combined organic layers were washed with water, dried over $MgSO_4$, filtered, and concentrated under reduced pressure to give the crude material that was purified by silica gel flash column chromatography (100% hexanes to 20% EtOAc in hexanes) to afford 25 mg (61%) of the desired product.

Step D: Preparation of ethyl 4-chloro-1,5-dimethyl-6-oxo-1,6-dihydropyridazine-3-carboxylate: A mixture of ethyl 4-hydroxy-1,5-dimethyl-6-oxo-1,6-dihydropyridazine-3-carboxylate (1.85 g, 8.72 mmol) and $POCl_3$ (9 mL) was heated for 16 hours at 85° C. $POCl_3$ was removed under reduced pressure. Then the crude material was quenched with ice-water. The mixture was neutralized with saturated aqueous $NaHCO_3$ (pH ~6 to 7) and extracted with EtOAc (3×). The combined organic layers were dried over $MgSO_4$, filtered, and concentrated under reduced pressure to give the crude material that was purified by silica gel flash column chromatography (100% hexanes to 5 to 10 to 20% EtOAc in hexanes) to afford 1.72 g (86%) of the desired product.

Step E: Preparation of ethyl 4-(2-fluoro-4-(methylthio)phenylamino)-1,5-dimethyl-6-oxo-1,6-dihydropyridazine-3-carboxylate: The title compound was prepared in 81% yield by the procedure described in Example 1 (step H) using ethyl 4-chloro-1,5-dimethyl-6-oxo-1,6-dihydropyridazine-3-carboxylat (500 mg, 2.17 mmol) and 2-fluoro-4-methylthioaniline (375 mg, 2.38 mmol).

Step F: Preparation of 4-(2-fluoro-4-(methylthio)phenylamino)-N-(2-hydroxyethoxy)-1,5-dimethyl-6-oxo-1,6-dihydropyridazine-3-carboxamide: The title compound was prepared in 78% yield (2 steps) by the procedures described in Example 1 (steps I and J) using ethyl 4-(2-fluoro-4-(methylthio)phenylamino)-1,5-dimethyl-6-oxo-1,6-dihydropyridazine-3-carboxylate (50 mg, 0.14 mmol) and O-(2-vinyloxy-ethyl)-hydroxylamine (44 mg, 0.43 mmol). MS APCI (−) m/z 381 (M−1) detected; $^1$H NMR (400 MHz, $CD_3OD$) δ 7.10 (dd, 1H), 7.03 (dd, 1H), 6.87 (t, 1H), 3.99 (t, 2H), 3.79 (s, 3H), 3.74 (t, 2H), 2.47 (s, 3H), 1.74 (s, 3H).

The following compounds were prepared by the procedure as described in Example 1 (step 1) using ethyl 4-(2-fluoro-4-(methylthio)phenylamino)-1,5-dimethyl-6-oxo-1,6-dihydropyridazine-3-carboxylate and the appropriate hydroxylamine.

Example 4

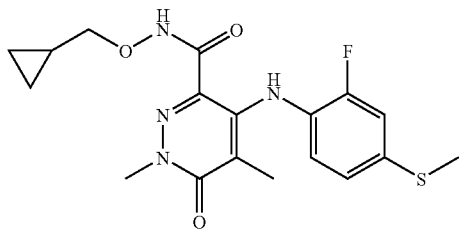

N-(Cyclopropylmethoxy)-4-(2-fluoro-4-(methylthio) phenylamino)-1,5-dimethyl-6-oxo-1,6-dihydropyridazine-3-carboxamide MS APCI (−) m/z 391 (M−1) detected; $^1$H NMR (400 MHz, CD$_3$OD) δ 7.09 (dd, 1H), 7.03 (dd, 1H), 6.86 (t, 1H), 3.78 (s, 3H), 3.71 (d, 2H), 2.47 (s, 3H), 1.75 (s, 3H) 1.16 (m, 1H), 0.58 (m, 2H), 0.31 (m, 2H).

Example 5

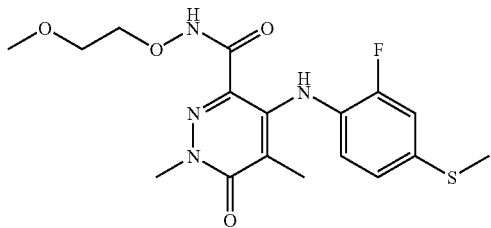

4-(2-Fluoro-4-(methylthio)phenylamino)-N-(2-methoxyethoxy)-1,5-dimethyl-6-oxo-1,6-dihydropyridazine-3-carboxamide MS APCI (−) m/z 395 (M−1) detected; $^1$H NMR (400 MHz, CD$_3$OD) δ 7.10 (dd, 1H), 7.03 (d, 1H), 6.87 (t, 1H), 4.05 (t, 2H), 3.78 (s, 3H), 3.64 (t, 2H), 3.37 (s, 3H), 2.47 (s, 3H), 1.74 (s, 3H).

Example 6

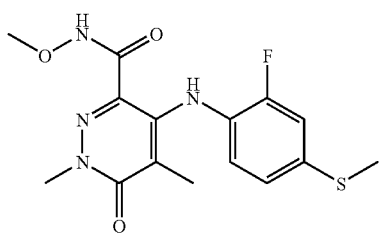

4-(2-Fluoro-4-(methylthio)phenylamino)-N-methoxy-1,5-dimethyl-6-oxo-1,6-dihydropyridazine-3-carboxamide MS APCI (−) m/z 351 (M−1) detected; $^1$H NMR (400 MHz, CD$_3$OD) δ 7.10 (d, 1H), 7.04 (d, 1H), 6.87 (t, 1H), 3.78 (s, 3H), 3.76 (s, 3H), 2.47 (s, 3H), 1.74 (s, 3H).

Example 7

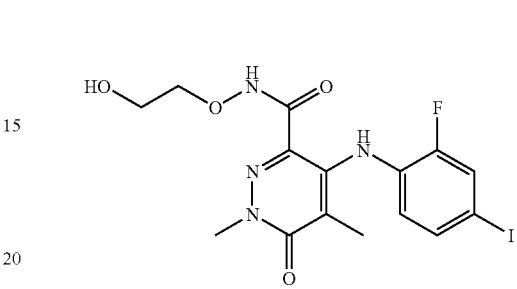

4-(2-Fluoro-4-iodophenylamino)-N-(2-hydroxyethoxy)-1,5-dimethyl-6-oxo-1,6-dihydropyridazine-3-carboxamide Step A: Preparation of 4-hydroxy-1,5-dimethyl-6-oxo-1,6-dihydropyridazine-3-carboxylic acid: To a solution of LiHMDS (331 mL, 331 mmol, 1 M solution in THF) in THF (430 mL) at −78° C. was added a solution of diethyl 2-(2-methyl-2-propionylhydrazono)malonate (21.40 g, 82.86 mmol) prepared by the procedure described in Example 3 (step B) in THF (10 mL). The resulting mixture was slowly warmed to −40° C. over 1 hour and stirred for 1.5 hours at −40° C. To the −40° C. reaction mixture was added water (500 mL). The reaction mixture was warmed to room temperature and stirred for 3 hours. The reaction mixture was concentrated under reduced pressure to remove the THF. The resulting aqueous mixture was quenched with 6 N aqueous HCl at 0° C., and acidified to pH 1 to 2. The resulting mixture was stirred for 16 hours at room temperature. The precipitates were filtered off and triturated with CH$_2$Cl$_2$ to afford 7.21 g (47%) of the desired product. The filtrate was extracted with EtOAc (3×). The combined organic layers were washed with water, dried over MgSO$_4$, filtered, and concentrated under reduced pressure to give the crude material that was triturated with CH$_2$Cl$_2$ to afford 3.56 g (23%) of additional desired product. The aqueous layer was extracted again with EtOAc (3×). The combined organic layers were washed with water, dried over MgSO$_4$, filtered, and concentrated under reduced pressure to give the crude material that was triturated with CH$_2$Cl$_2$ to afford 1.32 g (9%) of additional desired product. A total of 12.09 g (79%) of the desired product was obtained.

Step B: Preparation of 4-chloro-1,5-dimethyl-6-oxo-1,6-dihydropyridazine-3-carboxylic acid: A mixture of 4-hydroxy-1,5-dimethyl-6-oxo-1,6-dihydropyridazine-3-carboxylic acid (876 mg, 4.76 mmol) and POCl$_3$ (4.5 mL) was heated for 24 hours at 85° C. POCl$_3$ was removed under reduced pressure. The crude material was quenched with ice. The reaction mixture was stirred for 1 hour at room temperature. After removing solids by filtration, the aqueous filtrate was extracted with EtOAc (3×). The combined organic layers were dried over MgSO$_4$, filtered, and concentrated under reduced pressure to give. The recovered material was combined with the solids previously isolated and triturated with ether to afford 577 mg (60%) of the desired product.

Step C: Preparation of 4-(2-fluoro-4-iodophenylamino)-1,5-dimethyl-6-oxo-1,6-dihydropyridazine-3-carboxylic acid: To a suspension of 4-chloro-1,5-dimethyl-6-oxo-1,6-dihydropyridazine-3-carboxylic acid (200 mg, 0.99 mmol) and 2-fluoro-4-iodoaniline (478 mg, 1.97 mmol) in THF (6.5 mL) at −78° C. was slowly added a solution of LiHMDS (3.00 mL, 3.00 mmol, 1 M solution in THF). After complete addition, the resulting mixture was slowly warmed to room temperature and stirred for 4 hours. The reaction mixture was quenched with 6 N aqueous HCl (8 mL) at 0° C., warmed to room temperature, and stirred for 1.5 hours. The precipitates were filtered, washed with water and ether, and triturated with ether to afford 158 mg (38%) of the desired product.

Step D: Preparation of 4-(2-fluoro-4-iodophenylamino)-N-(2-hydroxyethoxy)-1,5-dimethyl-6-oxo-1,6-dihydropyridazine-3-carboxamide: To a suspension of 4-(2-fluoro-4-iodophenylamino)-1,5-dimethyl-6-oxo-1,6-dihydropyridazine-3-carboxylic acid (41 mg, 0.10 mmol) and HOBt (28 mg, 0.21 mmol) in DMF (1.5 mL) was added EDCI (40 mg, 0.21 mmol) at room temperature. The resulting mixture was stirred for 1.5 hours. O-(2-Vinyloxy-ethyl)-hydroxylamine (21 mg, 0.20 mmol) and TEA (0.030 mL, 0.22 mmol) was added to the activated ester at room temperature. After stirring for 1.5 hours, the reaction mixture was diluted with EtOAc and washed with saturated aqueous NH$_4$Cl, brine, saturated aqueous NaHCO$_3$ (2×), and brine. The organic layer was separated, dried over MgSO$_4$, filtered, and concentrated under reduced pressure to give 4-(2-fluoro-4-iodophenylamino)-1,5-dimethyl-6-oxo-N-(2-(vinyloxy)ethoxy)-1,6-dihydropyridazine-3-carboxamide that was used directly without further purification. The title compound was prepared by the procedure previously described in Example 1 (step J) using the crude 4-(2-fluoro-4-iodophenylamino)-1,5-dimethyl-6-oxo-N-(2-(vinyloxy)ethoxy)-1,6-dihydropyridazine-3-carboxamide (40% yield over two steps). MS APCI (−) m/z 461 (M−1) detected; $^1$H NMR (400 MHz, CD$_3$OD) δ 7.52 (dd, 1H), 7.44 (d, 1H), 6.63 (t, 1H), 3.98 (t, 2H), 3.80 (s, 3H), 3.74 (t, 2H), 1.78 (s, 3H).

The following compounds were prepared by the procedures as previously described in Example 7 (steps C and D) using the appropriate anilines and hydroxylamine. In some instances, a final deprotection step may be required. These deprotections can be accomplished by standard literature methods.

Example 8

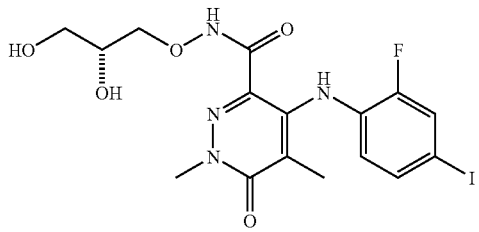

(R)—N-(2,3-Dihydroxypropoxy)-4-(2-fluoro-4-iodophenylamino)-1,5-dimethyl-6-oxo-1,6-dihydropyridazine-3-carboxamide MS APCI (−) m/z 491 (M−1) detected; $^1$H NMR (400 MHz, CD$_3$OD) δ 7.52 (dd, 1H), 7.44 (d, 1H), 6.63 (t, 1H), 4.02 (m, 1H), 3.88 (m, 2H), 3.80 (s, 3H), 3.59 (m, 2H), 1.77 (s, 3H).

Example 9

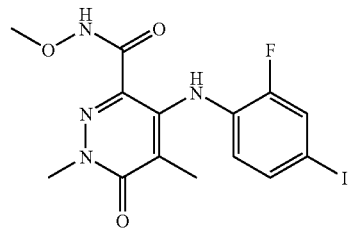

4-(2-Fluoro-4-iodophenylamino)-N-methoxy-1,5-dimethyl-6-oxo-1,6-dihydropyridazine-3-carboxamide MS APCI (−) m/z 431 (M−1) detected; $^1$H NMR (400 MHz, CD$_3$OD) δ 7.52 (dd, 1H), 7.44 (d, 1H), 6.63 (t, 1H), 3.79 (s, 3H), 3.75 (s, 3H), 1.77 (s, 3H).

Example 10

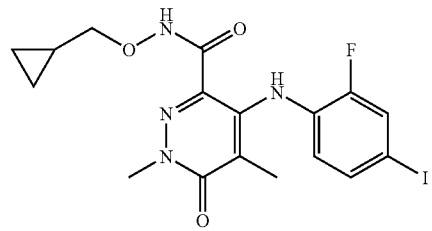

N-(Cyclopropylmethoxy)-4-(2-fluoro-4-iodophenylamino)-1,5-dimethyl-6-oxo-1,6-dihydropyridazine-3-carboxamide MS APCI (−) m/z 471 (M−1) detected; $^1$H NMR (400 MHz, CD$_3$OD) δ 7.51 (dd, 1H), 7.44 (d, 1H), 6.62 (t, 1H), 3.79 (s, 3H), 3.70 (d, 2H), 1.78 (s, 3H), 1.15 (m, 1H), 0.57 (q, 2H), 0.30 (q, 2H).

Example 11

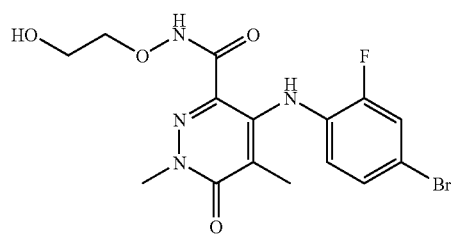

4-(4-Bromo-2-fluorophenylamino)-N-(2-hydroxyethoxy)-1,5-dimethyl-6-oxo-1,6-dihydropyridazine-3-carboxamide Step A: Preparation of diethyl 2-(2-methylhydrazono)malonate: To a solution of diethyl ketomalonate (95 g, 546 mmol) in EtOH (600 mL) (2 L 3-neck flask equipped with thermocouple, N₂ line, condenser and mechanical stirrer) was added MeNHNH₂ (32 mL, 600 mmol) in one portion at room temperature. The reaction mixture was warmed to 60° C. (internal temperature, heated by a heating mantle) and stirred for 6 hours. The reaction mixture was cooled to room temperature and stirred overnight. The reaction mixture was concentrated under reduced pressure to give the crude material along with solid precipitates that was purified by a silica gel plug (3:2 hexanes:EtOAc) to afford 81 g (74%) of the desired product.

Step B: Preparation of diethyl 2-(2-methyl-2-propionylhydrazono)malonate: To a solution of 2-(2-methylhydrazono)malonate (100 g, 494 mmol) in THF (1 L) at 0° C. was added LiHMDS (643 mL, 643 mmol) by an addition funnel over 45 minutes. The reaction mixture was stirred for 45 minutes at 0° C. Propionyl chloride (51.6 mL, 593 mmol) was added in one portion). The resulting mixture was warmed to room temperature and stirred for 20 hours. The reaction mixture was quenched with saturated aqueous NH₄Cl (85 mL) and water (85 mL). The reaction mixture was concentrated under reduced pressure and additional water (300 mL) was added. The resulting mixture was extracted with EtOAc (3×250 mL). The combined organic layers were washed with saturated aqueous NaHCO₃ (2×250 mL) followed by brine (250 mL), dried over MgSO₄, filtered, and concentrated under reduced pressure to give 112 g (88%) of the crude product that was used directly in the next step without further purification.

Step C: Preparation of 4-hydroxy-1,5-dimethyl-6-oxo-1,6-dihydropyridazine-3-carboxylic acid: To a solution of LiHMDS (331 mL, 331 mmol, 1 M solution in THF) in THF (430 mL) at −78° C. was added a solution of 2-(2-methyl-2-propionylhydrazono)malonate (21.40 g, 82.86 mmol) in THF (10 mL). The resulting mixture was slowly warmed to −40° C. over 1 hour and stirred for 1.5 hours at −40° C. To the reaction mixture was added water (500 mL) at −40° C. The reaction mixture was warmed to room temperature and stirred for 3 hours. The reaction mixture was concentrated under reduced pressure, quenched with 6 N aqueous HCl at 0° C., and acidified to pH 1 to 2. The resulting mixture was stirred for 16 hours at room temperature. The precipitates were filtered off and triturated with CH₂Cl₂ to afford 7.21 g (47%) of the desired product. The filtrate was extracted with EtOAc (3×). The combined organic layers were washed with water, dried over MgSO₄, filtered, and concentrated under reduced pressure to give the crude material that was triturated with CH₂Cl₂ to afford additional 3.56 g (23%) of the desired product. The aqueous layer was extracted again with EtOAc (3×). The combined organic layers were washed with water, dried over MgSO₄, filtered, and concentrated under reduced pressure to give the crude material that was triturated with CH₂Cl₂ to afford additional 1.32 g (9%) of the desired product. A total of 12.09 g (79%) of the desired product was obtained.

Step D: Preparation of 4-chloro-1,5-dimethyl-6-oxo-1,6-dihydropyridazine-3-carboxylic acid: A mixture of 4-hydroxy-1,5-dimethyl-6-oxo-1,6-dihydropyridazine-3-carboxylic acid (35.4 g, 192 mmol), catalytic amount of DMF (3 drop), and POCl₃ (178 mL, 1.92 mol) was heated for 2 days at 90° C., and then the POCl₃ was removed under reduced pressure. The crude material was quenched with ice, and the reaction mixture was stirred for 2 hours at room temperature. The precipitates formed out of the solution was filtered off and washed with ether. The precipitates collected were triturated with ether to afford 11.7 g (30%) of the desired product. The filtrate was extracted with EtOAc (2×). The combined organic layers were dried over MgSO₄, filtered, and concentrated under reduced pressure to give the crude product that was triturated with ether and dried under reduced pressure to afford additional 9.56 g (24%) of the desired product. A total of 21.29 g (55%) of the desired product was obtained.

Step E: Preparation of 4-(4-bromo-2-fluorophenylaminuteso)-1,5-dimethyl-6-oxo-1,6-dihydropyridazine-3-carboxylic acid: To a solution of 4-bromo-2-fluoroaniline (22.6 g, 116 mmol) in THF (165 mL) at −78° C. was slowly added a solution of LiHMDS (174 mL, 174 mmol, 1 M solution in THF). The resulting mixture was stirred for 1 hour at −78° C. To this mixture was added 4-chloro-1,5-dimethyl-6-oxo-1,6-dihydropyridazine-3-carboxylic acid (11.0 g, 54.4 mmol) as a solid at −78° C. The reaction mixture was slowly warmed to room temperature and stirred for 21 hour. The reaction was quenched and acidified with 10% aqueous HCl (250 mL) at 0° C. To this mixture was added water (100 mL), EtOAc (350 mL), and brine (50 mL). The reaction mixture was warmed to room temperature and stirred for 30 minutes. The organic layer was separated and the acidic aqueous layer was extracted with EtOAc (2×300 mL). The combined organic layers were dried over MgSO₄, filtered, and concentrated under reduced pressure to give the crude material that was triturated with ether (5×), filtered, washed with ether, and dried under reduced pressure to afford 14.51 g (75%) of the desired product.

Step F: Preparation of 4-(4-bromo-2-fluorophenylaminuteso)-1,5-dimethyl-6-oxo-N-(2-(vinyloxy)ethoxy)-1,6-dihydropyridazine-3-carboxamide: To a suspension of 4-(4-bromo-2-fluorophenylaminuteso)-1,5-dimethyl-6-oxo-1,6-dihydropyridazine-3-carboxylic acid (14.51 g, 40.74 mmol) and HOBt (11.01 g, 81.48 mmol) in DMF (165 mL) was added EDCI (15.62 g, 81.48 mmol) at room temperature. The resulting mixture was stirred for 1.5 hours. O-(2-(Vinyloxy)ethyl)hydroxylamine (8.36 mL, 81.48 mmol) and TEA (11.36 mL, 81.48 mmol) was added to the activated ester at room temperature. After stirring for 1.5 hours, the reaction mixture was diluted with EtOAc and washed with saturated aqueous NH₄Cl, brine, saturated aqueous NaHCO₃ (2×), and brine. The organic layer was separated, dried over MgSO₄, filtered, and concentrated under reduced pressure to give the crude product that was used directly without further purification.

Step G: Preparation of 4-(4-bromo-2-fluorophenylaminuteso)-N-(2-hydroxyethoxy)-1,5-dimethyl-6-oxo-1,6-dihydropyridazine-3-carboxamide: A mixture of 4-(4-bromo-2-fluorophenylaminuteso)-1,5-dimethyl-6-oxo-N-(2-(vinyloxy)ethoxy)-1,6-dihydropyridazine-3-carboxamide (17.98 g, 40.75 mmol) and 6 N aqueous HCl (13.58 mL, 81.50 mmol) in EtOH/THF (50 mL/50 mL) was stirred for 3 hours at room temperature. The reaction mixture was concentrated under reduced pressure and diluted with water (50 mL). The resulting mixture was extracted with EtOAc (2×). The combined organic layers were dried over MgSO₄, filtered, and concentrated under reduced pressure to give the crude material that was purified by silica gel flash column chromatography (100% CH₂Cl₂ to 2.5% MeOH in CH₂Cl₂) to afford 9.41 g (56% for two steps) of the desired product. MS APCI (−) m/z 413, 415 (M−1, Br pattern) detected; $^1$H NMR (400 MHz, CD₃OD) δ 7.38 (dd, 1H), 7.27 (d, 1H), 6.79 (t, 1H), 3.99 (t, 2H), 3.80 (s, 3H), 3.74 (t, 2H), 1.77 (s, 3H).

MS APCI (−) m/z 413, 415 (M−1, Br pattern) detected; $^1$H NMR (400 MHz, CD₃OD) δ 7.38 (dd, 1H), 7.27 (d, 1H), 6.79 (t, 1H), 3.99 (t, 2H), 3.80 (s, 3H), 3.74 (t, 2H), 1.77 (s, 3H).

Example 12

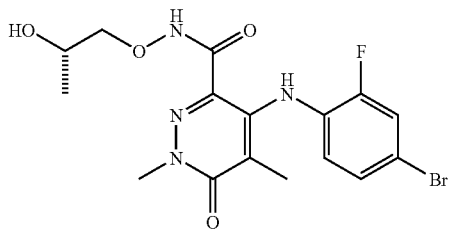

(S)-4-(4-Bromo-2-fluorophenylamino)-N-(2-hydroxypropoxy)-1,5-dimethyl-6-oxo-1,6-dihydropyridazine-3-carboxamide MS APCI (−) m/z 427, 429 (M−1, Br pattern) detected; $^1$H NMR (400 MHz, CD$_3$OD) δ 7.39 (dd, 1H), 7.27 (dd, 1H), 6.79 (t, 1H), 3.98 (m, 1H), 3.84 (dd, 1H), 3.80 (s, 3H), 3.72 (dd, 1H), 1.78 (s, 3H), 1.15 (d, 3H).

Example 13

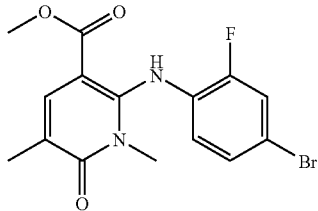

Methyl 2-(4-bromo-2-fluorophenylamino)-1,5-dimethyl-6-oxo-1,6-dihydropyridine-3-carboxylate Step A. Preparation of 2-chloro-6-oxo-1,6-dihydro-pyridine-3-carboxylic acid: 2-Chloro-6-oxo-1,6-dihydro-pyridine-3-carboxylic acid was prepared from dichloronicotinic acid (3.00 g, 15.6 mmol, Aldrich) according to the procedure described in U.S. Pat. No. 3,682,932 to yield 1.31 g (48%) of the desired product.

Step B. Preparation of 2-chloro-1-methyl-6-oxo-1,6-dihydro-pyridine-3-carboxylic acid methyl ester: To a solution of 2-chloro-6-oxo-1,6-dihydro-pyridine-3-carboxylic acid (0.644 g, 3.71 mmol) in DMF (20 mL) was added lithium hydride (95%, 0.078 g, 9.28 mmol) and the reaction mixture was stirred for 40 minutes under N$_2$. Methyl iodide (0.508 mL, 1.16 g, 8.16 mmol) was then added and the reaction mixture was stirred for an additional 45 minutes. The reaction mixture was quenched with 2 M HCl until the pH was 6-7. The reaction mixture was diluted with EtOAc and saturated NaCl and the layers separated. The aqueous layer was back extracted with EtOAc (1×). The combined organic layers were dried (Na$_2$SO$_4$) and concentrated under reduced pressure to yield a crude yellow solid. HPLC analysis showed two products in a 4:1 ratio that were separated by flash column chromatography (methylene chloride/EtOAc, 15:1 to 10:1) to give 0.466 g (62%) pure desired product as a white crystalline solid. The minor product was also isolated as a pale yellow crystalline solid and identified as the regioisomer 2-chloro-6-methoxy-nicotinic acid methyl ester.

Step C. Preparation of methyl 5-bromo-2-chloro-1-methyl-6-oxo-1,6-dihydropyridine-3-carboxylate: To a solution of methyl 2-chloro-1-methyl-6-oxo-1,6-dihydropyridine-3-carboxylate (0.100 g, 0.496 mmol) in DMF (5 mL) was added N-bromosuccinimide (0.177 g, 0.992 mmol) and the reaction mixture was stirred for 4 hours at room temperature under N$_2$. The reaction mixture was quenched with saturated sodium bisulfite and then diluted with EtOAc and H$_2$O and the layers separated. The aqueous layer was back extracted with EtOAc (2×). The combined organic layers were dried (Na$_2$SO$_4$) and concentrated under reduced pressure to yield a yellow solid in quantitative yield.

Step D. Preparation of methyl 2-chloro-1,5-dimethyl-6-oxo-1,6-dihydropyridine-3-carboxylate: To a suspension of methyl 5-bromo-2-chloro-1-methyl-6-oxo-1,6-dihydropyridine-3-carboxylate (0.400 g, 1.43 mmol) and 1,1'-bis(diphenylphosphino)ferrocenedichloropalladium(II) (0.0587 g, 0.0713 mmol) in dioxane (8 mL) at 0° C. under N$_2$ was added dimethylzinc (0.713 mL, 1.43 mmol, 2 M solution in toluene). The reaction mixture was immediately heated to 100° C. for 30 minutes. The reaction mixture was cooled to 0° C. and quenched with MeOH (0.800 mL). The reaction mixture was diluted with EtOAc and washed with 1 M HCl. The aqueous layer was back extracted with EtOAc (1×). The combined organic layers were washed with saturated NaCl, dried (Na$_2$SO$_4$) and concentrated under reduced pressure to a dark yellow gum. Purification by flash column chromatography (methylene chloride/EtOAc, 15:1) gave 0.164 g (53%) pure desired product as a yellow crystalline solid.

Step E: Preparation of methyl 2-(4-bromo-2-fluorophenylamino)-1,5-dimethyl-6-oxo-1,6-dihydropyridine-3-carboxylate: To a solution of 4-bromo-2-fluorobenzenamine (0.058 g, 0.31 mmol) in THF (2 mL) at −78° C. under N$_2$ was added lithium bis(trimethylsilyl)amide (0.56 mL, 0.56 mmol, 1 M solution in hexanes) dropwise. The reaction mixture was stirred for one hour at −78° C. Methyl 2-chloro-1,5-dimethyl-6-oxo-1,6-dihydropyridine-3-carboxylate (0.060 g, 0.28 mmol) was then added dropwise as a solution in THF (1 mL) and the reaction mixture was stirred for 25 minutes at −78° C. The reaction mixture was quenched by the addition of H$_2$O and the pH was adjusted with 0.1M HCl and then diluted with EtOAc and saturated NaCl and the layers separated. The aqueous layer was back extracted with EtOAc (1×). The combined EtOAc layers were dried (Na$_2$SO$_4$) and concentrated under reduced pressure. Purification by flash column chromatography (methylene chloride/EtOAc, 20:1) gave 0.086 g (84%) pure desired product as a white crystalline solid. MS ESI (+) m/z 371, 373 (M+, Br pattern) detected; $^1$H NMR (400 MHz, CDCl$_3$) δ 9.57 (s, 1H), 7.79 (s, 1H), 7.32 (d, 1H), 7.18 (d, 1H), 6.58 (t, 1H), 3.85 (s, 3H), 3.29 (s, 3H), 2.14 (s, 3H).

Example 14

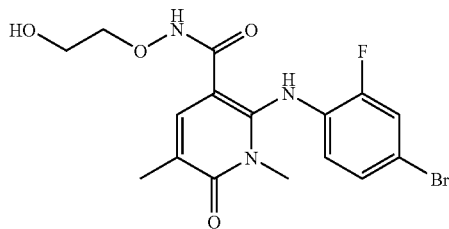

2-(4-Bromo-2-fluorophenylamino)-N-(2-hydroxyethoxy)-1,5-dimethyl-6-oxo-1,6-dihydropyridine-3-carboxamide Step A: Preparation of 2-(4-bromo-2-fluorophenylamino)-1,5-dimethyl-6-oxo-N-(2-(vinyloxy)ethyl)-1,6-dihydropyridine-3-carboxamide: To a solution of methyl 2-(4-bromo-2-fluorophenylamino)-1,5-dimethyl-6-oxo-1,6-dihydropyridine-3-carboxylate (0.060 g, 0.16 mmol) in THF (2 mL) was added O-(2-vinyloxy-ethyl)-hydroxylamine (0.042 ml, 0.41 mmol). The solution was cooled to 0° C. and lithium bis(trimethylsilyl)amide (0.81 ml, 0.81 mmol, 1 M solution in hexanes) was added dropwise. The reaction mixture was warmed to room temperature. After stirring for 35 minutes the reaction mixture was quenched by the addition of saturated NaHCO$_3$ and partitioned between EtOAc and saturated NaCl. The layers were separated and the organic layer was dried (Na$_2$SO$_4$) and concentrated under reduced pressure. Purification by flash column chromatography (methylene chloride/MeOH, 20:1) gave 0.067 g (94%) pure desired product as an off-white crystalline solid.

Step B: Preparation of 2-(4-bromo-2-fluorophenylamino)-N-(2-hydroxyethoxy)-1,5-dimethyl-6-oxo-1,6-dihydropyridine-3-carboxamide: To a solution of 2-(4-bromo-2-fluorophenylamino)-1,5-dimethyl-6-oxo-N-(2-(vinyloxy)ethoxy)-1,6-dihydropyridine-3-carboxamide (0.067 g, 0.150 mmol) in ethanol (2 mL) was added aqueous 2 M HCl (0.380 mL, 0.760 mmol). The reaction mixture was stirred for 16 hours at room temperature. The pH of the reaction mixture was adjusted with 1 M NaOH. The reaction mixture was diluted with EtOAc and H$_2$O. The organic layer was separated and washed with saturated NaCl. The combined aqueous layers were back extracted with EtOAc (1×). The combined organic layers were dried (Na$_2$SO$_4$) and concentrated under reduced pressure to yield 0.060 g (94%) pure desired product as an off-white crystalline solid. MS ESI (+) m/z 414, 416 (M+, Br pattern detected); $^1$H NMR (400 MHz, CDCl$_3$) δ 9.80 (s, 1H), 8.44 (s, 1H), 7.31 (d, 1H), 7.19 (d, 1H), 6.59 (t, 1H), 4.05 (m, 2H), 3.85 (m, 1H), 3.75 (m, 2H), 3.29 (s, 3H), 2.15 (s, 3H).

The following compounds were prepared using the methods as described in Examples 13 and 14. In some instances, such as Example 14, a final deprotection step may be required. These deprotections can be accomplished by standard literature methods.

Example 15

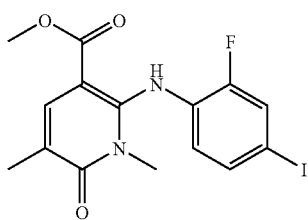

Methyl 2-(2-fluoro-4-iodophenylamino)-1,5-dimethyl-6-oxo-1,6-dihydropyridine-3-carboxylate Methyl 2-chloro-1,5-dimethyl-6-oxo-1,6-dihydropyridine-3-carboxylate was converted to methyl 2-(2-fluoro-4-iodophenylamino)-1,5-dimethyl-6-oxo-1,6-dihydropyridine-3-carboxylate following the procedure described in Step E of Example 13 using 2-fluoro-4-iodobenzenamine to yield the desired product as a white crystalline solid. MS ESI (+) m/z 417 (M+1) detected; $^1$H NMR (400 MHz, CDCl$_3$) δ 9.56 (s, 1H), 7.79 (s, 1H), 7.49 (d, 1H), 7.36 (d, 1H), 6.43 (t, 1H), 3.85 (s, 3H), 3.30 (s, 3H), 2.15 (s, 3H).

Example 16

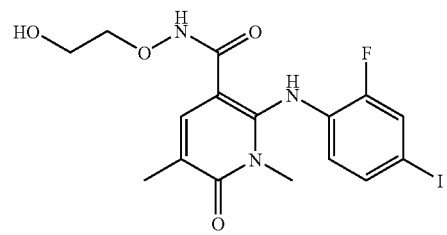

2-(2-fluoro-4-iodophenylamino)-N-(2-hydroxyethoxy)-1,5-dimethyl-6-oxo-1,6-dihydropyridine-3-carboxamide Step A: Preparation of 2-(2-fluoro-4-iodophenylamino)-1,5-dimethyl-6-oxo-N-(2-(vinyloxy)ethyl)-1,6-dihydropyridine-3-carboxamide: To a solution of methyl 2-(2-fluoro-4-iodophenylamino)-1,5-dimethyl-6-oxo-1,6-dihydropyridine-3-carboxylate (0.500 g, 1.20 mmol) in THF (60 mL) was added O-(2-vinyloxy-ethyl)-hydroxylamine (0.149 g, 1.44 mmol). The solution was cooled to 0° C. and lithium bis(trimethylsilyl)amide (4.81 ml, 4.81 mmol) (1 M solution in hexanes) was added dropwise. The reaction mixture was warmed to room temperature. After stirring for 10 minutes the reaction mixture was quenched by the addition of 1 M HCl and partitioned between EtOAc and saturated NaCl. The layers were separated and the organic layer was dried (Na$_2$SO$_4$) and concentrated under reduced pressure to yield a crude yellow solid that was used without purification in the next step.

Step B: Preparation of 2-(2-fluoro-4-iodophenylamino)-N-(2-hydroxyethoxy)-1,5-dimethyl-6-oxo-1,6-dihydropyridine-3-carboxamide: To a solution of crude 2-(2-fluoro-4-iodophenylamino)-1,5-dimethyl-6-oxo-N-(2-(vinyloxy)ethoxy)-1,6-dihydropyridine-3-carboxamide (0.585 g, 1.20 mmol) in ethanol (10 mL) was added aqueous 2 M HCl (3 mL). The reaction mixture was stirred for 45 minutes at room temperature. The pH of the reaction mixture was adjusted to pH 7 with 1 M NaOH. The reaction mixture was diluted with EtOAc and H$_2$O. The organic layer was separated and washed with saturated NaCl. The combined aqueous layers were back extracted with EtOAc (1×). The combined organic layers were dried (Na$_2$SO$_4$) and concentrated under reduced pressure. Purification by silica gel flash column chromatography (methylene chloride/MeOH, 15:1) gave 2-(2-fluoro-4-iodophenylamino)-1,5-dimethyl-6-oxo-N-(2-(vinyloxy)ethoxy)-1,6-dihydropyridine-3-carboxamide (0.421 g; 76% over two steps) as a pale yellow solid. MS ESI (+) m/z 462 (M+1) pattern detected; $^1$H NMR (400 MHz, CDCl$_3$) δ 9.77 (s, 1H), 8.50 (s, 1H), 7.47 (d, 1H), 7.36 (m, 1H), 6.43 (t, 1H), 4.04 (br s, 2H), 3.85 (br s, 1H), 3.74 (br s, 2H), 3.29 (s, 3H), 2.14 (s, 3H). MS ESI (+) m/z 462 (M+1) pattern detected.

Example 16A

Preparation of Form 1, 2-(2-fluoro-4-iodophenylamino)-N-(2-hydroxyethoxy)-1,5-dimethyl-6-oxo-1,6-dihydropyridine-3-carboxamide

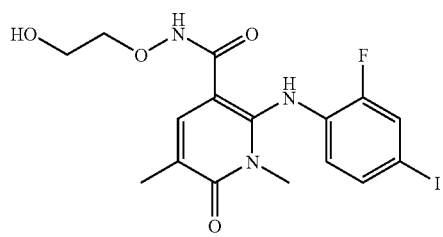

Step 1: Preparation of 2-(2-Fluoro-4-iodo-phenylamino)-1,5-dimethyl-6-oxo-1,6-dihydro-pyridine-3-carboxylic acid methyl ester: To a stirred solution of 2-fluoro-4-iodoaniline (182 g, 0.77 mol) in THF (5.25 L) at −45° C. under nitrogen was added 1M lithium bis(trimethylsilyl)amide solution in hexanes (1260 g), over 28 minutes at −43 to −41.6° C. After 1 hour, 2-chloro-1,5-dimethyl-6-oxo-1,6-dihydropyridine-3-carboxylic acid methyl ester (155 g, 0.72 mol) in THF (1.05 L) was added over 43 minutes. The mixture was held for 1 hour 55 minutes at −46° C., then allowed to warm to −13° C. and quenched with water (186 mL, 10.3 mol) over 5 minutes, maintaining the temperature between −13° C. and −11° C. The mixture was then allowed to warm to 0° C. over 30 minutes. 2M HCl was then added over 1 hour until pH 7-8 was achieved (1855 mL added). After standing overnight the mixture was allowed to warm to ambient temperature, and sodium chloride solution (1 L, 15% w/v) was added. The lower (aqueous layer) was discarded and the THF layer was concentrated by distillation to approx 1.4 L. Iso-hexane (4.65 L) was added to the mixture at approximately 52° C. over 1 hour 15 minutes, and then the mixture was cooled to 20° C. over 3 hours. After 1 hour at 20° C., the mixture was cooled to 0° C. and held at this temperature overnight. The reaction mixture was then filtered, and the solid was washed with chilled iso-hexane (5° C.) (2×1.25 L). The solid was dried in a vacuum oven at 45° C. to provide 2-(2-fluoro-4-iodophenylamino)-1,5-dimethyl-6-oxo-1,6-dihydropyridine-3-carboxylic acid methyl ester (248 g, 0.60 mol, 83% yield). $^1$H NMR (D$_6$-DMSO): δ 7.75 (d, 1H, J 1 Hz, ArH), 7.68 (dd, 1H, J 11, 2 Hz, ArH), 7.42 (d, 1H, J 8.5 Hz, ArH), 6.62 (~t, 1H, J 8.5 Hz, ArH), 3.69 (s, 3H, OCH$_3$), 3.22 (s, 3H, NCH$_3$), 2.03 (s, 3H, ArCH$_3$).

Step 2: Preparation of 2-(2-fluoro-4-iodophenylamino)-1,5-dimethyl-6-oxo-1,6-dihydropyridine-3-carboxylic acid (2-vinyloxy-ethoxy)-amide: To a stirred solution of 2-(2-fluoro-4-iodophenylamino)-1,5-dimethyl-6-oxo-1,6-dihydropyridine-3-carboxylic acid methyl ester (221 g, 0.53 mol) and O-(2-vinyloxyethyl)-hydroxylamine (63 g, 0.61 mol) in THF (2.85 L), under nitrogen, was added 1M lithium bis(trimethylsilylamide) solution in hexanes (1431 g), over 55 minutes, keeping the temperature between −14.7 and −12.4° C. After 2 hours at −15° C., water (165 mL, 9.2 mol) was added to the mixture, followed by 2M HCl solution (1.98 L), which was added over 20 minutes. The mixture was then allowed to warm to 22° C. and the lower aqueous phase (2.25 L) was separated and discarded. The organic phase was washed with sodium chloride solution (15% w/w, 1100 mL) and the volume was reduced to approximately 1.75 L by distillation of 2.25 L of solvent at ambient pressure. Iso-hexane (3.35 L) was added to the mixture over 2.5 hours with the temperature held at approximately 58° C. After a further 1 hour at this temperature the mixture was cooled to 20° C., held for 1 hour and then cooled to 0° C. and held at this temperature overnight. A further quantity of iso-hexane (500 mL) was added and the mixture was held for 1 hour, then more iso-hexane (500 mL) was added. After 45 minutes at 0° C. the slurry was filtered and the solid was washed with chilled iso-hexane (1.1 L) then dried in vacuum oven at 30° C. to provide 2-(2-fluoro-4-iodophenylamino)-1,5-dimethyl-6-oxo-1,6-dihydropyridine-3-carboxylic acid (2-vinyloxyethoxy)-amide (190 g, 0.39 mol, 74% yield). $^1$H NMR (D$_6$-DMSO): δ 7.63 (dd, 1H, J 11, 2 Hz, ArH), 7.52 (s, 1H, ArH), 7.38 (d, 1H, J 8.5 Hz, ArH), 6.55-6.46 (m, 2H, ArH/OCH=CH$_2$), 4.18 (dd, 1H, J 14, 2 Hz, OCH=CH$_2$), 3.99 (dd, 1H, J 7, 2 Hz, OCH=CH$_2$), 3.90-3.88 (m, 2H, OCH$_2$), 3.81-3.79 (m, 2H, OCH$_2$), 3.25 (s, 3H, NCH$_3$), 2.02 (s, 3H, ArCH$_3$).

Step 3: Preparation of Form 2, 2-(2-fluoro-4-iodophenylamino)-N-(2-hydroxyethoxy)-1,5-dimethyl-6-oxo-1,6-dihydropyridine-3-carboxamide: To a stirred solution of 2-(2-fluoro-4-iodophenylamino)-1,5-dimethyl-6-oxo-1,6-dihydropyridine-3-carboxylic acid (2-vinyloxyethoxy)-amide (170 g, 0.35 mol), under nitrogen, in THF (850 mL) was added 2M HCl (318 mL), over 15 minutes at 17-22° C. After 1 hour the reaction was complete (as indicated by HPLC) and a solution of 2M sodium hydroxide (318 mL) was added, over 10 minutes, keeping the temperature at approximately 22° C. The pH of the mixture was approximately 8. The mixture was then partitioned with MIBK (1.02 L) and the lower aqueous layer was separated and discarded. The volume of the organic solution was then reduced by distillation, at ambient pressure and with a jacket temperature of 85-95° C. After the removal of 750 mL solvent the rate of distillation had slowed considerably and the mixture was cooled to approximately 22° C. Crystalline 2-(2-fluoro-4-iodophenylamino)-N-(2-hydroxyethoxy)-1,5-dimethyl-6-oxo-1,6-dihydropyridine-3-carboxamide Form 2 (1 g, seed, prepared as described in Example 16C) was added to the mixture followed by ethyl acetate (170 mL). After 5 minutes the mixture began to crystallize and iso-hexane (1.7 L) was added at 23-25° C. over 50 minutes. The slurry was held at 25° C. for 80 minutes and then filtered. The solid was washed with iso-hexane (680 mL) then dried in vacuum oven at 30° C. to provide the title material (147 g, 0.31 mol, 89% yield). $^1$H NMR (D$_6$-DMSO): δ 7.63 (dd, 1H, J 11, 2 Hz, ArH), 7.55 (s, 1H, ArH), 7.38 (d, 1H, J 8.5 Hz, ArH), 6.52 (~t, 1H, J 8.5 Hz, ArH), 4.91-4.35 (bs, 1H, OH), 3.74 (t, 2H, J 5 Hz, OCH$_2$), 3.51 (~t, 2H, J 5 Hz, OCH$_2$), 3.25 (s, 3H, NCH$_3$), 2.02 (s, 3H, ArCH$_3$). MS (ESI) (+) m/z 484 (27%, [M+Na]$^+$), 462 (100%, [M+H]$^+$), 385 (8%), 100 (26%).

Step 4: Preparation of Form 1, 2-(2-fluoro-4-iodophenylamino)-N-(2-hydroxyethoxy)-1,5-dimethyl-6-oxo-1,6-dihydropyridine-3-carboxamide: To a stirred slurry of the product from Step 3 (123 g) in ethyl acetate (2.0 L), at 50° C., was added Form 1, 2-(2-fluoro-4-iodophenylamino)-N-(2-hydroxyethoxy)-1,5-dimethyl-6-oxo-1,6-dihydropyridine-3-carboxamide (4.9 g) (prepared as described in step 5) and residual material was washed into the vessel with ethyl acetate (0.45 L). The mixture was held at this temperature for 64 hours. Analysis of a sample indicated that the material was mainly Form 2. After a further 1 hour the temperature of the mixture was increased to 60° C., and after 6 hours at this temperature a further 3.25 g of Form 1, 2-(2-fluoro-4-iodophenylamino)-N-(2-hydroxyethoxy)-1,5-dimethyl-6-oxo-1,6-dihydropyridine-3-carboxamide (prepared as described in Example 16D) was added and washed in with ethyl acetate (100 mL). Stirring at 60° C. was continued for a further 16 hours, after which time analysis indicated that some Form 2 remained. The volume of the mixture was then reduced by distillation of solvent (780 mL removed), at 52° C. batch temperature and 400 mbar. Stirring at 60° C. was then continued overnight and the mixture was re-analyzed, but analysis indicated that some Form 2 still remained. After a further 7 hours an extra baffle was placed in the reactor and stirring was continued until the following day. More ethyl acetate (0.5 L) was then added to aid the efficiency of agitation and the mixture was held for a further 2 hours at 60° C. A sample taken at this point was found to be Form 1. In total the time taken for the turnover from Form 2 to Form 1 was 143 hours. The material held overnight at 50° C., then cooled to 12° C. and filtered. The filter cake was washed with ethyl acetate (400 mL) at 12° C., then dried in vacuum oven over a weekend (68 hours) at 35° C. to provide Form 1, 2-(2-fluoro-4-iodophenylamino)-N-(2-hydroxyethoxy)-1,5-dimethyl-6-oxo-1,6-dihydropyridine-3-carboxamide (109 g).

Example 16B

Preparation of Form 1, 2-(2-fluoro-4-iodophenylamino)-N-(2-hydroxyethoxy)-1,5-dimethyl-6-oxo-1,6-dihydropyridine-3-carboxamide To a rapidly stirred mixture of 2-(2-fluoro-4-iodophenylamino)-1,5-dimethyl-6-oxo-1,6-dihydropyridine-3-carboxylic acid (2-vinyloxyethoxy)-amide (4.2 g, 8.52 mmol) (prepared according to Example 16A, Step 2) above in ethyl acetate (126.00 mL) was added hydrogen chloride (17.05 mL, 17.0493 g, 17.05 mmol). After 2 hours, less than 1% of the starting material remained (by HPLC analysis) and the phases were allowed to settle. The lower aqueous phase was separated and discarded and the organic phase was washed with sodium chloride (42 mL, 15% wt/vol, then 2×25 mL, 9% wt/vol). The volume was then reduced by distillation of solvent (44 mL) at atmospheric pressure (65° C. head temperature). The solution was then cooled to 70° C., and Form 1, 2-(2-fluoro-4-iodophenylamino)-N-(2-hydroxyethoxy)-1,5-dimethyl-6-oxo-1,6-dihydropyridine-3-carboxamide (40.3265 mg), made according to Example 16A, Step 4, was added. The mixture was stirred for 20 hours at 70° C. The temperature was reduced to 24° C. over 4 hours 15 minutes, and then lowered to 1° C. for 1 hour. The slurry was then filtered, the cake was washed with cold ethyl acetate (17 mL) and the solid was dried in a vacuum oven at 45° C., to provide 2-(2-fluoro-4-iodophenylamino)-N-(2-hydroxyethoxy)-1,5-dimethyl-6-oxo-1,6-dihydropyridine-3-carboxamide Form 1 (3.15 g, 76%).

Example 16C

Preparation of 2-(2-fluoro-4-iodophenylamino)-N-(2-hydroxyethoxy)-1,5-dimethyl-6-oxo-1,6-dihydropyridine-3-carboxamide Form 2

A mixture of 2-(2-fluoro-4-iodophenylamino)-1,5-dimethyl-6-oxo-1,6-dihydro-pyridine-3-carboxylic acid (2-vinyloxy-ethoxy)-amide (500 mg, 915 µmol) and hydrogen chloride (1 mL) in tetrahydrofuran (5 mL) was stirred overnight. Sodium hydroxide (1M, 2.00 mL) was then added, and after a further 10 minutes methyl isobutyl ketone (3 mL) and ethyl acetate (3 mL) were added to the mixture. The layers were separated and the organic solution was washed with 50% brine (4 mL), then evaporated (approximately half the material was lost by spillage). The residue was taken up in methyl isobutyl ketone (3 mL) and ethyl acetate (1 mL) and the mixture was heated to reflux. Upon cooling to 50° C. the mixture went cloudy and isohexane (5 mL) was added. This caused solid to crystallize and the mixture was cooled to 20° C., followed by a further addition of isohexane (5 mL). The solid was then filtered, washed with isohexane (1 mL) and dried in a vacuum oven at 40° C., to provide the title compound, 140 mg.

Example 16D

Preparation of Form 1, 2-(2-fluoro-4-iodophenylamino)-N-(2-hydroxyethoxy)-1,5-dimethyl-6-oxo-1,6-dihydropyridine-3-carboxamide The final product from Example 16 (25 mg) was placed in a Syn 10 (Radleys) reaction tube together with a magnetic stirrer, and the material was dissolved in methanol by the addition of one aliquot (1 mL) of methanol preheated to 50° C. with stirring. A further 5 mg of methanol was added to the reaction tube to ensure a super-saturated solution was produced on cooling. When the majority of the solid had dissolved, the resultant solution was filtered through a Pall 0.45 µm PTFE Acrodisc CR13 filter into a second tube at 50° C. in the Syn 10. The tube was then cooled to 0° C. at a rate of 3° C./min and held at 0° C. until the material had crystallized. The samples were filtered off, dried by suction then by standing in ambient conditions. The solids were carefully removed from the filter paper and examined by XRPD.

Example 16E

X-Ray Powder Diffraction (PXRD)

The X-ray powder diffraction patterns of Form 1 and Form 2 of 2-(2-fluoro-4-iodophenylamino)-N-(2-hydroxyethoxy)-1,5-dimethyl-6-oxo-1,6-dihydropyridine-3-carboxamide were determined by mounting a sample of the crystalline material on Siemens single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 Angstroms using a Bruker D5000 powder X-ray diffractometer (Bruker AXS, Banner Lane Coventry CV4 9 GH). The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The instrument was equipped with a scintillation counter as detector. Control and data capture was by means of a Dell Optiplex 686 NT 4.0 Workstation operating with Diffract+ software. Data were collected over the range 2-theta 2-40°, in increments of 2-theta 0.02° with 4 s per increment.

The skilled person is aware that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, the skilled person will realize that the relative intensity of peaks can be affected by, for example, grains above 30 microns in size and non-unitary aspect ratios, which may affect analysis of samples. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline form of 2-(2-fluoro-4-iodophenylamino)-N-(2-hydroxyethoxy)-1,5-dimethyl-6-oxo-1,6-dihydropyridine-3-carboxamide is not limited to the crystals that provide X-ray powder diffraction patterns identical to the X-ray powder diffraction patterns shown in FIGS. 10 to 13 and any crystals providing X-ray powder diffraction patterns substantially the same as that shown in FIGS. 10 to 13 fall within the scope of the present invention. A person skilled in the art of X-ray powder diffraction is able to judge the substantial identity of X-ray powder diffraction patterns.

Example 16F

Differential Scanning Calorimetry

Differential Scanning Calorimetry (DSC) analysis was conducted on 2-(2-fluoro-4-iodophenylamino)-N-(2-hydroxyethoxy)-1,5-dimethyl-6-oxo-1,6-dihydropyridine-3-carboxamide Forms 1 and 2 using a Mettler DSC820e. Samples of typically less than 5 mg of material contained in a 40 µL aluminum pan fitted with a pierced lid was heated over the temperature range 25° C. to 325° C. at a constant heating rate of 10° C. per minute. A purge gas using nitrogen was used at a flow rate of 100 mL per minute.

Figure 14:
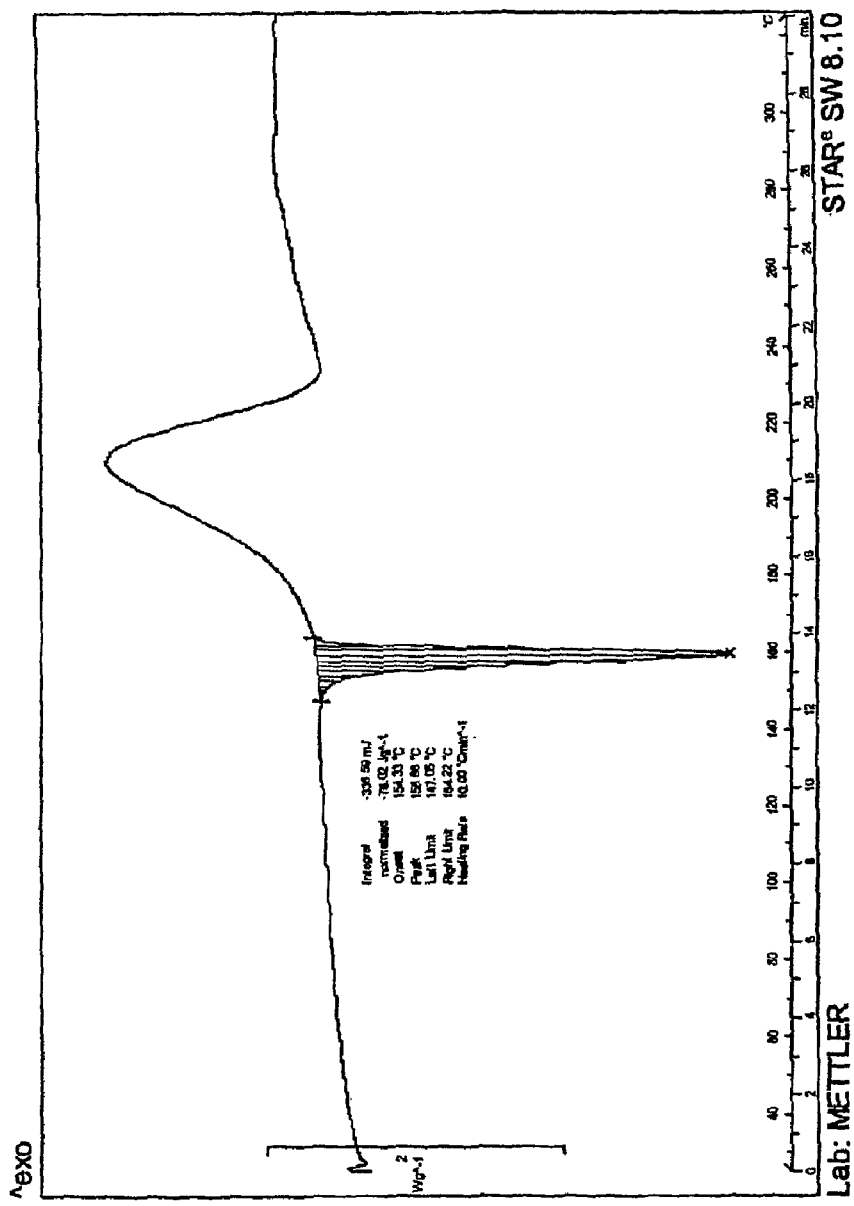
FIG. 14 shows the DSC thermogram for Form 2, 2-(2-fluoro-4-iodophenylamino)-N-(2-hydroxyethoxy)-1,5-dimethyl-6-oxo-1,6-dihydropyridine-3-carboxamide.
Figure 15:
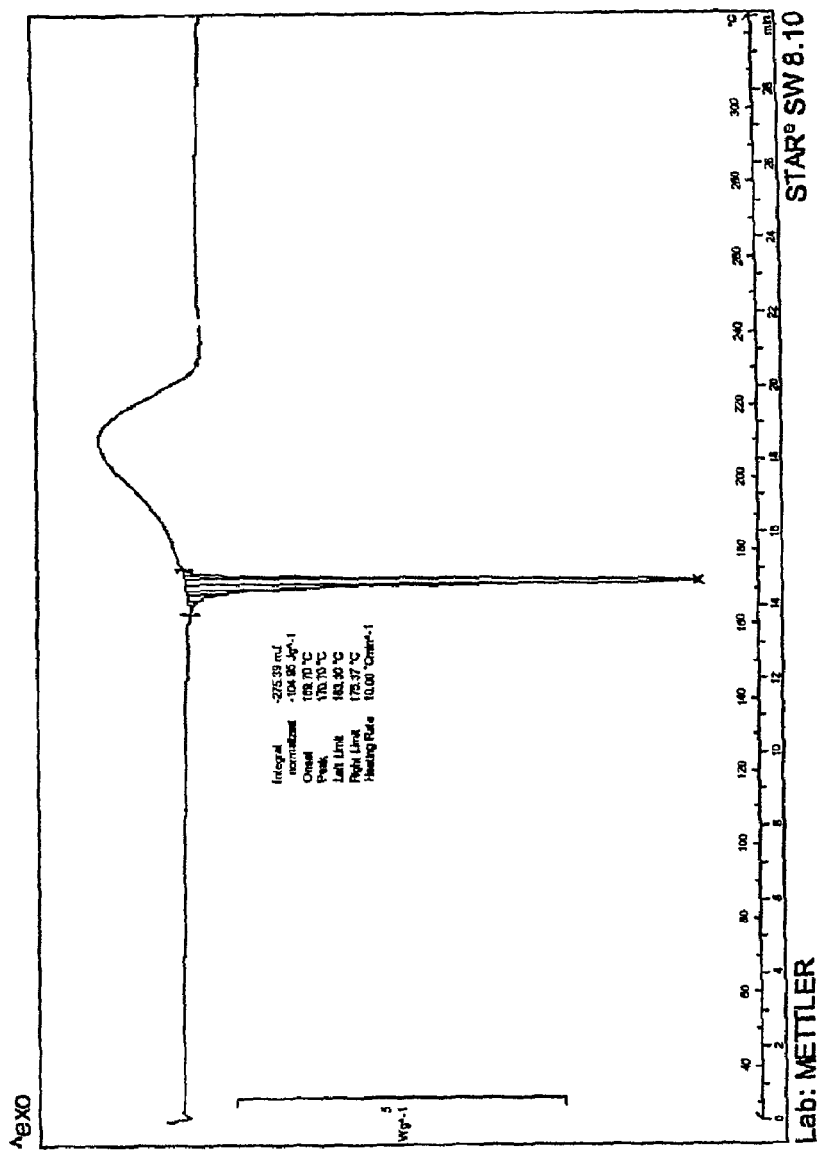
FIG. 15 shows the DSC thermogram for Form 1, 2-(2-fluoro-4-iodophenylamino)-N-(2-hydroxyethoxy)-1,5-dimethyl-6-oxo-1,6-dihydropyridine-3-carboxamide.

The results indicate that Form 1, 2-(2-fluoro-4-iodophenylamino)-N-(2-hydroxyethoxy)-1,5-dimethyl-6-oxo-1,6-dihydropyridine-3-carboxamide shows a large, sharp endotherm with an onset temperature of 169.7° C. due to melting (FIG. 15), whereas Form 2, 2-(2-fluoro-4-iodophenylamino)-N-(2-hydroxyethoxy)-1,5-dimethyl-6-oxo-1,6-dihydropyridine-3-carboxamide has a large sharp endotherm with an onset temperature of 154.3° C. due to melting (FIG. 14). Following the melt a large exothermic event is observed due to degradation. It will be understood that the onset and/or peak temperature values of the DSC may vary slightly from one machine to another, one method to another or from one sample to another, and so the values quoted are not to be construed as absolute.

Example 17

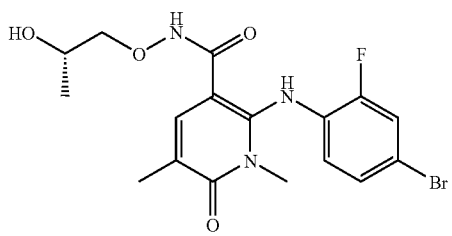

(S)-2-(4-bromo-2-fluorophenylamino)-N-(2-hydroxypropoxy)-1,5-dimethyl-6-oxo-1,6-dihydropyridine-3-carboxamide Step A: Methyl 2-(4-bromo-2-fluorophenylamino)-1,5-dimethyl-6-oxo-1,6-dihydropyridine-3-carboxylate was converted to (S)-2-(4-bromo-2-fluorophenylamino)-N-(2-(tert-butyldimethylsilyloxy)propoxy)-1,5-dimethyl-6-oxo-1,6-dihydropyridine-3-carboxamide following the procedure described in Step A of Example 14.

Step B: To a solution of (S)-2-(4-bromo-2-fluorophenylamino)-N-(2-(tert-butyldimethylsilyloxy)propoxy)-1,5-dimethyl-6-oxo-1,6-dihydropyridine-3-carboxamide (0.037 g, 0.0682 mmol) in THF (1.00 mL) was added 1 M HCl (0.682 mL, 0.682 mmol).

The reaction mixture was stirred for one hour at room temperature. The reaction mixture was diluted with EtOAc and washed with saturated $NaHCO_3$ (3×), saturated NaCl (1×), dried ($Na_2SO_4$), and concentrated under reduced pressure. Purification by flash column chromatography (methylene chloride/methanol, 30:1) gave 0.020 (69%) pure desired product as a yellow solid. MS ESI (+) m/z 428, 430 (M+, Br pattern) detected; $^1$H NMR (400 MHz, $CD_3OD$) δ 7.55 (s, 1H), 7.40 (d, 1H), 7.24 (d, 1H), 6.68 (t, 1H), 3.86 (m, 1H), 3.71 (m, 1H), 3.58 (m, 1H), 3.40 (s, 3H), 2.12 (s, 3H), 1.10 (d, 3H).

Example 18

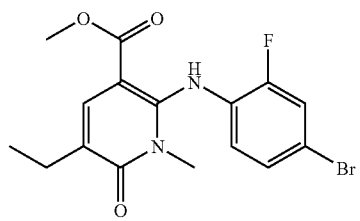

Methyl 2-(4-bromo-2-fluorophenylamino)-5-ethyl-1-methyl-6-oxo-1,6-dihydropyridine-3-carboxylate Step A. Preparation of Methyl 2-chloro-5-ethyl-1-methyl-6-oxo-1,6-dihydropyridine-3-carboxylate: Methyl 5-bromo-2-chloro-1-methyl-6-oxo-1,6-dihydropyridine-3-carboxylate was converted to methyl 2-chloro-5-ethyl-1-methyl-6-oxo-1,6-dihydropyridine-3-carboxylate as described in Step D of Example 13 using diethylzinc (1M in hexanes) to yield the desired product as a yellow crystalline solid.

Step B. Methyl 2-(4-bromo-2-fluorophenylamino)-5-ethyl-1-methyl-6-oxo-1,6-dihydropyridine-3-carboxylate: Methyl 2-chloro-5-ethyl-1-methyl-6-oxo-1,6-dihydropyridine-3-carboxylate was converted to methyl 2-(4-bromo-2-fluorophenylamino)-5-ethyl-1-methyl-6-oxo-1,6-dihydropyridine-3-carboxylate as described in Step E of Example 13. MS ESI (+) m/z 383, 385 (M+, Br pattern) detected; $^1$H NMR (400 MHz, $CDCl_3$) δ 9.59 (s, 1H), 7.76 (s, 1H), 7.32 (d, 1H), 7.18 (d, 1H), 6.59 (t, 1H), 3.86 (s, 3H), 3.28 (s, 3H), 2.56 (q, 2H), 1.22 (t, 3H).

Example 19

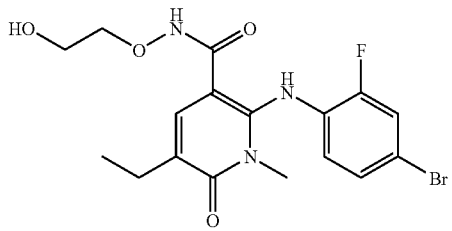

2-(4-Bromo-2-fluorophenylamino)-5-ethyl-N-(2-hydroxyethoxy)-1-methyl-6-oxo-1,6-dihydropyridine-3-carboxamide Methyl 2-(4-bromo-2-fluorophenylamino)-5-ethyl-1-methyl-6-oxo-1,6-dihydropyridine-3-carboxylate was coupled and deprotected as described in Example 14 to yield the desired product as a yellow solid. MS APCI (+) m/z 428, 430 (M+, Br pattern) detected; $^1$H NMR (400 MHz, DMSO-d$_6$) δ 11.51 (br s, 1H), 9.54 (br s, 1H), 7.57 (d, 1H), 7.47 (s, 1H), 7.25 (d, 1H), 6.69 (t, 1H), 4.67 (br s, 1H), 3.74 (m, 2H), 3.50 (m, 2H), 3.24 (s, 3H), 2.43 (q, 2H), 1.14 (t, 3H).

Example 20

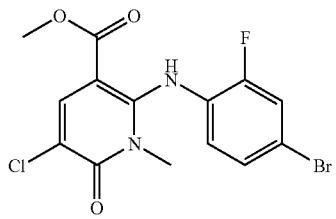

Methyl 2-(4-bromo-2-fluorophenylamino)-5-chloro-1-methyl-6-oxo-1,6-dihydropyridine-3-carboxylate To a solution of methyl 2-(4-bromo-2-fluorophenylamino)-1-methyl-6-oxo-1,6-dihydropyridine-3-carboxylate in DMF was added N-chlorosuccinimide. The reaction mixture was stirred at room temperature for 25 minutes and then quenched with saturated sodium bisulfite. The reaction mixture was diluted with H$_2$O and partitioned between EtOAc/diethyl ether and saturated NaCl. The layers were separated and the aqueous layer was reextracted with EtOAc (1×). The combined organic layers were dried (Na$_2$SO$_4$) and concentrated under reduced pressure. Purification by flash column chromatography (methylene chloride/EtOAc, 15:1) gave the desired product as a white solid. MS ESI (+) m/z 389, 391, 393 (M+, Cl, Br pattern) detected. $^1$H NMR (400 MHz, CDCl$_3$) δ 9.88 (s, 1H), 8.13 (s, 1H), 7.34 (d, 1H), 7.24 (d, 1H), 6.69 (t, 1H), 3.87 (s, 3H), 3.29 (s, 3H).

Example 21

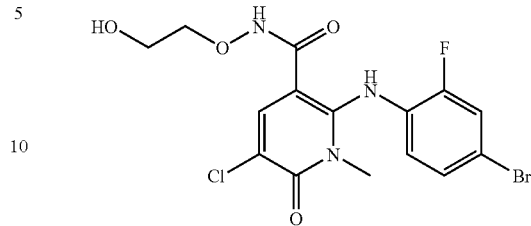

2-(4-bromo-2-fluorophenylamino)-5-chloro-N-(2-hydroxyethoxy)-1-methyl-6-oxo-1,6-dihydropyridine-3-carboxamide Methyl 2-(4-bromo-2-fluorophenylamino)-5-chloro-1-methyl-6-oxo-1,6-dihydropyridine-3-carboxylate was coupled and deprotected as described in Example 14 to yield the desired product as a pale yellow solid. MS APCI (+) m/z 434, 436, 438 (M+, Cl, Br pattern) detected; $^1$H NMR (400 MHz, DMSO-d$_6$) δ 11.56 (br s, 1H), 9.75 (br s, 1H), 7.91 (s, 1H), 7.57 (d, 1H), 7.26 (d, 1H), 6.89 (t, 1H), 4.68 (br s, 1H), 3.70 (m, 2H), 3.50 (m, 2H), 3.28 (s, 3H).

Example 22

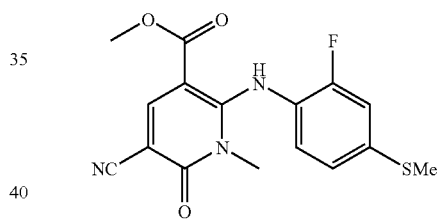

Methyl 5-cyano-2-(2-fluoro-4-(methylthio)phenylamino)-1-methyl-6-oxo-1,6-dihydropyridine-3-carboxylate Step A: Preparation of methyl 2-(2-fluoro-4-(methylthio)phenylamino)-1-methyl-6-oxo-1,6-dihydropyridine-3-carboxylate: To a solution of prepared from methyl 2-chloro-1-methyl-6-oxo-1,6-dihydropyridine-3-carboxylate and 2-fluoro-4-(methylthio)benzenamine in THF (5 mL) at −78° C. under N$_2$ was added lithium bis(trimethylsilyl)amide (1 M solution in hexanes) dropwise. The reaction mixture was stirred for one hour at −78° C. Methyl 2-(2-fluoro-4-(methylthio)phenylamino)-1-methyl-6-oxo-1,6-dihydropyridine-3-carboxylate was then added dropwise as a solution in THF and the reaction mixture was stirred for one hour at −78° C. The reaction mixture was quenched by the addition of H$_2$O and the pH was adjusted to pH 7 with saturated NH$_4$Cl and then diluted with EtOAc. The organic layer was separated and washed with saturated NaCl, dried (Na$_2$SO$_4$), and concentrated under reduced pressure. Purification by flash column chromatography (methylene chloride/EtOAc, 15:1) gave the desired product.

Step B: Preparation of methyl 5-bromo-2-(2-fluoro-4-(methylthio)phenylamino)-1-methyl-6-oxo-1,6-dihydropyridine-3-carboxylate: To a solution of methyl 2-(2-fluoro-4-(methylthio)phenylamino)-1-methyl-6-oxo-1,6-dihydropyridine-3-carboxylate was added N-bromosuccinimide. The reaction mixture was stirred at room temperature for 25 minutes and then quenched with saturated sodium bisulfite. The reaction mixture was diluted with $H_2O$ and partitioned between EtOAc/diethyl ether and saturated NaCl. The layers were separated and the aqueous layer was reextracted with EtOAc (1×). The combined organic layers were dried ($Na_2SO_4$) and concentrated under reduced pressure. Purification by flash column chromatography (methylene chloride/EtOAc, 15:1) gave methyl 5-bromo-2-(2-fluoro-4-(methylthio)phenylamino)-1-methyl-6-oxo-1,6-dihydropyridine-3-carboxylate.

Step C: Methyl 5-cyano-2-(2-fluoro-4-(methylthio)phenylamino)-1-methyl-6-oxo-1,6-dihydropyridine-3-carboxylate: A mixture of methyl 5-bromo-2-(2-fluoro-4-(methylthio)phenylamino)-1-methyl-6-oxo-1,6-dihydropyridine-3-carboxylate (0.020 g, 0.050 mmol), tris(dibenzylideneacetone)-dipalladium(0) (0.046 g, 0.050 mmol), 1,1'-bis(diphenylphosphine)-ferrocene (0.055 g, 0.100 mmol) and $Zn(CN)_2$ (0.006 g, 0.055 mmol) was heated at 120° C. for 2 hours. The reaction mixture was diluted with EtOAc and $H_2O$ and the layers separated. The EtOAc layer was washed with saturated $NH_4Cl$ and saturated NaCl, dried ($Na_2SO_4$) and concentrated under reduced pressure to a dark yellow gum. Purification by flash column chromatography (methylene chloride/EtOAc, 10:1) gave 0.005 g (29%) pure desired product as a yellow solid. MS APCI (−) m/z 346 (M−1) detected; $^1$H NMR (400 MHz, $CDCl_3$) δ 10.84 (s, 1H), 8.39 (s, 1H), 6.95-7.06 (m, 3H), 3.90 (s, 3H), 3.17 (s, 3H), 2.50 (s, 3H).

The following compounds were prepared by the procedures as previously described in the above Examples unless otherwise indicated.

Example 23-A

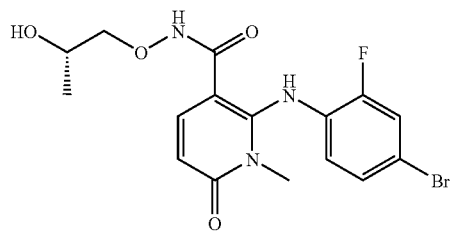

(S)-2-(4-bromo-2-fluorophenylamino)-N-(2-hydroxypropoxy)-1-methyl-6-oxo-1,6-dihydropyridine-3-carboxamide Step A: Preparation of 2-Chloro-6-oxo-1,6-dihydropyridine-3-carboxylic acid: 2-Chloro-6-oxo-1,6-dihydropyridine-3-carboxylic acid was prepared from dichloro-nicotinic acid (3.00 g, 15.6 mmol, Aldrich) according to the procedure described in U.S. Pat. No. 3,682,932 (1972) to yield 1.31 g (48%) of the desired product.

Step B: Preparation of methyl 2-chloro-1-methyl-6-oxo-1,6-dihydropyridine-3-carboxylate: To a solution of 2-chloro-6-oxo-1,6-dihydropyridine-3-carboxylic acid (0.644 g, 3.71 mmol) in DMF (20 mL) was added lithium hydride (95%, 0.078 g, 9.28 mmol) and the reaction mixture was stirred for 40 minutes under $N_2$. Methyl iodide (0.508 mL, 1.16 g, 8.16 mmol) was then added and the reaction mixture was stirred for an additional 45 minutes. The reaction mixture was quenched with 2 M HCl until the pH was 6-7. The reaction mixture was diluted with EtOAc and saturated NaCl and the layers were separated. The aqueous layer was back-extracted with EtOAc (1×). The combined organic layers were dried ($Na_2SO_4$) and concentrated under reduced pressure to yield a crude yellow solid. HPLC analysis showed two products in a 4:1 ratio that were separated by flash column chromatography (methylene chloride/EtOAc, 15:1 to 10:1) to give 0.466 g (62%) pure desired product as a white crystalline solid. The minor product was also isolated as a pale yellow crystalline solid and identified as the regioisomer methyl 2-chloro-6-methoxynicotinate.

Step C: Preparation of Methyl 2-(4-bromo-2-fluorophenylamino)-1-methyl-6-oxo-1,6-dihydropyridine-3-carboxylate: To a solution of 4-bromo-2-fluoroaniline (0.192 g, 1.01 mmol) in THF (5 mL) at −78° C. under $N_2$ was added lithium bis(trimethylsilyl)amide (1.50 mL, 1.50 mmol, 1 M solution in hexanes) dropwise. The reaction mixture was stirred for one hour at −78° C. Methyl 2-chloro-1-methyl-6-oxo-1,6-dihydropyridine-3-carboxylate (0.202 g, 1.00 mmol) was then added dropwise as a solution in THF (5 mL) and the reaction mixture was stirred for one hour at −78° C. The reaction mixture was quenched by the addition of $H_2O$ and the pH was adjusted to pH 7 with saturated $NH_4Cl$ and then diluted with EtOAc. The organic layer was separated and washed with saturated NaCl, dried ($Na_2SO_4$), and concentrated under reduced pressure. Purification by flash column chromatography (methylene chloride/EtOAc, 15:1) gave 0.232 g (65%) pure desired product as a white crystalline solid.

Step D: Preparation of (S)-2-(4-Bromo-2-fluorophenylamino)-N-(2-(tert-butyldimethylsilyloxy)propoxy)-1-methyl-6-oxo-1,6-dihydropyridine-3-carboxamide: To a solution of methyl 2-(4-bromo-2-fluorophenylamino)-1-methyl-6-oxo-1,6-dihydropyridine-3-carboxylate (0.050 g, 0.14 mmol) and (S)—O-(2-(tert-butyldimethylsilyloxy)propyl)hydroxylamine (0.072 g, 0.35 mmol) in THF (1.50 mL) at 0° C. was slowly added lithium bis(trimethylsilyl)amide (0.70 ml, 0.70 mmol). After addition, the reaction mixture was stirred for 1 hour at room temperature and then quenched by with saturated $NaHCO_3$. The reaction mixture was partitioned between EtOAc and sat NaCl. The layers were separated and the aqueous layer was back-extracted with EtOAc (1×). The combined organic layers were dried ($Na_2SO_4$), filtered and concentrated under reduced pressure to yield a crude brown solid that was used without further purification in the next step.

Step E: Preparation of (S)-2-(4-bromo-2-fluorophenylamino)-N-(2-hydroxypropoxy)-1-methyl-6-oxo-1,6-dihydropyridine-3-carboxamide: To a solution of (S)-2-(4-bromo-2-fluorophenylamino)-N-(2-(tert-butyldimethylsilyloxy)propoxy)-1-methyl-6-oxo-1,6-dihydropyridine-3-carboxamide (0.074 g, 0.14 mmol) in THF (1.50 mL) was added 1 M aqueous HCl (1.4 ml, 1.4 mmol). The reaction was stirred for 16 hours at room temperature. The reaction mixture was diluted with EtOAc and washed with saturated aqueous $NaHCO_3$ (3×) and saturated aqueous NaCl. The organic layer was dried ($Na_2SO_4$), filtered and concentrated under reduced pressure to yield a crude white solid. Purification of the crude product by trituration with $Et_2O$ and isolation of the resulting solid provided (S)-2-(4-bromo-2-fluorophenylamino)-N-(2-hydroxypropoxy)-1-methyl-6-oxo-1,6-dihydropyridine-3-carboxamide (0.030 g;

52% over two steps) as a white solid. MS ESI (+) m/z 414, 416 (M+) Br pattern detected; ¹H NMR (400 MHz, CD₃OD) δ 7.65 (d, 1H), 7.42 (dd, 1H), 7.28 (m, 1H), 6.81 (t, 1H), 6.28 (d, 1H), 3.88 (m, 1H), 3.70 (dd, 1H), 3.58 (dd, 1H), 3.38 (s, 3H), 1.11 (d, 3H).

Example 23-B

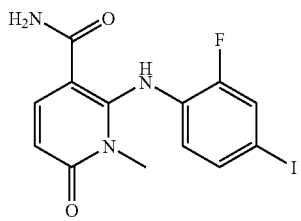

2-(2-fluoro-4-iodophenylamino)-1-methyl-6-oxo-1,6-dihydropyridine-3-carboxamide

MS ESI (+) m/z 388 (M+1) pattern detected; ¹H NMR (400 MHz, CDCl₃) δ 10.8 (s, 1H), 7.47 (d, 2H), 7.39 (d, 1H), 6.54 (t, 1H), 6.26 (d, 1H), 5.59 (br s, 2H), 3.24 (s, 3H).

Example 23-C

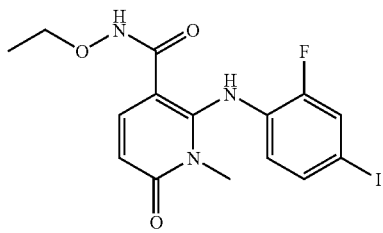

N-ethoxy-2-(2-fluoro-4-iodophenylamino)-1-methyl-6-oxo-1,6-dihydropyridine-3-carboxamide MS ESI (+) m/z 432 (M+1) pattern detected; ¹H NMR (400 MHz, DMSO-d₆) δ 11.4 (br s, 1H), 9.83 (br s, 1H), 7.66 (dd, 1H), 7.58 (d, 1H), 7.43 (d, 1H), 6.65 (t, 1H), 6.18 (d, 1H), 3.70 (q, 2H), 3.21 (s, 3H), 1.10 (t, 3H).

Example 23-D

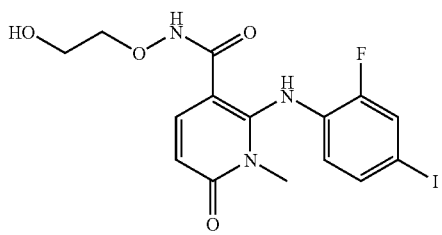

2-(2-fluoro-4-iodophenylamino)-N-(2-hydroxyethoxy)-1-methyl-6-oxo-1,6-dihydropyridine-3-carboxamide MS ESI (+) m/z 448 (M+1) pattern detected; ¹H NMR (400 MHz, CD₃OD) δ 7.66 (d, 1H), 7.56 (m, 1H), 7.46 (m, 1H), 6.65 (t, 1H), 6.28 (d, 1H), 3.85 (t, 2H), 3.67 (t, 2H), 3.36 (s, 3H).

Example 23-E

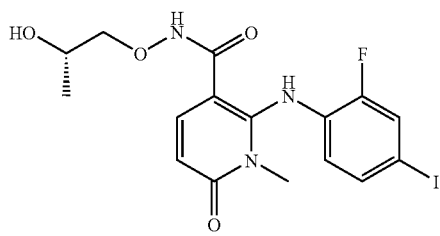

(S)-2-(2-fluoro-4-iodophenylamino)-N-(2-hydroxypropoxy)-1-methyl-6-oxo-1,6-dihydropyridine-3-carboxamide MS ESI (+) m/z 462 (M+1) pattern detected; ¹H NMR (400 MHz, CD₃OD) δ 7.66 (d, 1H), 7.56 (d, 1H), 7.46 (d, 1H), 6.65 (t, 1H), 6.28 (d, 1H), 3.85 (m, 1H), 3.67 (m, 1H), 3.57 (m, 1H), 3.38 (s, 3H), 1.11 (d, 3H).

Example 23-F

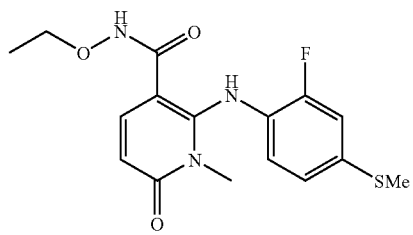

N-ethoxy-2-(2-fluoro-4-(methylthio)phenylamino)-1-methyl-6-oxo-1,6-dihydropyridine-3-carboxamide MS APCI (+) m/z 352 (M+1) pattern detected; ¹H NMR (400 MHz, CD₃OD) δ 7.64 (d, 1H), 7.12 (dd, 1H), 7.05 (m, 1H), 6.86 (t, 1H), 6.21 (d, 1H), 3.85 (q, 2H), 3.32 (s, 3H), 2.47 (s, 3H), 1.22 (t, 3H).

Example 23-G

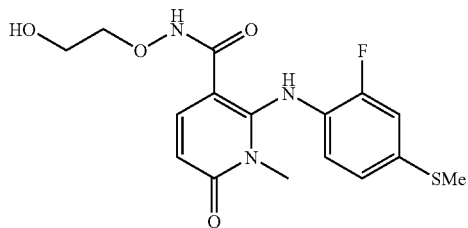

2-(2-fluoro-4-(methylthio)phenylamino)-N-(2-hydroxyethoxy)-1-methyl-6-oxo-1,6-dihydropyridine-3-carboxamide MS ESI (+) m/z 368 (M+1) pattern detected; ¹H NMR (400 MHz, CDCl₃) δ 10.28 (s, 1H), 8.48 (s, 1H), 7.38 (d, 1H), 7.00 (m, 1H), 6.96 (m, 1H), 6.79 (t, 1H), 6.19 (d, 1H), 4.04 (m, 2H), 3.88 (m, 1H), 3.75 (m, 2H), 3.22 (s, 3H), 2.48 (s, 3H).

Example 23-H

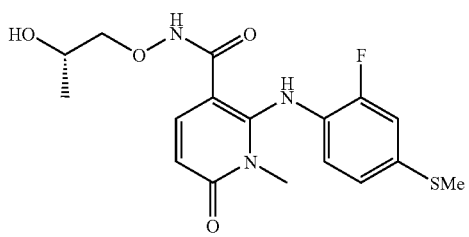

(S)-2-(2-fluoro-4-(methylthio)phenylamino)-N-(2-hydroxypropoxy)-1-methyl-6-oxo-1,6-dihydropyridine-3-carboxamide MS ESI (+) m/z 382 (M+1) pattern detected; ¹H NMR (400 MHz, CD₃OD) δ 7.64 (d, 1H), 7.12 (d 1H), 7.04 (d, 1H), 6.85 (t, 1H), 6.21 (d, 1H), 4.01 (m, 1H), 3.90 (m, 1H), 3.71 (m, 1H), 3.60 (m, 1H), 3.32 (s, 3H), 2.47 (s, 3H), 1.10 (d, 3H).

Example 23-H1

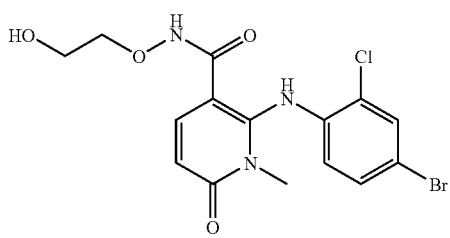

2-(4-bromo-2-chlorophenylamino)-N-(2-hydroxyethoxy)-1-methyl-6-oxo-1,6-dihydropyridine-3-carboxamide Example 23-H2

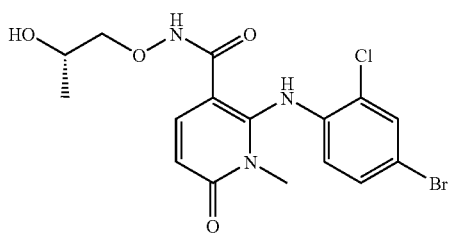

(S)-2-(4-bromo-2-chlorophenylamino)-N-(2-hydroxypropoxy)-1-methyl-6-oxo-1,6-dihydropyridine-3-carboxamide Example 23-K

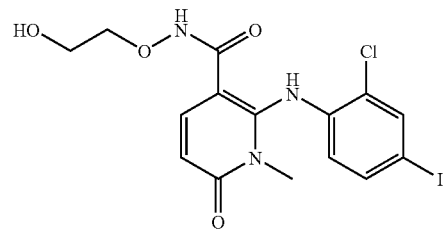

2-(2-chloro-4-iodophenylamino)-N-(2-hydroxyethoxy)-1-methyl-6-oxo-1,6-dihydropyridine-3-carboxamide MS APCI (+) m/z 464, 466 (M+, Cl pattern) detected; ¹H NMR (400 MHz, DMSO-d₆) δ 11.59 (br s, 1H), 10.06 (br s, 1H), 7.86 (d, 1H), 7.64 (d, 1H), 7.54 (dd, 1H), 6.53 (d, 1H), 6.21 (d, 1H), 4.67 (t, 1H), 3.78 (t, 2H), 3.52 (m, 2H), 3.13 (s, 3H).

Example 23-L

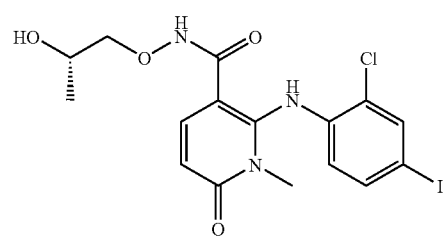

(S)-2-(2-chloro-4-iodophenylamino)-N-(2-hydroxypropoxy)-1-methyl-6-oxo-1,6-dihydropyridine-3-carboxamide MS APCI (+) m/z 478, 480 (M+, Cl pattern) detected; ¹H NMR (400 MHz, DMSO-d₆) δ 11.59 (s, 1H), 9.99 (s, 1H), 7.86 (d, 1H), 7.64 (d, 1H), 7.54 (dd, 1H), 6.53 (d, 1H), 6.21 (d, 1H), 4.73 (m, 1H), 3.75 (m, 1H), 3.58 (m, 2H), 3.14 (s, 3H), 1.02 (d, 3H).

Example 23-M

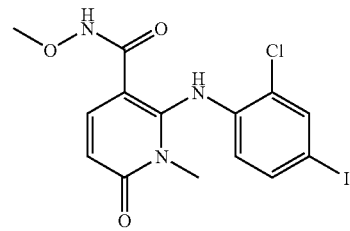

2-(2-chloro-4-iodophenylamino)-N-methoxy-1-methyl-6-oxo-1,6-dihydropyridine-3-carboxamide

Example 23-N

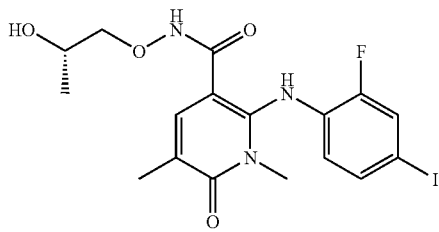

(S)-2-(2-fluoro-4-iodophenylamino)-N-(2-hydroxypropoxy)-1,5-dimethyl-6-oxo-1,6-dihydropyridine-3-carboxamide MS ESI (+) m/z 476 (M+1) pattern detected; $^1$H NMR (400 MHz, CDCl$_3$) δ 9.79 (s, 1H), 8.53 (s, 1H), 7.46 (d, 1H), 7.35 (m, 1H), 6.44 (t, 1H), 4.15 (m, 1H), 3.92 (dd, 1H), 3.69 (dd, 1H), 3.28 (s, 3H), 2.14 (s, 3H), 1.14 (d, 3H).

Example 23-O

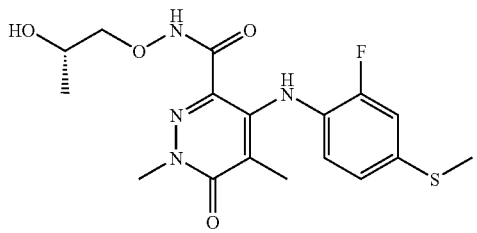

(S)-4-(2-fluoro-4-(methylthio)phenylamino)-N-(2-hydroxypropoxy)-1,5-dimethyl-6-oxo-1,6-dihydropyridazine-3-carboxamide MS APCI (−) m/z 395 (M−1) detected; $^1$H NMR (400 MHz, CD$_3$OD) δ 7.10 (dd, 1H), 7.03 (d, 1H), 6.87 (t, 1H), 4.00 (m, 1H), 3.85 (dd, 1H), 3.79 (s, 3H), 3.72 (dd, 1H), 2.47 (s, 3H), 1.75 (s, 3H), 1.16 (d, 3H).

Example 23-P

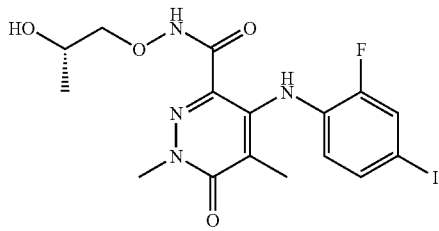

(S)-4-(2-fluoro-4-iodophenylamino)-N-(2-hydroxypropoxy)-1,5-dimethyl-6-oxo-1,6-dihydropyridazine-3-carboxamide MS APCI (−) m/z 475 (M−1) detected; $^1$H NMR (400 MHz, CD$_3$OD) δ 7.52 (dd, 1H), 7.44 (dd, 1H), 6.63 (t, 1H), 3.98 (m, 1H), 3.84 (dd, 1H), 3.79 (s, 3H), 3.72 (dd, 1H), 1.78 (s, 3H), 1.16 (d, 3H).

Example 23-Q

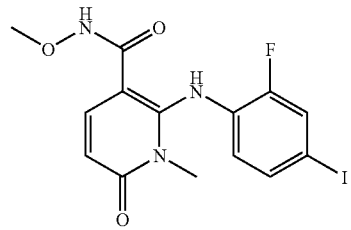

2-(2-fluoro-4-iodophenylamino)-N-methoxy-1-methyl-6-oxo-1,6-dihydropyridine-3-carboxamide The following compounds were prepared by the procedures as previously described in the above Examples.

Example 24-A

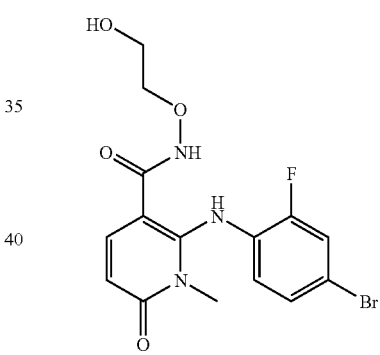

2-(4-bromo-2-fluorophenylamino)-N-(2-hydroxyethoxy)-1-methyl-6-oxo-1,6-dihydropyridine-3-carboxamide

Example 24-B

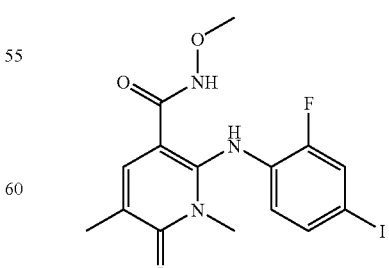

2-(2-fluoro-4-iodophenylamino)-N-methoxy-1,5-dimethyl-6-oxo-1,6-dihydropyridine-3-carboxamide

Example 24-C

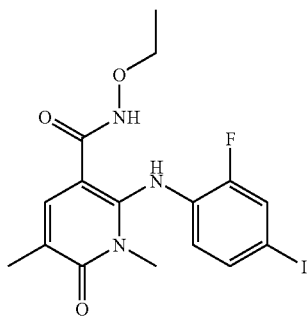

N-ethoxy-2-(2-fluoro-4-iodophenylamino)-1,5-dimethyl-6-oxo-1,6-dihydropyridine-3-carboxamide

Example 24-D

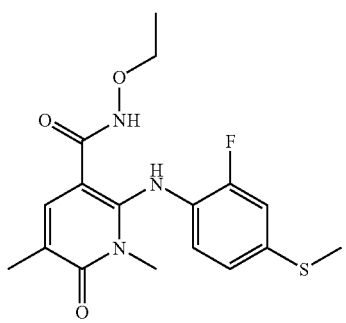

N-ethoxy-2-(2-fluoro-4-(methylthio)phenylamino)-1,5-dimethyl-6-oxo-1,6-dihydropyridine-3-carboxamide MS APCI (+) m/z 366 (M+1) pattern detected; $^{1}$H NMR (400 MHz, DMSO-d$_{6}$) δ 11.38 (br s, 1H), 9.79 (br s, 1H), 7.54 (s, 1H), 7.23 (dd, 1H), 6.99 (dd, 1H), 6.73 (t, 1H), 3.76 (q, 2H), 3.19 (s, 3H), 2.46 (s, 3H), 2.01 (s, 3H), 1.12 (t, 3H).

Example 24-E

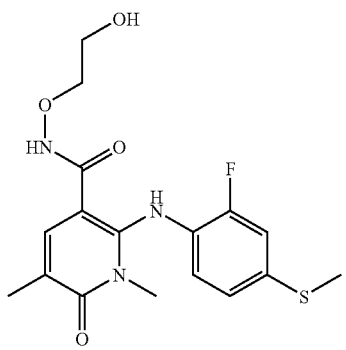

2-(2-fluoro-4-(methylthio)phenylamino)-N-(2-hydroxyethoxy)-1,5-dimethyl-6-oxo-1,6-dihydropyridine-3-carboxamide MS APCI (+) m/z 382 (M+1) pattern detected; $^{1}$H NMR (400 MHz, DMSO-d$_{6}$) δ 11.48 (br s, 1H), 9.78 (br s, 1H), 7.56 (s, 1H), 7.23 (dd, 1H), 6.99 (m, 1H), 6.73 (t, 1H), 4.68 (br s, 1H), 3.76 (t, 2H), 3.51 (t, 2H), 3.19 (s, 3H), 2.46 (s, 3H), 2.01 (s, 3H).

Example 24-F

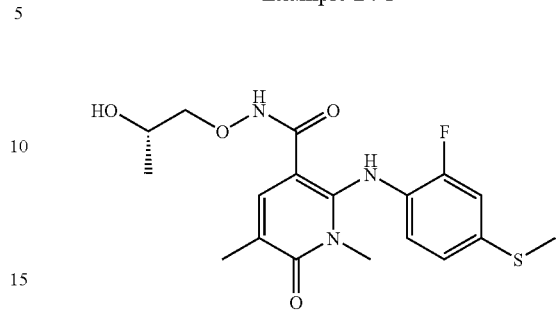

(S)-2-(2-fluoro-4-(methylthio)phenylamino)-N-(2-hydroxypropoxy)-1,5-dimethyl-6-oxo-1,6-dihydropyridine-3-carboxamide MS APCI (+) m/z 396 (M+1) pattern detected; $^{1}$H NMR (400 MHz, DMSO-d$_{6}$) δ 11.48 (br s, 1H), 9.68 (br s, 1H), 7.55 (s, 1H), 7.23 (dd, 1H), 6.99 (dd, 1H), 6.73 (t, 1H), 4.73 (d, 1H), 3.74 (m, 1H), 3.56 (d, 2H), 3.20 (s, 3H), 2.46 (s, 3H), 2.01 (s, 3H), 1.02 (d, 3H).

Example 24-G

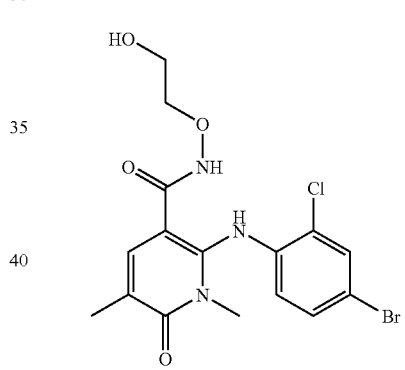

2-(4-bromo-2-chlorophenylamino)-N-(2-hydroxyethoxy)-1,5-dimethyl-6-oxo-1,6-dihydropyridine-3-carboxamide

Example 24-H

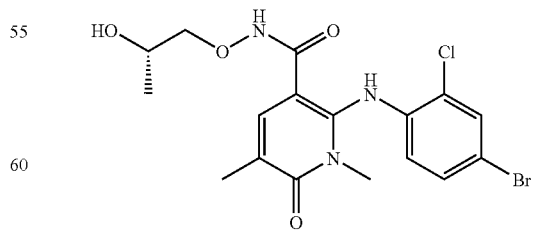

(S)-2-(4-bromo-2-chlorophenylamino)-N-(2-hydroxypropoxy)-1,5-dimethyl-6-oxo-1,6-dihydropyridine-3-carboxamide Example 24-I

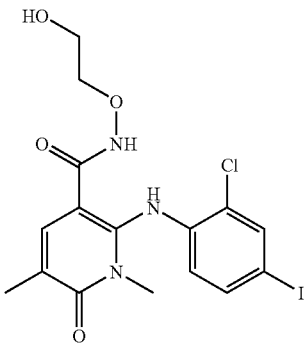

2-(2-chloro-4-iodophenylamino)-N-(2-hydroxy-
ethoxy)-1,5-dimethyl-6-oxo-1,6-dihydropyridine-3-
carboxamide MS APCI (+) m/z 478, 480 (M+, Cl pattern) detected; $^1$H NMR (400 MHz, CD$_3$OD) δ 7.79 (d, 1H), 7.59 (s, 1H), 7.52 (dd, 1H), 6.39 (d, 1H), 3.89 (t, 2H), 3.67 (t, 2H), 3.34 (s, 3H), 2.13 (s, 3H).

Example 24-J

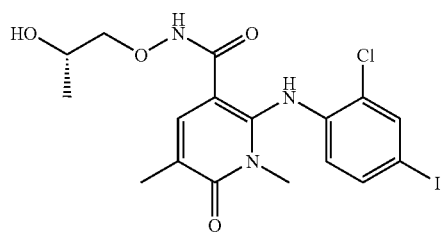

(S)-2-(2-chloro-4-iodophenylamino)-N-(2-hydrox-
ypropoxy)-1,5-dimethyl-6-oxo-1,6-dihydropyridine-
3-carboxamide Example 24-K

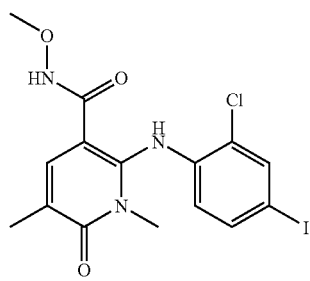

2-(2-chloro-4-iodophenylamino)-N-methoxy-1,5-
dimethyl-6-oxo-1,6-dihydropyridine-3-carboxamide Example 24-L

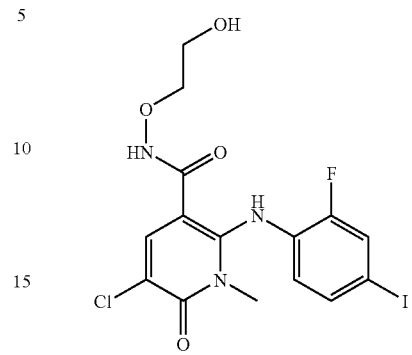

5-chloro-2-(2-fluoro-4-iodophenylamino)-N-(2-hy-
droxyethoxy)-1-methyl-6-oxo-1,6-dihydropyridine-
3-carboxamide MS ESI (+) m/z 482, 484 (M+, Cl pattern) detected; $^1$H NMR (400 MHz, DMSO-d$_6$) δ 11.56 (br s, 1H), 9.69 (br s, 1H), 7.89 (s, 1H), 7.64 (dd, 1H), 7.40 (dd, 1H), 6.72 (t, 1H), 4.66 (t, 1H), 3.67 (t, 2H), 3.49 (m, 2H), 3.28 (s, 3H).

Example 24-M

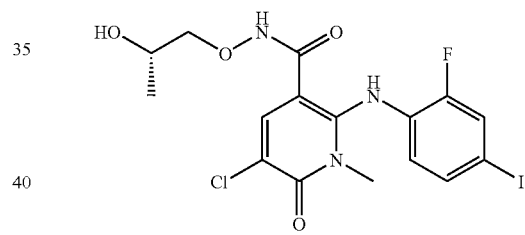

(S)-5-chloro-2-(2-fluoro-4-iodophenylamino)-N-(2-
hydroxypropoxy)-1-methyl-6-oxo-1,6-dihydropyri-
dine-3-carboxamide Example 24-N

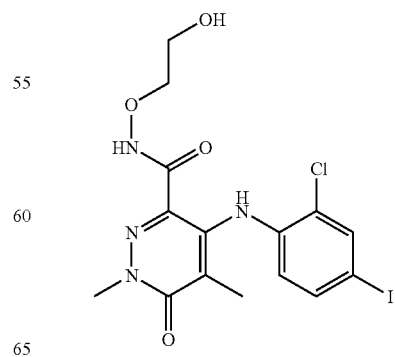

4-(2-chloro-4-iodophenylamino)-N-(2-hydroxyethoxy)-1,5-dimethyl-6-oxo-1,6-dihydropyridazine-3-carboxamide MS APCI (−) m/z 477, 479 (M−1, Cl pattern) detected; $^1$H NMR (400 MHz, CD$_3$OD) δ 7.77 (d, 1H), 7.54 (dd, 1H), 6.51 (d, 1H), 4.01 (t, 2H), 3.81 (s, 3H), 3.75 (t, 2H), 1.74 (s, 3H).

Example 24-O

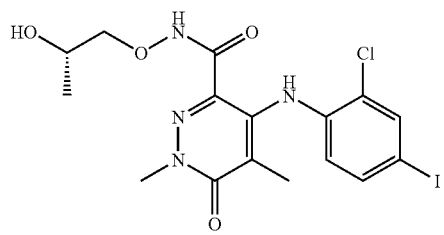

(S)-4-(2-chloro-4-iodophenylamino)-N-(2-hydroxypropoxy)-1,5-dimethyl-6-oxo-1,6-dihydropyridazine-3-carboxamide MS APCI (−) m/z 491, 493 (M−1, Cl pattern) detected; $^1$H NMR (400 MHz, CD$_3$OD) δ 7.77 (d, 1H), 7.54 (dd, 1H), 6.51 (d, 1H), 4.00 (m, 1H), 3.87 (dd, 1H), 3.80 (s, 3H), 3.75 (dd, 1H), 1.74 (s, 3H), 1.16 (d, 3H).

Example 24-P

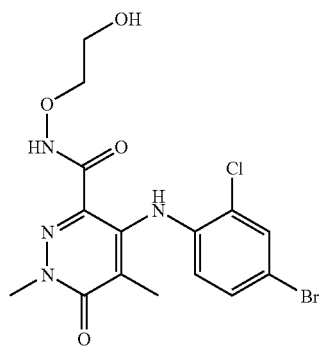

4-(4-bromo-2-chlorophenylamino)-N-(2-hydroxyethoxy)-1,5-dimethyl-6-oxo-1,6-dihydropyridazine-3-carboxamide MS APCI (−) m/z 429, 431, 433 (M−1, Br, Cl pattern) detected; $^1$H NMR (400 MHz, CD$_3$OD) δ 7.62 (d, 1H), 7.38 (dd, 1H), 6.67 (d, 1H), 4.02 (t, 2H), 3.81 (s, 3H), 3.75 (t, 2H), 1.73 (s, 3H).

Example 24-Q

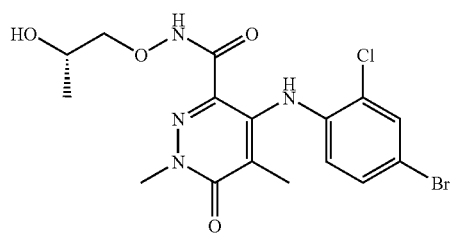

(S)-4-(4-bromo-2-chlorophenylamino)-N-(2-hydroxypropoxy)-1,5-dimethyl-6-oxo-1,6-dihydropyridazine-3-carboxamide Additional compounds of the present invention include compounds of general Formulas Ia, IVa, IVb, IVc, IVd, IVe, IVf, and IVg as shown in the following Tables 1-8

TABLE 1

Ia

| R$^7$ | R$^9$ | R$^1$ | R$^8$ | R$^3$ |
|---|---|---|---|---|
| Me | Me | F | Br | H |
| | | | | OH |
| | | | | OMe |
| | | | | OEt |
| | | | | HOCH$_2$CH$_2$O |
| | | | | HOCH$_2$C(Me)$_2$O |
| | | | | (S)-MeCH(OH)CH$_2$O |
| | | | | (R)-HOCH$_2$CH(OH)CH$_2$O |
| | | | | c-PrCH$_2$O |
| Me | Me | F | I | H |
| | | | | OH |
| | | | | OMe |
| | | | | OEt |
| | | | | HOCH$_2$CH$_2$O |
| | | | | HOCH$_2$C(Me)$_2$O |
| | | | | (S)-MeCH(OH)CH$_2$O |
| | | | | (R)-HOCH$_2$CH(OH)CH$_2$O |
| | | | | c-PrCH$_2$O |
| Me | Me | F | SMe | H |
| | | | | OH |
| | | | | OMe |
| | | | | OEt |
| | | | | HOCH$_2$CH$_2$O |
| | | | | HOCH$_2$C(Me)$_2$O |
| | | | | (S)-MeCH(OH)CH$_2$O |
| | | | | (R)-HOCH$_2$CH(OH)CH$_2$O |
| | | | | c-PrCH$_2$O |
| Me | Me | Cl | Br | H |
| | | | | OH |
| | | | | OMe |
| | | | | OEt |
| | | | | HOCH$_2$CH$_2$O |
| | | | | HOCH$_2$C(Me)$_2$O |
| | | | | (S)-MeCH(OH)CH$_2$O |
| | | | | (R)-HOCH$_2$CH(OH)CH$_2$O |
| | | | | c-PrCH$_2$O |
| Me | Me | Cl | I | H |
| | | | | OH |
| | | | | OMe |
| | | | | OEt |
| | | | | HOCH$_2$CH$_2$O |
| | | | | HOCH$_2$C(Me)$_2$O |
| | | | | (S)-MeCH(OH)CH$_2$O |
| | | | | (R)-HOCH$_2$CH(OH)CH$_2$O |
| | | | | c-PrCH$_2$O |
| Me | Me | Cl | SMe | H |
| | | | | OH |
| | | | | OMe |
| | | | | OEt |
| | | | | HOCH$_2$CH$_2$O |
| | | | | HOCH$_2$C(Me)$_2$O |
| | | | | (S)-MeCH(OH)CH$_2$O |
| | | | | (R)-HOCH$_2$CH(OH)CH$_2$O |
| | | | | c-PrCH$_2$O |

TABLE 1-continued

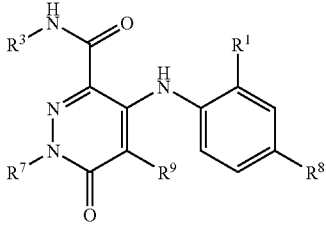
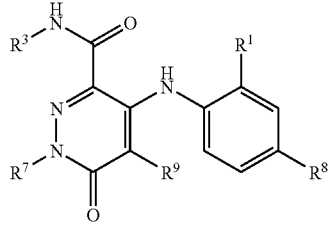

| R⁷ | R⁹ | R¹ | R⁸ | R³ |
|---|---|---|---|---|
| Me | F | F | Br | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | F | F | I | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | F | F | SMe | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | F | Cl | Br | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | F | Cl | I | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | F | Cl | SMe | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | Cl | F | Br | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | Cl | F | I | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | Cl | F | SMe | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | Cl | Cl | Br | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | Cl | Cl | I | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| Me | Cl | Cl | SMe | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| c-PrCH₂ | Me | F | Br | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |
| c-PrCH₂ | Me | F | I | H |
|  |  |  |  | OH |
|  |  |  |  | OMe |
|  |  |  |  | OEt |
|  |  |  |  | HOCH₂CH₂O |
|  |  |  |  | HOCH₂C(Me)₂O |
|  |  |  |  | (S)-MeCH(OH)CH₂O |
|  |  |  |  | (R)-HOCH₂CH(OH)CH₂O |
|  |  |  |  | c-PrCH₂O |

TABLE 1-continued

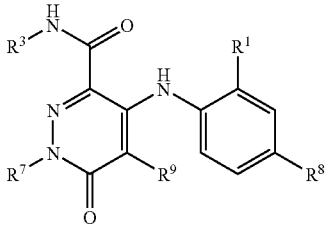

| R⁷ | R⁹ | R¹ | R⁸ | R³ |
|---|---|---|---|---|
| c-PrCH₂ | Me | F | SMe | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |
| c-PrCH₂ | F | F | Br | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |
| c-PrCH₂ | F | F | I | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |
| c-PrCH₂ | F | F | SMe | H |
| | | | | OH |
| | | | | OMe |
| | | | | OEt |
| | | | | HOCH₂CH₂O |
| | | | | HOCH₂C(Me)₂O |
| | | | | (S)-MeCH(OH)CH₂O |
| | | | | (R)-HOCH₂CH(OH)CH₂O |
| | | | | c-PrCH₂O |

TABLE 2

Structure IVa (as shown).

TABLE 2-continued

Structure IVa (as shown).

| R⁹ | R³ |
|---|---|
| Me | HOCH₂CH(·)CH₂– (and additional R³ groups shown as structural fragments) |
| Et | (various R³ structural fragments shown) |

TABLE 2-continued

IVa

| R⁹ | R³ |
|---|---|
| | HO-CH(OH)-CH₂- |
| | MeO-CH₂CH₂-CH₂- |
| | cyclopropyl-CH₂- |
| | Et-CH(CH₃)- |
| | CH₃- |
| Cl | HO-CH₂CH₂-CH₂- |
| | (S)-HO-CH(CH₃)-CH₂- |
| | (S)-HO-CH(Et)-CH₂- |
| | HO-CH₂-C(CH₃)₂-CH₂- |
| | HO-CH₂-CH(OH)-CH₂- |
| | MeO-CH₂CH₂-CH₂- |
| | cyclopropyl-CH₂- |

TABLE 2-continued

IVa

| R⁹ | R³ |
|---|---|
| | Et-CH(CH₃)- |
| | CH₃- |

TABLE 3

IVb

| R⁹ | R³ |
|---|---|
| Me | H |
| | HO-CH₂CH₂-CH₂- |
| | (S)-HO-CH(CH₃)-CH₂- |
| | (S)-HO-CH(Et)-CH₂- |
| | HO-CH₂-C(CH₃)₂-CH₂- |
| | (S)-HO-CH₂-CH(OH)-CH₂- |
| | MeO-CH₂CH₂-CH₂- |

TABLE 3-continued
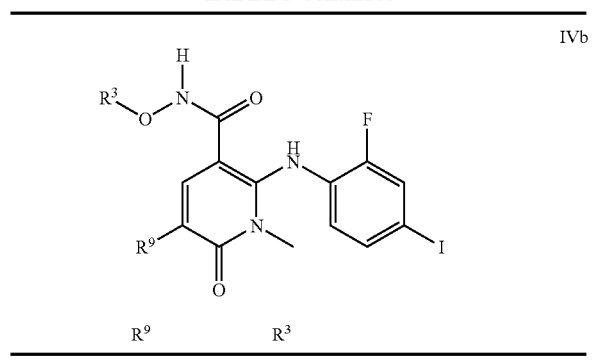
IVb
| R⁹ | R³ |
|---|---|
| | 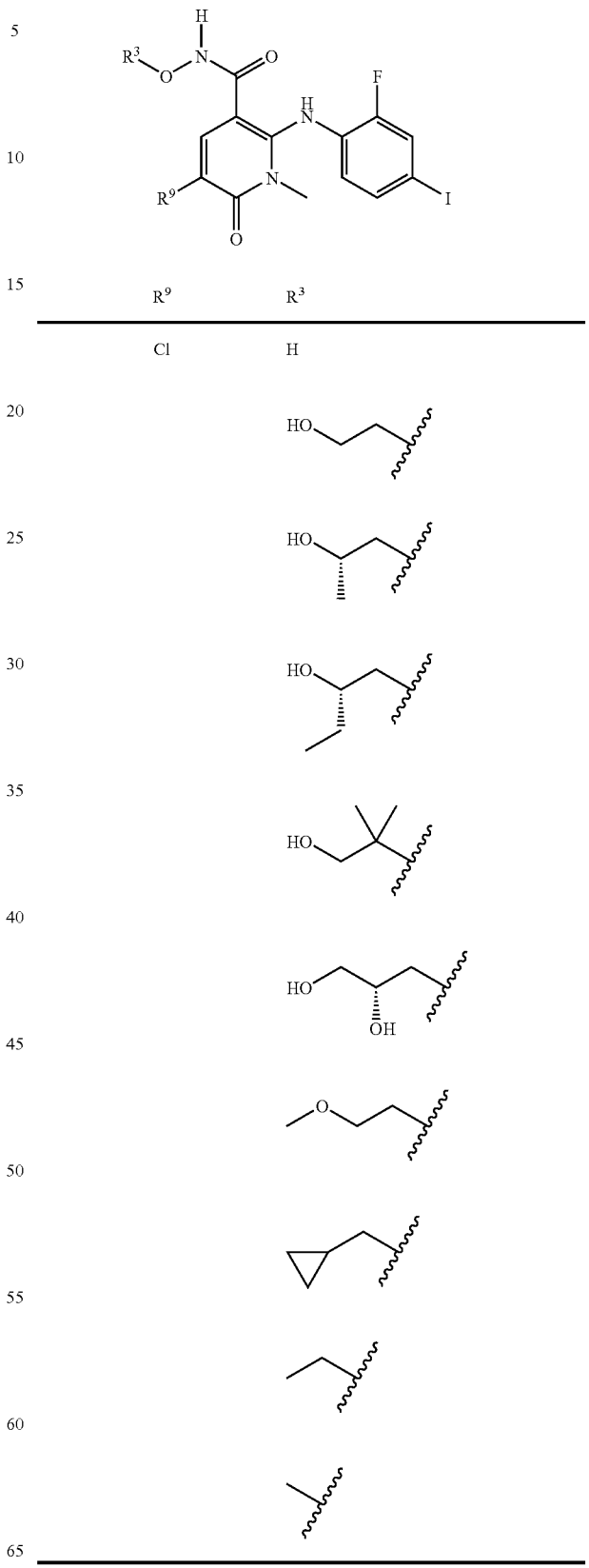 |
| Et | H |
TABLE 3-continued
IVb
| R⁹ | R³ |
|---|---|
| Cl | H |

TABLE 4
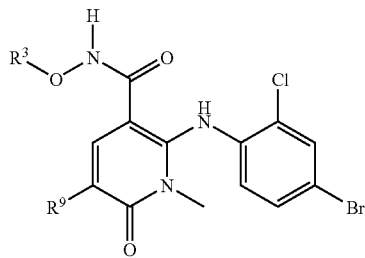
IVc
| R⁹ | R³ |
|---|---|
| Me | H |
| | 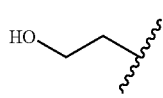 |
| | 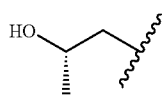 |
| | 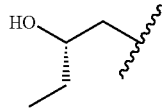 |
| | 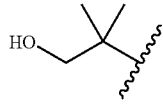 |
| | 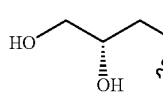 |
| | 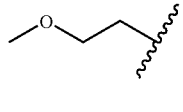 |
| |  |
| | 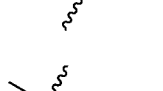 |
| |  |
| Et | H |
| | 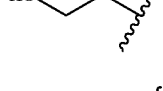 |
TABLE 4-continued
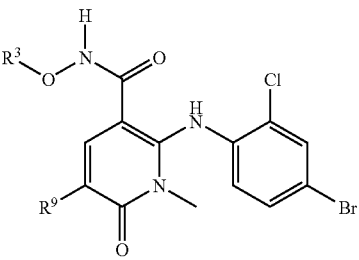
IVc
| R⁹ | R³ |
|---|---|
| | 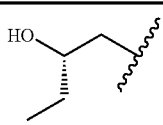 |
| | 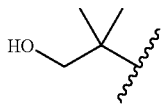 |
| | 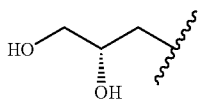 |
| | 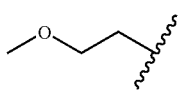 |
| | 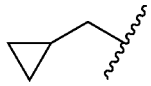 |
| |  |
| Cl | H |
| | 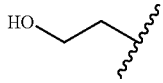 |
| | 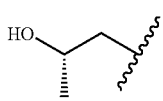 |
| | 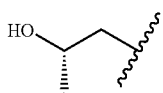 |
| | 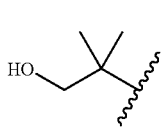 |

TABLE 4-continued
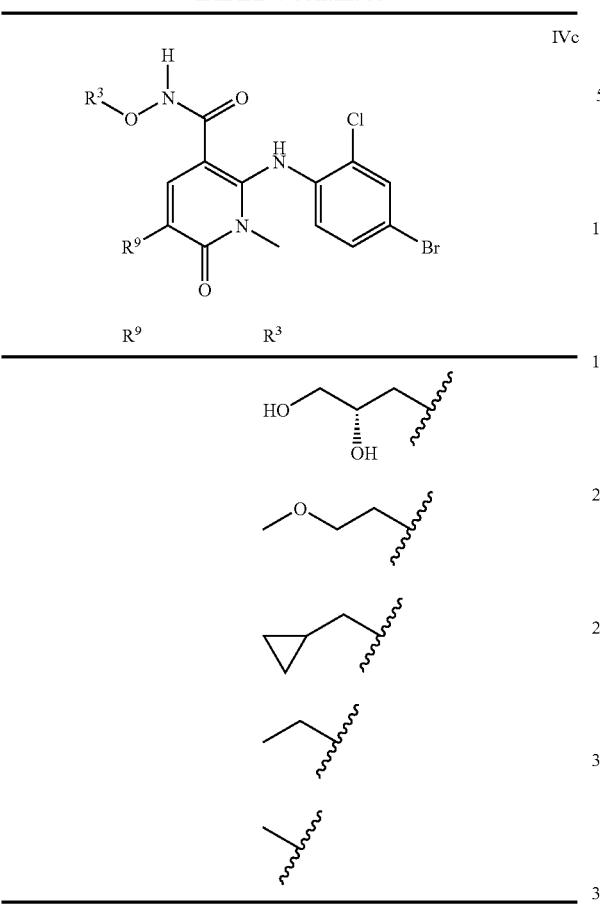
TABLE 5
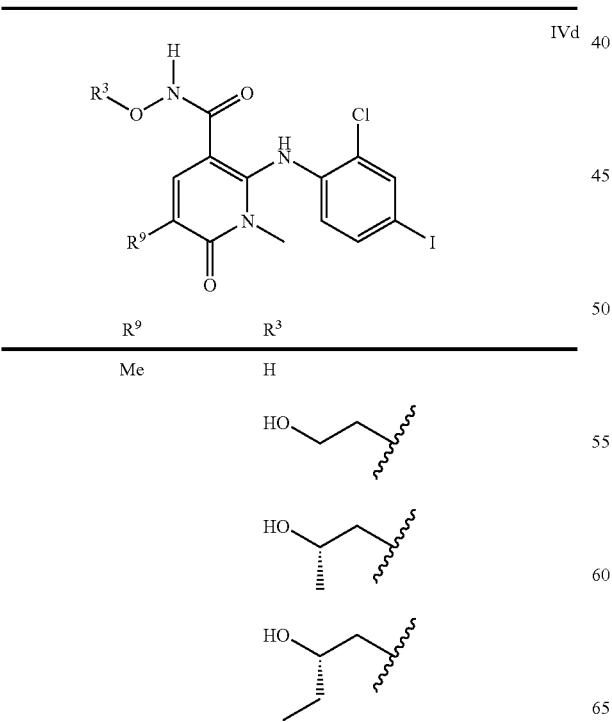
TABLE 5-continued
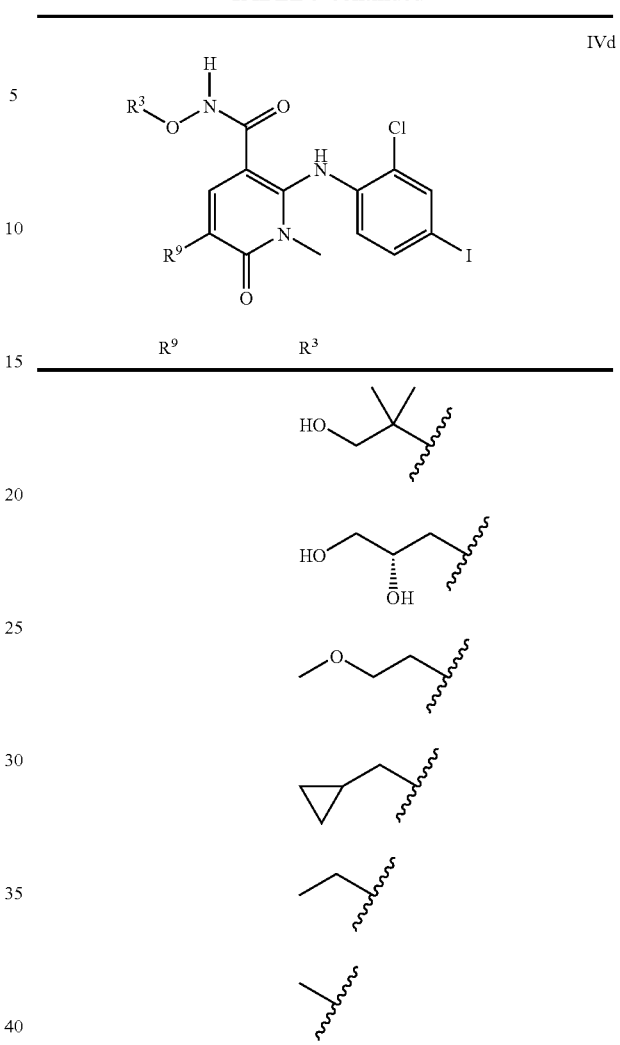
| R⁹ | R³ |
|---|---|
| Et | H |
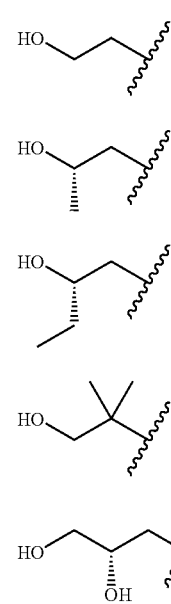

TABLE 5-continued
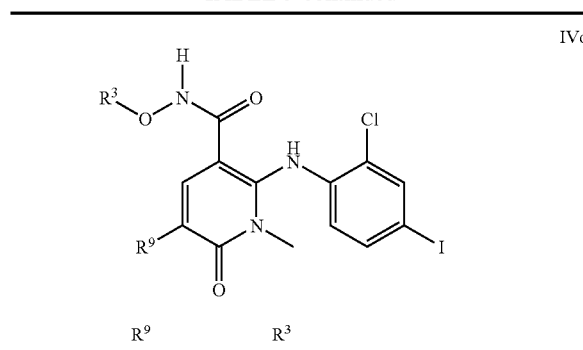
IVd
| R⁹ | R³ |
|---|---|
| | 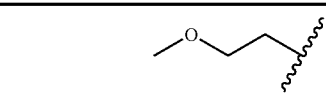 |
| | 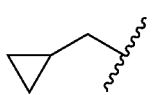 |
| | 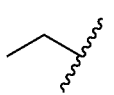 |
| |  |
| Cl | H |
| | 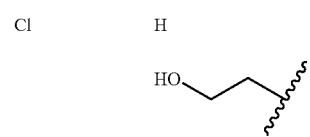 |
| | 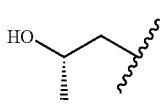 |
| | 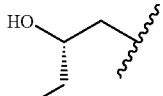 |
| | 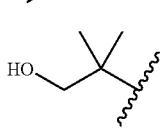 |
| | 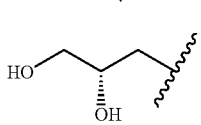 |
| | 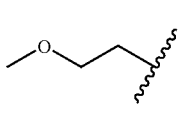 |
| | 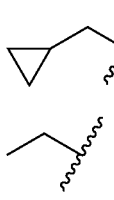 |
TABLE 5-continued
IVd
| R⁹ | R³ |
|---|---|
| |  |
TABLE 6
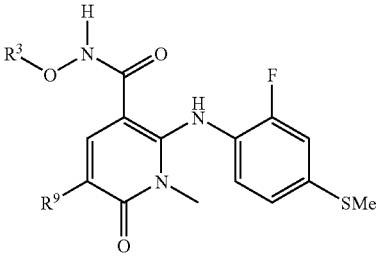
IVe
| R⁹ | R³ |
|---|---|
| Me | H |
| | 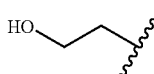 |
| | 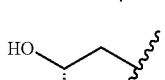 |
| | 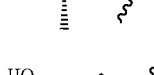 |
| | 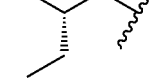 |
| | 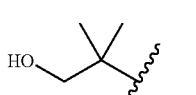 |
| | 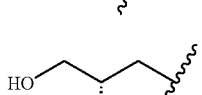 |
| | 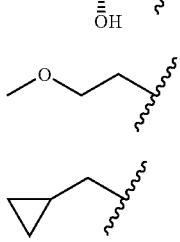 |

TABLE 6-continued
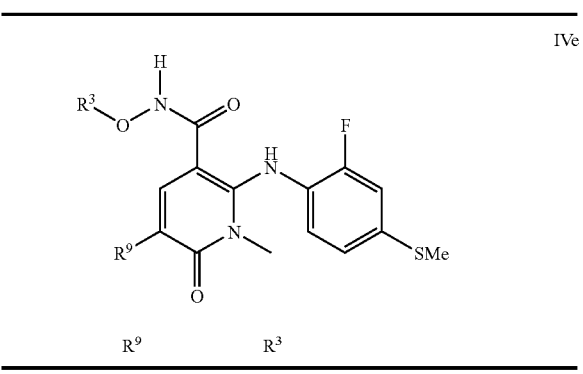
| R⁹ | R³ |
|---|---|
| Et | H |
| | (various R³ groups shown) |
| CN | H |
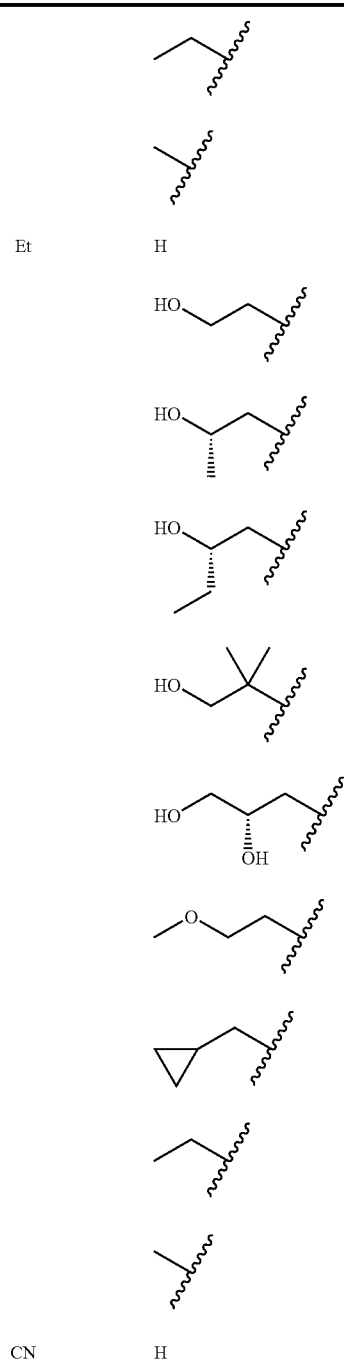
TABLE 6-continued
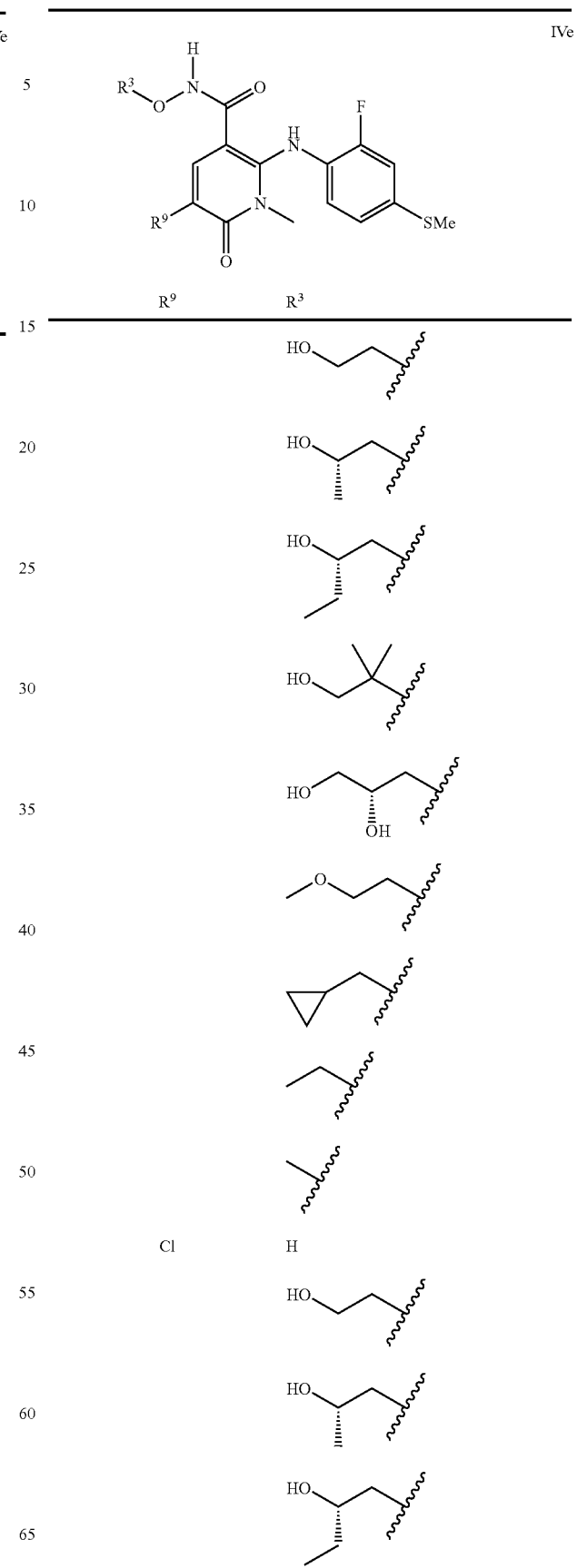
| R⁹ | R³ |
|---|---|
| Cl | H |

TABLE 6-continued
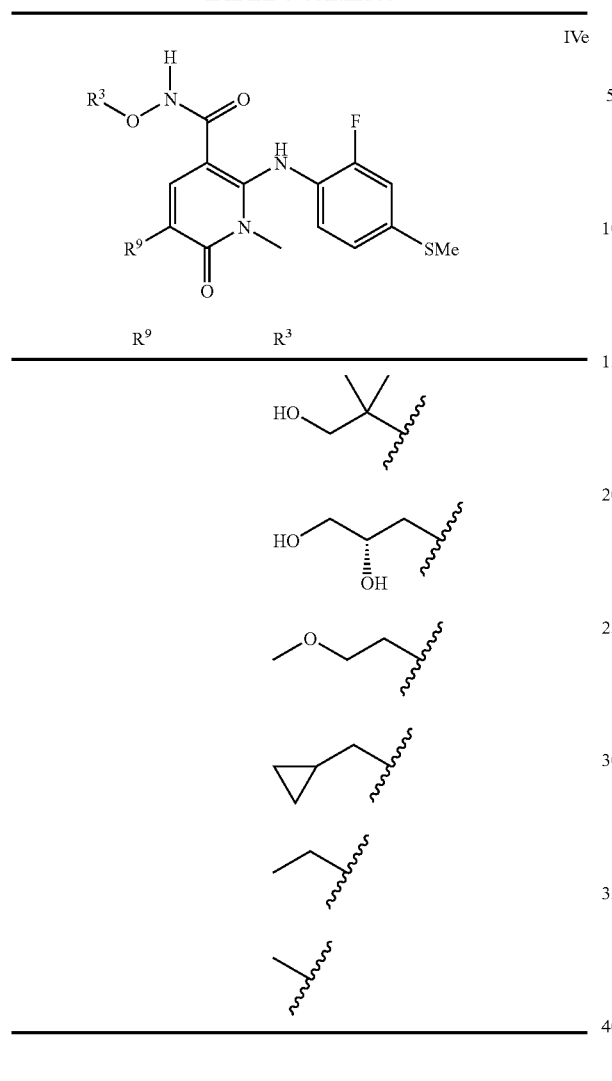
TABLE 7
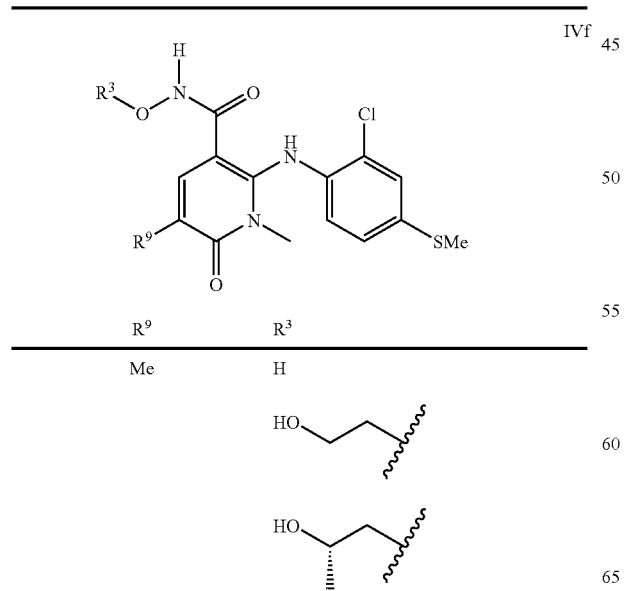
TABLE 7-continued
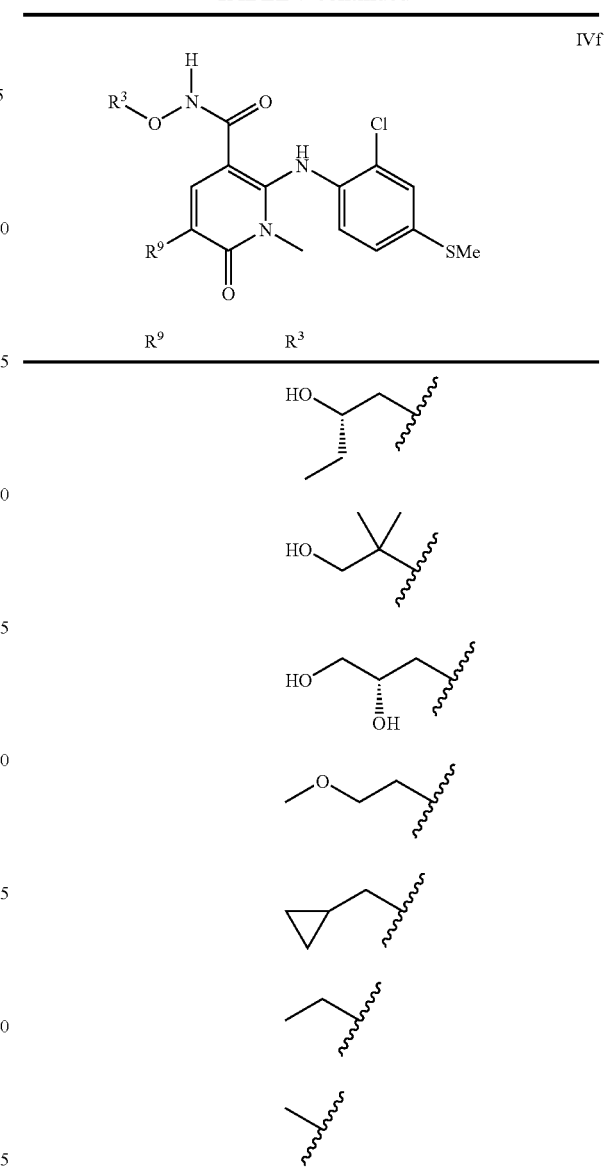
| | |
|---|---|
| Et | H |
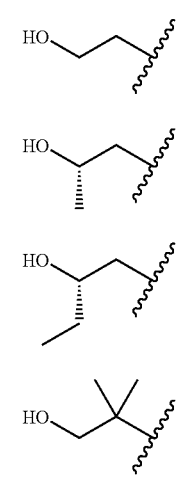

TABLE 7-continued
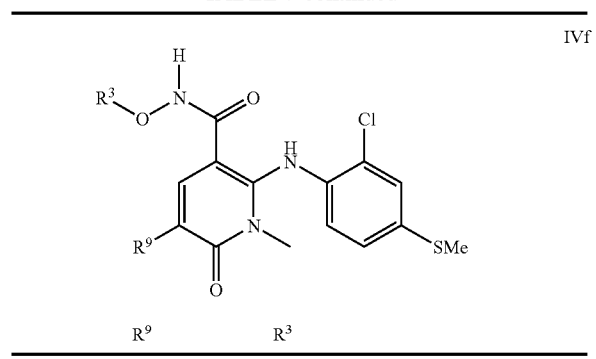
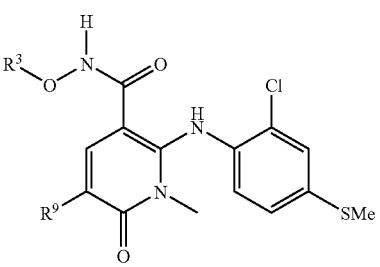
| R⁹ | R³ |
|---|---|
| CN | H |
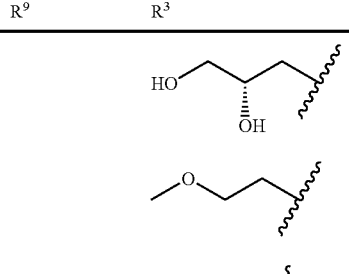
TABLE 7-continued
IVf
| R⁹ | R³ |
|---|---|
| Cl | H |
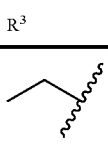
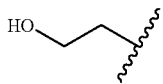
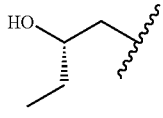
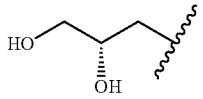
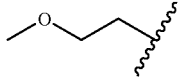
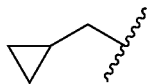
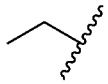

TABLE 8

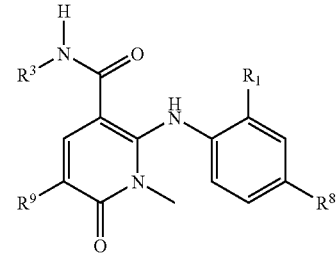

IVg

| R⁹ | R⁸ | R¹ | R³ |
|---|---|---|---|
| Me | I | F | H |
|  |  |  | Me |
|  |  | Cl | H |
|  |  |  | Me |
|  | Br | F | H |
|  |  |  | Me |
|  |  | Cl | H |
|  |  |  | Me |
|  | SMe | F | H |
|  |  |  | Me |
|  |  | Cl | H |
|  |  |  | Me |
| Et | I | F | H |
|  |  |  | Me |
|  |  | Cl | H |
|  |  |  | Me |
|  | Br | F | H |
|  |  |  | Me |
|  |  | Cl | H |
|  |  |  | Me |
|  | SMe | F | H |
|  |  |  | Me |
|  |  | Cl | H |
|  |  |  | Me |
| CN | SMe | F | H |
|  |  |  | Me |
|  |  | Cl | H |
|  |  |  | Me |
| Cl | I | F | H |
|  |  |  | Me |
|  |  | Cl | H |
|  |  |  | Me |
|  | Br | F | H |
|  |  |  | Me |
|  |  | Cl | H |
|  |  |  | Me |
|  | SMe | F | H |
|  |  |  | Me |
|  |  | Cl | H |
|  |  |  | Me |

Additional examples of the invention include the following, which can be made by the methods described above, unless otherwise indicated.

Example 25-A

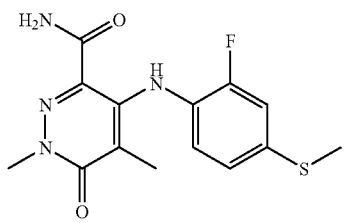

4-(2-Fluoro-4-(methylthio)phenylamino)-1,5-dimethyl-6-oxo-1,6-dihydropyridazine-3-carboxamide MS APCI (−) m/z 321 (M−1) detected; ¹H NMR (400 MHz, CD₃OD) δ 7.09 (dd, 1H), 7.04 (d, 1H), 6.87 (t, 1H), 3.81 (s, 3H), 2.48 (s, 3H), 1.70 (s, 3H).

Example 25-B

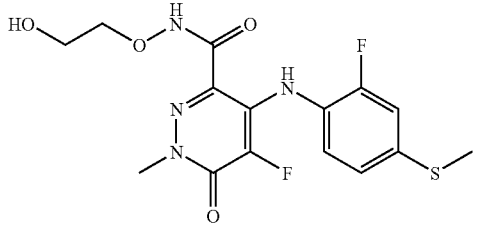

5-Fluoro-4-(2-fluoro-4-(methylthio)phenylamino)-N-(2-hydroxyethoxy)-1-methyl-6-oxo-1,6-dihydropyridazine-3-carboxamide MS APCI (−) m/z 385 (M−1) detected; ¹H NMR (400 MHz, CD₃OD) δ 7.14 (td, 1H), 7.07 (m, 2H), 4.05 (t, 2H), 3.79 (s, 3H), 3.78 (t, 2H), 2.49 (s, 3H).

Example 25-C

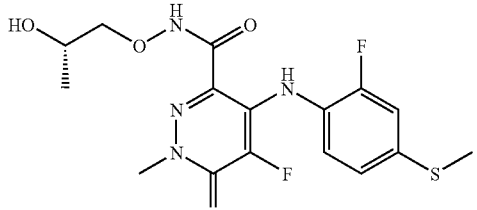

(S)-5-Fluoro-4-(2-fluoro-4-(methylthio)phenylamino)-N-(2-hydroxypropoxy)-1-methyl-6-oxo-1,6-dihydropyridazine-3-carboxamide MS APCI (−) m/z 399 (M−1) detected; ¹H NMR (400 MHz, CD₃OD) δ 7.14 (td, 1H), 7.07 (m, 2H), 4.04 (m, 1H), 3.93 (dd, 1H), 3.81 (m, 1H), 3.80 (s, 3H), 2.49 (s, 3H), 1.18 (d, 3H).

Example 25-D

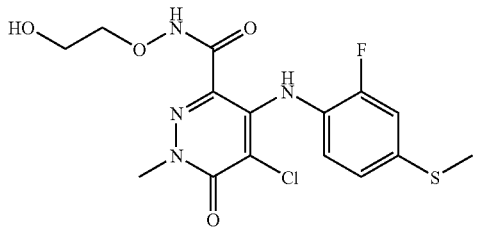

5-Chloro-4-(2-fluoro-4-(methylthio)phenylamino)-N-(2-hydroxyethoxy)-1-methyl-6-oxo-1,6-dihydropyridazine-3-carboxamide MS APCI (−) m/z 401, 403 (M−1, Cl pattern) detected; ¹H NMR (400 MHz, CD₃OD) δ 7.06 (m, 3H), 3.94 (t, 2H), 3.81 (s, 3H), 3.73 (t, 2H), 2.49 (s, 3H).

Example 25-E

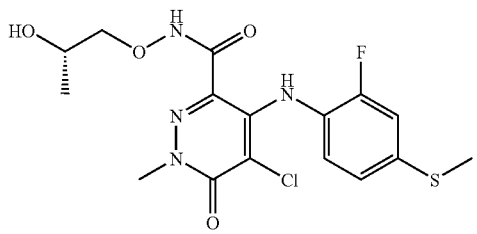

(S)-5-Chloro-4-(2-fluoro-4-(methylthio)phenylamino)-N-(2-hydroxypropoxy)-1-methyl-6-oxo-1,6-dihydropyridazine-3-carboxamide MS APCI (−) m/z 415, 417 (M−1, Cl pattern) detected; $^1$H NMR (400 MHz, CD$_3$OD) δ 7.06 (m, 3H), 3.98 (m, 1H), 3.81 (m, 1H), 3.80 (s, 3H), 3.69 (dd, 1H), 2.49 (s, 3H), 1.16 (d, 3H).

Example 25-F

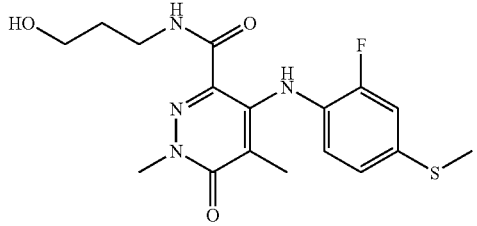

4-(2-Fluoro-4-(methylthio)phenylamino)-N-(3-hydroxypropyl)-1,5-dimethyl-6-oxo-1,6-dihydropyridazine-3-carboxamide MS APCI (−) m/z 379 (M−1) detected; $^1$H NMR (400 MHz, CD$_3$OD) δ 7.09 (dd, 1H), 7.03 (d, 1H), 6.86 (t, 1H), 3.81 (s, 3H), 3.64 (t, 2H), 3.43 (t, 2H), 2.47 (s, 3H), 1.80 (m, 2H), 1.71 (s, 3H).

Example 25-G

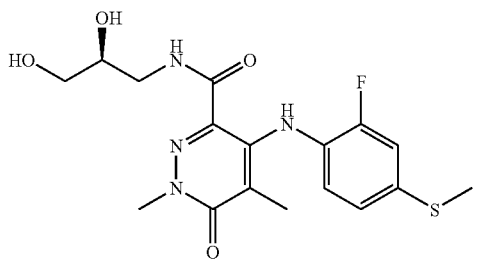

(S)—N-(2,3-Dihydroxypropyl)-4-(2-fluoro-4-(methylthio)phenylamino)-1,5-dimethyl-6-oxo-1,6-dihydropyridazine-3-carboxamide MS APCI (−) m/z 395 (M−1) detected; $^1$H NMR (400 MHz, CD$_3$OD) δ 7.10 (dd, 1H), 7.03 (dd, 1H), 6.86 (t, 1H), 3.81 (s, 3H), 3.80 (m, 1H), 3.51 (m, 3H), 3.37 (dd, 1H), 2.47 (s, 3H), 1.71 (s, 3H).

Example 25-H

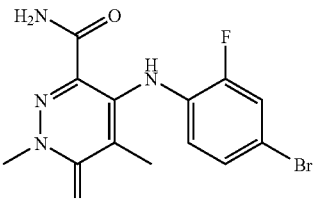

4-(4-Bromo-2-fluorophenylamino)-1,5-dimethyl-6-oxo-1,6-dihydropyridazine-3-carboxamide MS APCI (−) m/z 353, 355 (M−1, Br pattern) detected; $^1$H NMR (400 MHz, CD$_3$OD) δ 7.38 (dd, 1H), 7.27 (m, 1H), 6.80 (t, 1H), 3.82 (s, 3H), 1.72 (s, 3H).

Example 25-I

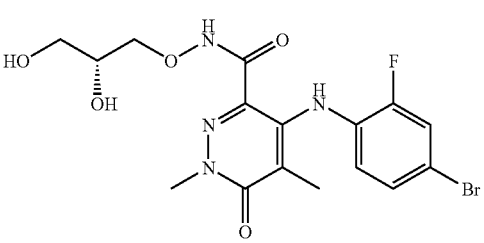

(R)-4-(4-Bromo-2-fluorophenylamino)-N-(2,3-dihydroxypropoxy)-1,5-dimethyl-6-oxo-1,6-dihydropyridazine-3-carboxamide MS APCI (−) m/z 443, 445 (M−1, Br pattern) detected; $^1$H NMR (400 MHz, CD$_3$OD) δ 7.39 (dd, 1H), 7.27 (m, 1H), 6.79 (t, 1H), 4.03 (m, 1H), 3.89 (m, 2H), 3.80 (s, 3H), 3.59 (m, 2H), 1.77 (s, 3H).

Example 25-J

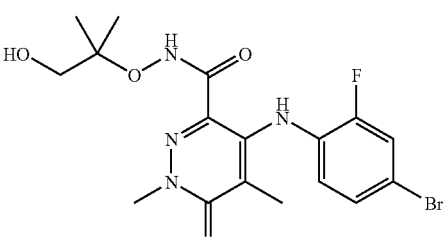

4-(4-Bromo-2-fluorophenylamino)-N-(1-hydroxy-2-methylpropan-2-yloxy)-1,5-dimethyl-6-oxo-1,6-dihydropyridazine-3-carboxamide MS APCI (−) m/z 441, 443 (M−1, Br pattern) detected; $^1$H NMR (400 MHz, CD$_3$OD) δ 7.38 (dd, 1H), 7.27 (d, 1H), 6.79 (t, 1H), 3.81 (s, 3H), 3.38 (s, 2H), 1.78 (s, 3H), 1.25 (s, 6H).

Example 25-K

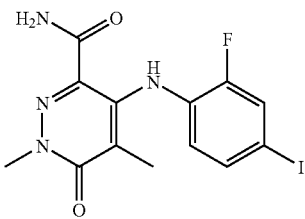

4-(2-Fluoro-4-iodophenylamino)-1,5-dimethyl-6-oxo-1,6-dihydropyridazine-3-carboxamide MS APCI (−) m/z 401 (M−1) detected; $^1$H NMR (400 MHz, DMSO-d$_6$) δ 9.75 (s, 1H), 8.25 (s, 1H), 7.90 (s, 1H), 7.65 (s, 1H), 7.43 (s, 1H), 6.63 (t, 1H), 3.71 (s, 3H), 1.63 (s, 3H).

Example 25-L

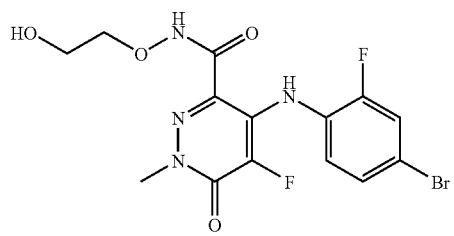

4-(4-Bromo-2-fluorophenylamino)-5-fluoro-N-(2-hydroxyethoxy)-1-methyl-6-oxo-1,6-dihydropyridazine-3-carboxamide MS APCI (−) m/z 417, 419 (M−1, Br pattern) detected; $^1$H NMR (400 MHz, CDCl$_3$) δ 9.66 (br. s, 1H), 9.30 (br. s, 1H), 7.28 (m, 2H), 6.97 (td, 1H), 4.11 (t, 2H), 3.84 (t, 2H), 3.82 (s, 3H), 3.51 (t, 1H).

Example 25-M

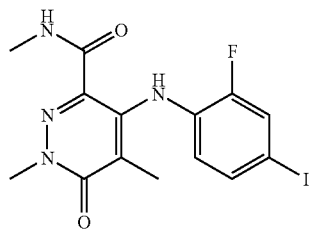

4-(2-Fluoro-4-iodophenylamino)-N,1,5-trimethyl-6-oxo-1,6-dihydropyridazine-3-carboxamide MS APCI (−) m/z 415 (M−1) detected; $^1$H NMR (400 MHz, CD$_3$OD) δ 7.52 (dd, 1H), 7.44 (m, 1H), 6.61 (t, 1H), 3.81 (s, 3H), 2.87 (s, 3H), 1.74 (s, 3H).

Example 25-N

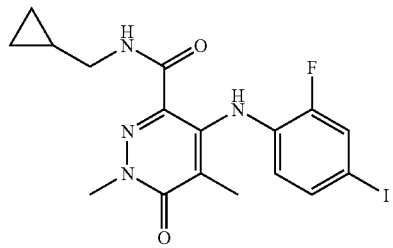

N-(Cyclopropylmethyl)-4-(2-fluoro-4-iodophenylamino)-1,5-dimethyl-6-oxo-1,6-dihydropyridazine-3-carboxamide MS APCI (−) m/z 455 (M−1) detected; $^1$H NMR (400 MHz, CD$_3$OD) δ 7.52 (dd, 1H), 7.44 (dd, 1H), 6.62 (t, 1H), 3.83 (s, 3H), 3.18 (d, 2H), 1.75 (s, 3H), 1.06 (m, 1H), 0.51 (dd, 2H), 0.27 (dd, 2H).

Example 25-O

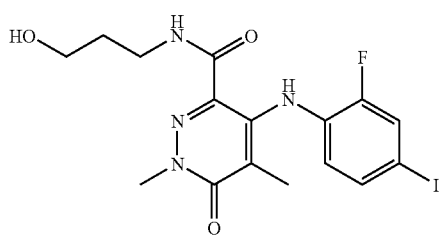

4-(2-Fluoro-4-iodophenylamino)-N-(3-hydroxypropyl)-1,5-dimethyl-6-oxo-1,6-dihydropyridazine-3-carboxamide MS APCI (−) m/z 459 (M−1) detected; $^1$H NMR (400 MHz, CD$_3$OD) δ 7.52 (dd, 1H), 7.44 (dd, 1H), 6.62 (t, 1H), 3.81 (s, 3H), 3.63 (t, 2H), 3.43 (t, 2H), 1.79 (m, 2H), 1.74 (s, 3H).

Example 25-P

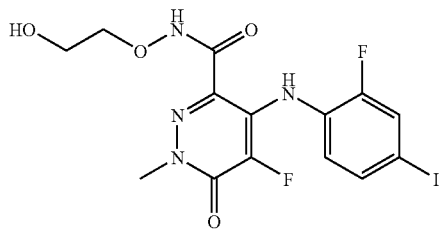

5-Fluoro-4-(2-fluoro-4-iodophenylamino)-N-(2-hydroxyethoxy)-1-methyl-6-oxo-1,6-dihydropyridazine-3-carboxamide MS APCI (−) m/z 465 (M−1) detected; $^1$H NMR (400 MHz, CD$_3$OD) δ 7.55 (dd, 1H), 7.50 (d, 1H), 6.95 (td, 1H), 4.05 (t, 2H), 3.80 (s, 3H), 3.78 (t, 2H).

Example 25-Q

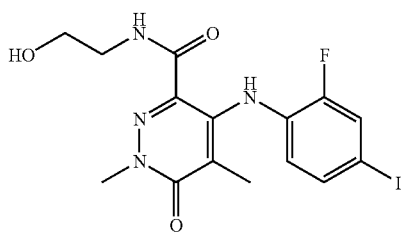

4-(2-Fluoro-4-iodophenylamino)-N-(2-hydroxy-ethyl)-1,5-dimethyl-6-oxo-1,6-dihydropyridazine-3-carboxamide MS APCI (−) m/z 445 (M−1) detected; $^1$H NMR (400 MHz, CD$_3$OD) δ 7.52 (dd, 1H), 7.44 (dd, 1H), 6.62 (t, 1H), 3.82 (s, 3H), 3.68 (t, 2H), 3.46 (t, 2H), 1.74 (s, 3H).

Example 25-R

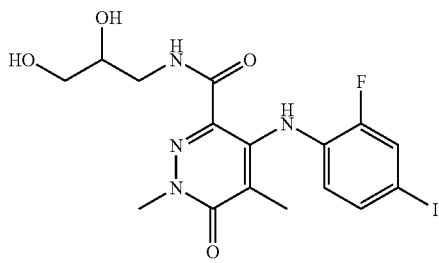

N-(2,3-Dihydroxypropyl)-4-(2-fluoro-4-iodophenylamino)-1,5-dimethyl-6-oxo-1,6-dihydropyridazine-3-carboxamide MS APCI (−) m/z 475 (M−1) detected; $^1$H NMR (400 MHz, CD$_3$OD) δ 7.52 (dd, 1H), 7.44 (dd, 1H), 6.62 (t, 1H), 3.82 (s, 3H), 3.80 (m, 1H), 3.52 (m, 3H), 3.36 (dd, 1H), 1.74 (s, 3H).

Example 25-S

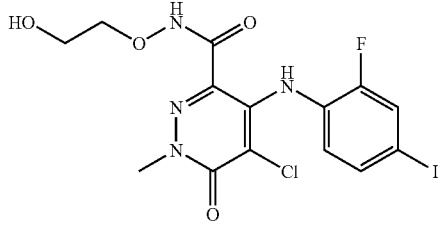

5-Chloro-4-(2-fluoro-4-iodophenylamino)-N-(2-hydroxyethoxy)-1-methyl-6-oxo-1,6-dihydropyridazine-3-carboxamide MS APCI (−) m/z 481, 483 (M−1, Cl pattern) detected; $^1$H NMR (400 MHz, CD$_3$OD) δ 7.53 (dd, 1H), 7.49 (d, 1H), 6.88 (t, 1H), 3.97 (t, 2H), 3.81 (s, 3H), 3.74 (t, 2H).

Example 25-T

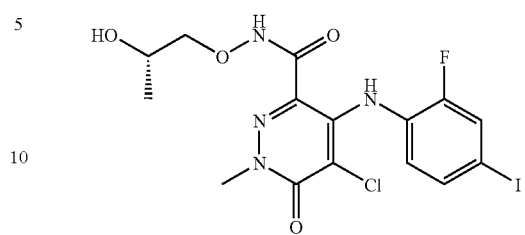

(S)-5-Chloro-4-(2-fluoro-4-iodophenylamino)-N-(2-hydroxypropoxy)-1-methyl-6-oxo-1,6-dihydropyridazine-3-carboxamide MS APCI (−) m/z 495, 496 (M−1, Cl pattern) detected; $^1$H NMR (400 MHz, CD$_3$OD) δ 7.53 (dd, 1H), 7.49 (d, 1H), 6.88 (t, 1H), 3.99 (m, 1H), 3.83 (m, 1H), 3.81 (s, 3H), 3.71 (dd, 1H), 1.17 (d, 3H).

Example 25-U

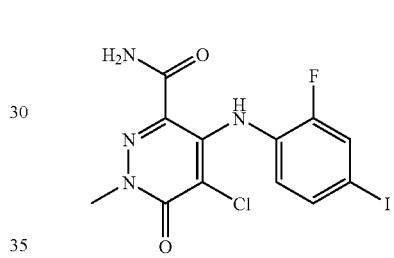

5-Chloro-4-(2-fluoro-4-iodophenylamino)-1-methyl-6-oxo-1,6-dihydropyridazine-3-carboxamide MS APCI (−) m/z 421, 423 (M−1, Cl pattern) detected; $^1$H NMR (400 MHz, CDCl$_3$/CD$_3$OD) δ 7.56 (td, 1H), 7.46 (m, 1H), 6.82 (t, 1H), 3.87 (s, 3H).

Example 25-V

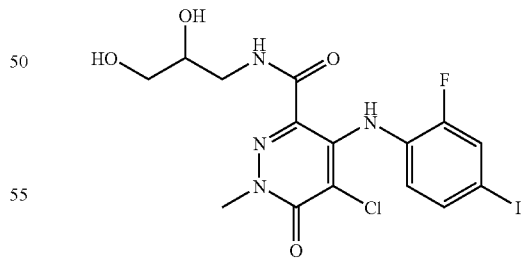

5-Chloro-N-(2,3-dihydroxypropyl)-4-(2-fluoro-4-iodophenylamino)-1-methyl-6-oxo-1,6-dihydropyridazine-3-carboxamide MS APCI (+) m/z 497, 499 (M+1, Cl pattern) detected; $^1$H NMR (400 MHz, CD$_3$OD) δ 7.53 (dd, 1H), 7.49 (d, 1H), 6.86 (t, 1H), 3.84 (s, 3H), 3.80 (m, 1H), 3.55 (d, 2H), 3.50 (m, 1H), 3.37 (dd, 1H).

Example 25-W

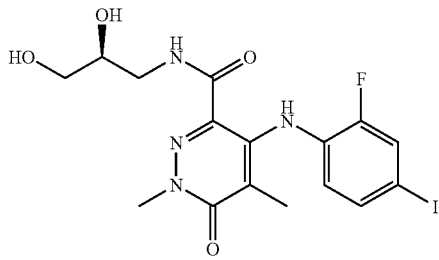

(S)—N-(2,3-Dihydroxypropyl)-4-(2-fluoro-4-iodophenylamino)-1,5-dimethyl-6-oxo-1,6-dihydropyridazine-3-carboxamide MS APCI (−) m/z 475 (M−1) detected; $^1$H NMR (400 MHz, CD$_3$OD) δ 7.52 (dd, 1H), 7.44 (d, 1H), 6.62 (t, 1H), 3.82 (s, 3H), 3.80 (m, 1H), 3.52 (m, 3H), 3.36 (dd, 1H), 1.74 (s, 3H).

Example 25-X

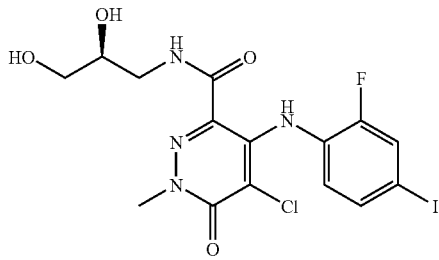

(S)-5-Chloro-N-(2,3-dihydroxypropyl)-4-(2-fluoro-4-iodophenylamino)-1-methyl-6-oxo-1,6-dihydropyridazine-3-carboxamide MS APCI (+) m/z 497, 499 (M+1, Cl pattern) detected; $^1$H NMR (400 MHz, CD$_3$OD) δ 7.52 (dd, 1H), 7.48 (d, 1H), 6.86 (t, 1H), 3.84 (s, 3H), 3.80 (m, 1H), 3.55 (d, 2H), 3.51 (d, 1H), 3.37 (dd, 1H).

Example 25-Y

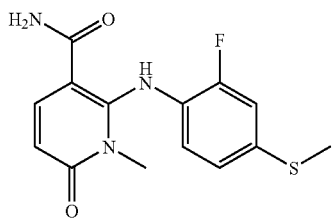

2-(2-fluoro-4-(methylthio)phenylamino)-1-methyl-6-oxo-1,6-dihydropyridine-3-carboxamide MS APCI (+) m/z 308 (M+1) pattern detected; $^1$H NMR (400 MHz, DMSO-d$_6$) δ 11.38 (s, 1H), 7.92 (br s, 1H), 7.89 (d, 1H), 7.45 (br s, 1H), 7.25 (dd, 1H), 7.04 (dd, 1H), 6.88 (t, 1H), 6.09 (d, 1H), 3.07 (s, 3H), 2.48 (s, 3H).

Example 25-Z

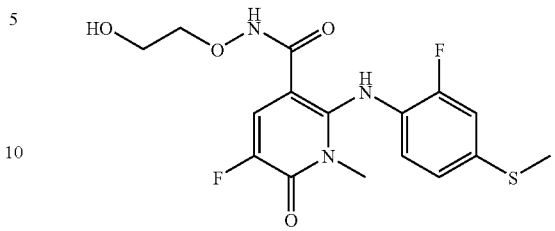

5-fluoro-2-(2-fluoro-4-(methylthio)phenylamino)-N-(2-hydroxyethoxy)-1-methyl-6-oxo-1,6-dihydropyridine-3-carboxamide Step A: Preparation of 2-chloro-5-fluoro-6-oxo-1,6-dihydropyridine-3-carboxylic acid: A mixture of 2,6-dichloro-5-fluoronicotinic acid (15.00 g, 71.43 mmol, Lancaster Synthesis) and 2 N NaOH (178.6 ml, 357.2 mmol) was stirred at reflux for 2 hours and then at room temperature for 16 hours. The reaction mixture was cooled to 0° C. and acidified with 12 N HCl (32.74 ml, 392.9 mmol). The mixture was cooled for 30 minutes in an ice bath, the solid filtered and washed with H$_2$O. The isolated solid was slurried in warm EtOH, filtered and then washed with warm EtOH. The solids were collected and dried under vacuum overnight to yield the desired product (6.4 g, 47%) as a beige solid.

Step B: Preparation of methyl 2-chloro-5-fluoro-1-methyl-6-oxo-1,6-dihydropyridine-3-carboxylate: To a solution of 2-chloro-5-fluoro-6-oxo-1,6-dihydropyridine-3-carboxylic acid (6.37 g, 33.26 mmol) in DMF (250 mL) at 0° C. was added LiH (95%, 0.661 g, 83.14 mmol). The reaction mixture was stirred for 45 minutes, and then iodomethane (4.56 mL, 73.16 mmol) was added. The reaction mixture was stirred at room temperature for 2 hours and then quenched with 2 M HCl until the pH of the reaction mixture was 6-7. The reaction mixture was diluted with EtOAc and saturated NaCl and the layers separated. The aqueous layer was back extracted with EtOAc (1×). The combined organic layers were dried (Na$_2$SO$_4$) and concentrated under reduced pressure to yield a crude yellow oil. HPLC analysis showed two products in a 5:1 ratio that were separated by flash column chromatography (methylene chloride/EtOAc, 15:1) to give the desired product (5.40 g, 74%) as a pale yellow solid. The minor product was also isolated as a pale yellow crystalline solid and identified as the regioisomer methyl 2-chloro-5-fluoro-6-methoxynicotinate.

Step C: Preparation of methyl 5-fluoro-2-(2-fluoro-4-(methylthio)phenylamino)-1-methyl-6-oxo-1,6-dihydropyridine-3-carboxylate: To a solution of 2-fluoro-4-(methylthio)aniline (0.236 g, 1.50 mmol) in THF (10 mL) at −78° C. under N$_2$ was added lithium bis(trimethylsilyl)amide (3.42 ml, 3.42 mmol, 1 M solution in hexanes) dropwise. The reaction mixture was stirred for one hour at −78° C. after the addition was complete. Methyl 2-chloro-5-fluoro-1-methyl-6-oxo-1,6-dihydropyridine-3-carboxylate (0.300 g, 1.37 mmol) was then added dropwise as a solution in THF (5 mL) and the reaction mixture was stirred for 30 minutes at −78° C. The reaction was quenched by the addition of 1 M HCl until the pH of the reaction mixture was 5, and then diluted with EtOAc and saturated NaCl. The organic layer was separated, dried (Na$_2$SO$_4$), and concentrated under reduced pressure. Purification by flash column chromatography (methylene chloride/EtOAc, 15:1) gave pure desired product (0.359 g, 75%) as a white solid.

Step D: Preparation of 5-fluoro-2-(2-fluoro-4-(methylthio)phenylamino)-1-methyl-6-oxo-N-(2-(vinyloxy)ethoxy)-1,6-dihydropyridine-3-carboxamide: To a mixture of methyl 5-fluoro-2-(2-fluoro-4-(methylthio)phenylamino)-1-methyl-6-oxo-1,6-dihydropyridine-3-carboxylate (0.100 g, 0.294 mmol) and O-(2-(vinyloxy)ethyl)hydroxylamine (0.045 ml, 0.441 mmol) in THF (2 mL) at 0° C. was added lithium bis(trimethylsilyl)amide (1.18 ml, 1.18 mmol, 1 M solution in hexanes) dropwise. The reaction mixture was stirred for 20 minutes, quenched with 1 M HCl, and then partitioned between EtOAc and sat NaCl. The layers were separated and the aqueous layer was backextracted with EtOAc (1×). The combined organic layers were dried ($Na_2SO_4$), filtered and concentrated under reduced pressure to yield a crude yellow solid that was used without purification in the next step.

Step E: Preparation of 5-fluoro-2-(2-fluoro-4-(methylthio)phenylamino)-N-(2-hydroxyethoxy)-1-methyl-6-oxo-1,6-dihydropyridine-3-carboxamide: To a solution of 5-fluoro-2-(2-fluoro-4-(methylthio)phenylamino)-1-methyl-6-oxo-N-(2-(vinyloxy)ethoxy)-1,6-dihydropyridine-3-carboxamide (0.121 g, 0.294 mmol) in EtOH (3 mL) was added 2 M HCl (0.75 mL). The reaction mixture was stirred at room temperature for 16 hours. The pH of the reaction mixture was adjusted to pH 7 with 1 M NaOH. The reaction mixture was diluted with EtOAc and $H_2O$. The organic layer was separated and washed with saturated NaCl. The combined aqueous layers were back extracted with EtOAc (1×). The combined organic layers were dried ($Na_2SO_4$) and concentrated under reduced pressure. Purification by silica gel flash column chromatography (methylene chloride/MeOH, 15:1) gave 5-fluoro-2-(2-fluoro-4-(methylthio)phenylamino)-N-(2-hydroxyethoxy)-1-methyl-6-oxo-1,6-dihydropyridine-3-carboxamide (0.079 g; 70% over two steps) as a white solid. MS ESI (+) m/z 386 (M+1) pattern detected; $^1$H NMR (400 MHz, DMSO-$d_6$) δ 11.54 (br s, 1H), 9.65 (br s, 1H), 7.65 (d, 1H), 7.23 (dd, 1H), 6.99 (dd, 1H), 6.81 (t, 1H), 4.67 (t, 1H), 3.74 (t, 2H), 3.51 (q, 2H), 3.25 (s, 3H), 2.46 (s, 3H).

Example 25-AA

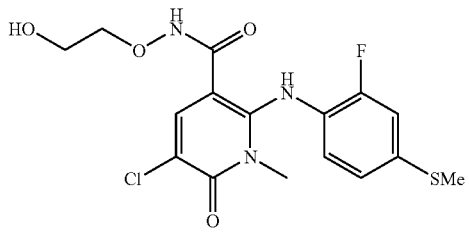

5-chloro-2-(2-fluoro-4-(methylthio)phenylamino)-N-(2-hydroxyethoxy)-1-methyl-6-oxo-1,6-dihydropyridine-3-carboxamide MS ESI (+) m/z 402, 404 (M+, Cl pattern) detected; $^1$H NMR (400 MHz, DMSO-$d_6$) δ 11.59 (br s, 1H), 10.00 (br s, 1H), 7.93 (s, 1H), 7.23 (dd, 1H), 7.01 (dd, 1H), 6.93 (t, 1H), 4.66 (t, 1H), 3.73 (t, 2H), 3.51 (m, 2H), 3.24 (s, 3H), 2.47 (s, 3H).

Example 25-BB

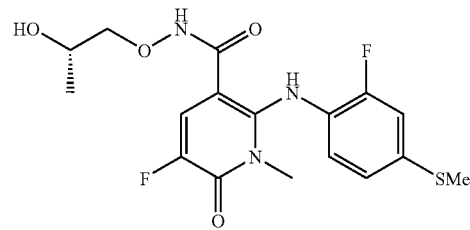

(S)-5-fluoro-2-(2-fluoro-4-(methylthio)phenylamino)-N-(2-hydroxypropoxy)-1-methyl-6-oxo-1,6-dihydropyridine-3-carboxamide MS APCI (+) m/z 400 (M+1) pattern detected; $^1$H NMR (400 MHz, DMSO-$d_6$) δ 11.54 (br s, 1H), 9.61 (br s, 1H), 7.64 (d, 1H), 7.22 (dd, 1H), 6.99 (dd, 1H), 6.81 (t, 1H), 4.73 (s, 1H), 3.73 (m, 1H), 3.54 (d, 2H), 3.25 (s, 3H), 2.46 (s, 3H), 1.01 (d, 3H).

Example 25-CC

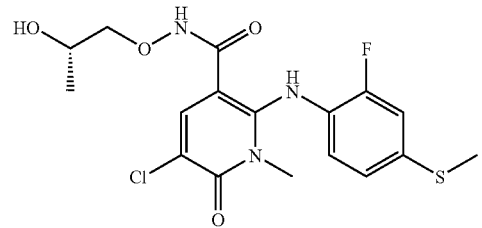

(S)-5-chloro-2-(2-fluoro-4-(methylthio)phenylamino)-N-(2-hydroxypropoxy)-1-methyl-6-oxo-1,6-dihydropyridine-3-carboxamide MS APCI (+) m/z 416, 418 (M+, Cl pattern) detected; $^1$H NMR (400 MHz, DMSO-$d_6$) δ 11.59 (br s, 1H), 9.94 (br s, 1H), 7.92 (s, 1H), 7.23 (dd, 1H), 7.01 (dd, 1H), 6.94 (t, 1H), 4.71 (d, 1H), 3.75 (m, 1H), 3.54 (d, 2H), 3.24 (s, 3H), 2.47 (s, 3H), 1.02 (d, 3H).

Example 25-DD

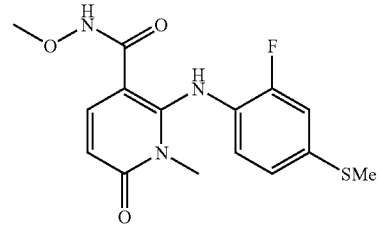

2-(2-fluoro-4-(methylthio)phenylamino)-N-methoxy-1-methyl-6-oxo-1,6-dihydropyridine-3-carboxamide MS ESI (+) m/z 338 (M+1) pattern detected; $^1$H NMR (400 MHz, CDCl$_3$) δ 10.33 (s, 1H), 8.39 (s, 1H), 7.40 (d, 1H), 7.02 (dd, 1H), 6.96 (dd, 1H), 6.75 (t, 1H), 6.20 (d, 1H), 3.83 (s, 3H), 3.23 (s, 3H), 2.47 (s, 3H).

Example 25-FF

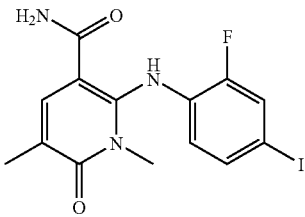

2-(2-fluoro-4-iodophenylamino)-1,5-dimethyl-6-oxo-1,6-dihydropyridine-3-carboxamide MS ESI (+) m/z 402 (M+1) pattern detected; $^1$H NMR (400 MHz, DMSO-d$_6$) δ 10.75 (s, 1H), 7.85 (br s, 1H), 7.78 (s, 1H), 7.66 (d, 1H), 7.40 (m, 2H), 6.54 (t, 1H), 3.13 (s, 3H), 2.00 (s, 3H).

Example 25-HH

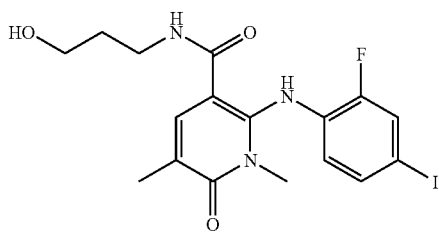

2-(2-fluoro-4-iodophenylamino)-N-(3-hydroxypropyl)-1,5-dimethyl-6-oxo-1,6-dihydropyridine-3-carboxamide MS ESI (+) m/z 460 (M+1) pattern detected; $^1$H NMR (400 MHz, DMSO-d$_6$) δ 10.34 (s, 1H), 8.27 (t, 1H), 7.72 (s, 1H), 7.64 (dd, 1H), 7.38 (dd, 1H), 6.50 (t, 1H), 4.41 (t, 1H), 3.17 (s, 5H), 2.01 (s, 3H), 1.55 (s, 2H).

Example 25-JJ

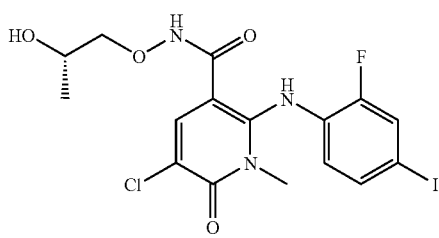

(S)-5-chloro-2-(2-fluoro-4-iodophenylamino)-N-(2-hydroxypropoxy)-1-methyl-6-oxo-1,6-dihydropyridine-3-carboxamide MS APCI (+) m/z 460 (M+1) pattern detected; $^1$H NMR (400 MHz, DMSO-d$_6$) δ 11.54 (br s, 1H), 9.62 (br s, 1H), 7.86 (s, 1H), 7.62 (dd, 1H), 7.38 (dd, 1H), 6.69 (t, 1H), 4.69 (m, 1H), 3.46 (m, 2H), 3.27 (s, 3H), 0.99 (d, 3H).

Example 25-KK

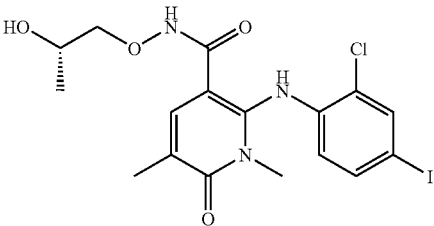

(S)-2-(2-chloro-4-iodophenylamino)-N-(2-hydroxypropoxy)-1,5-dimethyl-6-oxo-1,6-dihydropyridine-3-carboxamide MS APCI (+) m/z 492 (M+1) pattern detected; $^1$H NMR (400 MHz, CD$_3$OD) δ 7.79 (d, 1H), 7.58 (m, 1H), 7.52 (dd, 1H), 6.39 (d, 1H), 3.87 (m, 1H), 3.73 (dd, 1H), 3.62 (dd, 1H), 3.35 (s, 3H), 2.13 (s, 3H), 1.10 (d, 3H).

Example 25-LL

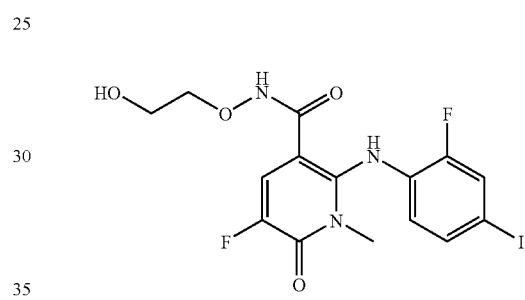

5-fluoro-2-(2-fluoro-4-iodophenylamino)-N-(2-hydroxyethoxy)-1-methyl-6-oxo-1,6-dihydropyridine-3-carboxamide MS ESI (+) m/z 466 (M+1) pattern detected; $^1$H NMR (400 MHz, DMSO-d$_6$) δ 11.53 (br s, 1H), 9.37 (br s, 1H), 7.64 (dd, 1H), 7.62 (d, 1H), 7.37 (dd, 1H), 6.61 (t, 1H), 4.68 (t, 1H), 3.69 (t, 2H), 3.49 (q, 2H), 3.30 (s, 3H).

Example 25-MM

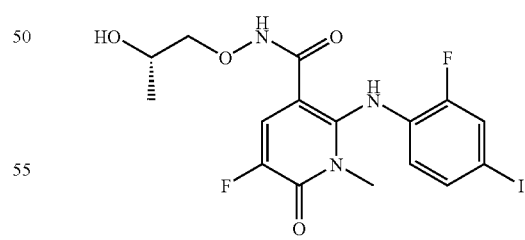

(S)-5-fluoro-2-(2-fluoro-4-iodophenylamino)-N-(2-hydroxypropoxy)-1-methyl-6-oxo-1,6-dihydropyridine-3-carboxamide MS APCI (+) m/z 480 (M+1) pattern detected; $^1$H NMR (400 MHz, DMSO-d$_6$) δ 11.49 (br s, 1H), 9.48 (br s, 1H), 7.61 (m, 2H), 7.36 (m, 1H), 6.59 (t, 1H), 4.77 (br s, 1H), 3.69 (m, 1H), 3.49 (s, 1H), 3.48 (d, 1H), 3.29 (s, 3H), 0.99 (d, 3H).

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A crystalline form of a compound of Formula XI in the form of Form 2, 2-(2-fluoro-4-iodophenylamino)-N-(2-hydroxyethoxy)-1,5-dimethyl-6-oxo-1,6-dihydropyridine-3-carboxamide.

2. A crystalline form of a compound of Formula XI in the form of Form 2, 2-(2-fluoro-4-iodophenylamino)-N-(2-hydroxyethoxy)-1,5-dimethyl-6-oxo-1,6-dihydropyridine-3-carboxamide characterized by an X-ray diffraction pattern having characterizing peaks at about 9.5, 12.6, 14.7 and 19.6 on the 2θ scale.

3. A crystalline form of a compound of Formula XI according to claim 2 characterized by an X-ray diffraction pattern substantially as shown in FIG. 10.

4. A crystalline form of a compound of Formula XI in the form of Form 1, 2-(2-fluoro-4-iodophenylamino)-N-(2-hydroxyethoxy)-1,5-dimethyl-6-oxo-1,6-dihydropyridine-3-carboxamide.

5. A crystalline form of a compound of Formula XI in the form of Form 1, 2-(2-fluoro-4-iodophenylamino)-N-(2-hydroxyethoxy)-1,5-dimethyl-6-oxo-1,6-dihydropyridine-3-carboxamide characterized by an X-ray diffraction pattern having characterizing peaks at about 9.2, 13.0, 18.3, 21.0 and 21.7 on the 2θ scale.

6. A crystalline form of a compound of Formula XI according to claim 5 characterized by an X-ray diffraction pattern substantially as shown in FIG. 11.

7. A method of producing a producing a MEK inhibitory effect in a warm-blooded animal in need of such treatment which comprises administering to said animal an effective amount of a compound according to claim 1.

8. A pharmaceutical composition comprising a compound according to claim 1 in association with a pharmaceutically acceptable carrier.

9. A process for preparing a compound of Formula XI in the form of Form 1, 2-(2-fluoro-4-iodophenylamino)-N-(2-hydroxyethoxy)-1,5-dimethyl-6-oxo-1,6-dihydropyridine-3-carboxamide according to claim 4, which comprises:
   a) contacting 2-(2-fluoro-4-iodophenylamino)-1,5-dimethyl-6-oxo-1,6-dihydropyridine-3-carboxylic acid (2-vinyloxyethoxy)-amide with an acidic mixture for a sufficient time to convert the compound into 2-(2-fluoro-4-iodophenylamino)-N-(2-hydroxyethoxy)-1,5-dimethyl-6-oxo-1,6-dihydropyridine-3-carboxamide;
   b) allowing the material from step a) to crystallize from an organic solvent containing a seed of Form 1, 2-(2-fluoro-4-iodophenylamino)-N-(2-hydroxyethoxy)-1,5-dimethyl-6-oxo-1,6-dihydropyridine-3-carboxamide; and
   c) isolating the Form 1, 2-(2-fluoro-4-iodophenylamino)-N-(2-hydroxyethoxy)-1,5-dimethyl-6-oxo-1,6-dihydropyridine-3-carboxamide.

10. The process of claim 9, wherein the acidic mixture of step a) is an aqueous acid-ethyl acetate solvent system.

11. The process of claim 9, wherein the organic solvent of step b) is ethyl acetate.

12. A process for preparing a compound of Formula XI in the form of Form 1, 2-(2-fluoro-4-iodophenylamino)-N-(2-hydroxyethoxy)-1,5-dimethyl-6-oxo-1,6-dihydropyridine-3-carboxamide according to claim 4, which comprises:
   a) agitating Form 2, 2-(2-fluoro-4-iodophenylamino)-N-(2-hydroxyethoxy)-1,5-dimethyl-6-oxo-1,6-dihydropyridine-3-carboxamide with a small quantity of Form 1, 2-(2-fluoro-4-iodophenylamino)-N-(2-hydroxyethoxy)-1,5-dimethyl-6-oxo-1,6-dihydropyridine-3-carboxamide in an organic solvent; and
   b) isolating the Form 1, 2-(2-fluoro-4-iodophenylamino)-N-(2-hydroxyethoxy)-1,5-dimethyl-6-oxo-1,6-dihydropyridine-3-carboxamide.

13. The method of claim 12, wherein the organic solvent is ethyl acetate.

14. The method of claim 12, wherein step a) is carried out at a temperature from about 50 to 60° C.

15. A process for preparing a compound of Formula XI in the form of Form 2, 2-(2-fluoro-4-iodophenylamino)-N-(2-hydroxyethoxy)-1,5-dimethyl-6-oxo-1,6-dihydropyridine-3-carboxamide according to claim 1, which comprises
   a) contacting 2-(2-fluoro-4-iodophenylamino)-1,5-dimethyl-6-oxo-1,6-dihydropyridine-3-carboxylic acid (2-vinyloxyethoxy)-amide with an acidic mixture for a sufficient time to convert the compound into 2-(2-fluoro-4-iodophenylamino)-N-(2-hydroxyethoxy)-1,5-dimethyl-6-oxo-1,6-dihydropyridine-3-carboxamide;
   b) allowing the material from step a) to crystallize from an organic solvent ; and
   c) isolating the Form 2, 2-(2-fluoro-4-iodophenylamino)-N-(2-hydroxyethoxy)-1,5-dimethyl-6-oxo-1,6-dihydropyridine-3-carboxamide.

16. A process according to claim 15, wherein in step b) the organic solvent contains a seed of Form 2, 2-(2-fluoro-4-iodophenylamino)-N-(2-hydroxyethoxy)-1,5-dimethyl-6-oxo-1,6-dihydropyridine-3-carboxamide.

17. A process according to claim 15, wherein the organic solvent in step b) is ethyl acetate.

18. A pharmaceutical composition comprising a compound according to claim 4 in association with a pharmaceutically acceptable carrier.

19. A method of producing a producing a MEK inhibitory effect in a warm-blooded animal in need of such treatment which comprises administering to said animal an effective amount of a compound according to claim 4.

20. 2-(2-Fluoro-4-iodophenylamino)-N-(2-hydroxyethoxy)-1,5-dimethyl-6-oxo-1,6-dihydropyridine-3-carboxamide in crystalline form.

21. A pharmaceutical composition comprising a compound according to claim 2 in association with a pharmaceutically acceptable carrier.

22. A pharmaceutical composition comprising a compound according to claim 5 in association with a pharmaceutically acceptable carrier.

23. A method of producing a producing a MEK inhibitory effect in a warm-blooded animal in need of such treatment which comprises administering to said animal an effective amount of a compound according to claim 2.

24. A method of producing a producing a MEK inhibitory effect in a warm-blooded animal in need of such treatment which comprises administering to said animal an effective amount of a compound according to claim 5.

* * * * *